United States Patent
Owens et al.

(10) Patent No.: US 9,742,843 B2
(45) Date of Patent: Aug. 22, 2017

(54) METHOD AND SYSTEM FOR ENABLING DATA SHARING BETWEEN SOFTWARE SYSTEMS

(71) Applicant: ThoughtWire Holdings Corp., Toronto (CA)

(72) Inventors: Stephen Paul Owens, Caledon (CA); Michael Lorne Monteith, Toronto (CA); Jose Humberto Terra Nunes, Toronto (CA); David Ferreira Faria, Vaughan (CA)

(73) Assignee: THOUGHTWIRE HOLDINGS CORP., Toronto, ON (CA)

( * ) Notice: Subject to any disclaimer, the term of this patent is extended or adjusted under 35 U.S.C. 154(b) by 70 days.

(21) Appl. No.: 13/804,168

(22) Filed: Mar. 14, 2013

(65) Prior Publication Data

US 2014/0280535 A1 Sep. 18, 2014

(51) Int. Cl.
| | |
|---|---|
| *G06F 9/44* | (2006.01) |
| *G06F 12/14* | (2006.01) |
| *G06F 7/00* | (2006.01) |
| *H04L 29/08* | (2006.01) |
| *G06Q 40/08* | (2012.01) |
| *G06Q 50/24* | (2012.01) |

(52) U.S. Cl.
CPC .......... *H04L 67/1095* (2013.01); *H04L 67/14* (2013.01); *G06Q 40/08* (2013.01); *G06Q 50/24* (2013.01)

(58) Field of Classification Search
CPC ...... H04L 67/12; H04L 67/10; H04L 67/1002
USPC ........................................................ 709/204
See application file for complete search history.

(56) References Cited

U.S. PATENT DOCUMENTS

| | | |
|---|---|---|
| 6,292,804 B1 | 9/2001 | Ardoin et al. |
| 6,732,331 B1 | 5/2004 | Alexander |
| 7,526,481 B1 * | 4/2009 | Cusson ............. G06F 17/30902 |

(Continued)

FOREIGN PATENT DOCUMENTS

EP 2650832 A1 10/2013

OTHER PUBLICATIONS

Google, "Gadget-to-Gadget Communication (Deprecated)", http://code.google.com/apis/gadgets/docs/pubsub.html.

(Continued)

*Primary Examiner* — Kevin Bates
*Assistant Examiner* — Golam Mahmud
(74) *Attorney, Agent, or Firm* — Kagan Binder, PLLC

(57) ABSTRACT

A method and system for enabling data sharing between software systems is provided. At least one data-sharing session is managed for each of a plurality of users with a server computer system. Each of the data-sharing sessions has a set of software systems associated with the user participating therein. The server computer system maintains requests for the software systems to be notified of updates to values of sets of requested data items. The set of software systems share data item values in the data-sharing session. The server computer system stores the shared data item values, and resolves the shared data item values to the requested data items using semantic descriptions provided for the shared data item values and the requested data items. Available updates to the shared data item values resolving to the sets of requested data items are provided to the software systems.

50 Claims, 40 Drawing Sheets

(56) References Cited

U.S. PATENT DOCUMENTS

| | | | |
|---|---|---|---|
| 7,680,820 B2* | 3/2010 | Denoue | G06Q 10/10 |
| | | | 707/608 |
| 7,853,618 B2* | 12/2010 | Yuan et al. | 707/794 |
| 7,934,207 B2 | 4/2011 | Gustafsson et al. | |
| 7,971,179 B2 | 6/2011 | Venolia | |
| 8,296,362 B2 | 10/2012 | Roberts et al. | |
| 8,301,660 B2 | 10/2012 | Yalamanchi | |
| 9,244,965 B2 | 1/2016 | Monteith et al. | |
| 2002/0010744 A1* | 1/2002 | Prell | G06F 9/5061 |
| | | | 709/205 |
| 2003/0074352 A1 | 4/2003 | Raboczi et al. | |
| 2003/0105746 A1 | 6/2003 | Stickler | |
| 2003/0236820 A1 | 12/2003 | Tierney et al. | |
| 2004/0015426 A1 | 1/2004 | Tadayon et al. | |
| 2004/0044866 A1 | 3/2004 | Casazza | |
| 2004/0049697 A1* | 3/2004 | Edwards, Jr. | G06F 21/31 |
| | | | 726/5 |
| 2004/0148333 A1 | 7/2004 | Manion et al. | |
| 2004/0221053 A1 | 11/2004 | Codella et al. | |
| 2004/0243531 A1 | 12/2004 | Dean | |
| 2005/0021523 A1 | 1/2005 | Farag | |
| 2005/0044063 A1 | 2/2005 | Barsness et al. | |
| 2005/0055211 A1 | 3/2005 | Claudatos et al. | |
| 2005/0060342 A1 | 3/2005 | Farag | |
| 2005/0066118 A1 | 3/2005 | Perry et al. | |
| 2005/0165719 A1* | 7/2005 | Greenspan | H04L 29/06027 |
| 2005/0202392 A1* | 9/2005 | Allen | G09B 7/00 |
| | | | 434/362 |
| 2006/0004847 A1 | 1/2006 | Claudatos et al. | |
| 2006/0117073 A1 | 6/2006 | Bosworth et al. | |
| 2006/0178910 A1 | 8/2006 | Eisenberger et al. | |
| 2006/0190455 A1 | 8/2006 | Braddy et al. | |
| 2007/0011147 A1 | 1/2007 | Falkenberg | |
| 2007/0022107 A1 | 1/2007 | Yuan et al. | |
| 2007/0033109 A1 | 2/2007 | Patten et al. | |
| 2007/0033142 A1 | 2/2007 | Patten et al. | |
| 2007/0088831 A1 | 4/2007 | Pallamreddy et al. | |
| 2007/0124291 A1 | 5/2007 | Hassan et al. | |
| 2007/0150480 A1 | 6/2007 | Hwang et al. | |
| 2007/0180122 A1 | 8/2007 | Barrett | |
| 2007/0186028 A2 | 8/2007 | Kissell | |
| 2007/0240055 A1* | 10/2007 | Ting | G06F 9/4443 |
| | | | 715/704 |
| 2007/0277148 A1 | 11/2007 | Venolia | |
| 2008/0040308 A1 | 2/2008 | Ranganathan et al. | |
| 2008/0046803 A1 | 2/2008 | Beauchamp et al. | |
| 2008/0059500 A1 | 3/2008 | Symens | |
| 2008/0082612 A1 | 4/2008 | Declerck | |
| 2008/0134207 A1 | 6/2008 | Chamieh et al. | |
| 2008/0198871 A1 | 8/2008 | Shahidi et al. | |
| 2008/0208676 A1 | 8/2008 | Williams et al. | |
| 2008/0215580 A1 | 9/2008 | Altinel et al. | |
| 2008/0244075 A1 | 10/2008 | Kuo et al. | |
| 2008/0256253 A1 | 10/2008 | Branson et al. | |
| 2008/0313229 A1 | 12/2008 | Taswell | |
| 2008/0313296 A1 | 12/2008 | Muller | |
| 2008/0320417 A1 | 12/2008 | Begley et al. | |
| 2009/0006627 A1 | 1/2009 | Castellucci et al. | |
| 2009/0030982 A1 | 1/2009 | Spivack et al. | |
| 2009/0132556 A1 | 5/2009 | Gupta et al. | |
| 2009/0144365 A1 | 6/2009 | Korat | |
| 2009/0216714 A1 | 8/2009 | Gonzalez et al. | |
| 2009/0265464 A1 | 10/2009 | Jakobson | |
| 2009/0327502 A1* | 12/2009 | Brewer | H04L 63/10 |
| | | | 709/229 |
| 2010/0131868 A1 | 5/2010 | Chawla et al. | |
| 2010/0179836 A1* | 7/2010 | Hasan | G06F 19/322 |
| | | | 705/3 |
| 2011/0040846 A1 | 2/2011 | Weinryb et al. | |
| 2011/0098056 A1 | 4/2011 | Rhoads et al. | |
| 2011/0131119 A1 | 6/2011 | Ernst | |
| 2011/0138446 A1* | 6/2011 | Barrett | G06F 21/31 |
| | | | 726/3 |
| 2011/0179110 A1 | 7/2011 | Soloway | |
| 2011/0209138 A1* | 8/2011 | Monteith et al. | 717/172 |
| 2011/0246530 A1 | 10/2011 | Malafsky | |
| 2011/0296043 A1* | 12/2011 | Sutton | G06Q 10/10 |
| | | | 709/229 |
| 2011/0314387 A1 | 12/2011 | Gold et al. | |
| 2011/0314388 A1 | 12/2011 | Wheatley | |
| 2012/0232929 A1* | 9/2012 | Experton | G06Q 50/22 |
| | | | 705/3 |
| 2012/0310900 A1 | 12/2012 | Monteith | |
| 2013/0097086 A1* | 4/2013 | Dala | G06F 19/322 |
| | | | 705/51 |
| 2013/0151301 A1 | 6/2013 | Robb | |
| 2013/0268357 A1 | 10/2013 | Heath | |
| 2013/0318347 A1 | 11/2013 | Moffat | |
| 2015/0213411 A1* | 7/2015 | Swanson | G06Q 10/06311 |
| | | | 705/301 |

OTHER PUBLICATIONS

Expressor Software, "expressor data integration products", http://www.expressor-software.com/products-overview.htm.
Search Report for corresponding EP Patent Application No. 14275068.6, dated Apr. 1, 2015.
Search Report for corresponding UK Patent Application No. GB1404645.2, dated Sep. 26, 2014.
Search Report for corresponding UK Patent Application No. GB1404638.7, dated Sep. 22, 2014.
Office Action for U.S. Appl. No. 12/710,099, dated Jan. 5, 2015.
Office Action for U.S. Appl. No. 13/578,552, dated Mar. 13, 2015.

* cited by examiner

METHOD AND SYSTEM FOR ENABLING DATA SHARING BETWEEN SOFTWARE SYSTEMS

FIELD OF THE INVENTION

The present invention relates generally to information systems. In particular, the invention relates to a method and system for enabling data sharing between software systems.

BACKGROUND OF THE INVENTION

Much of what the average individual experiences as work, learning or play is accomplished through their interactions with computers and software. Billions of times a day, hundreds of millions of people interact with computers and software in their daily pursuits. Increasingly, people are faced with the challenge of working with multiple independent software systems to perform everything from the most mundane to the most complicated tasks. As used herein, "software system" refers to one or more applications, programs, services, databases, firmware, executed scripts, middleware, sets of functionality available via web pages, etc. that share and/or receive data. In many cases, no single software system contains all of the required information or functionality and it is often the individual's job to act as the point of connection amongst the software systems they use.

FIG. 1 shows an example of a prior art system that illustrates how a person might interact with various software systems to complete a task. A medical practitioner uses the software systems to schedule patients, record details of the patient during the visit, and then prepare an invoice for the patient. A pair of personal computing devices used directly by the medical practitioner are in communication with a number of other computer systems.

As used herein, "personal computing device" is a computing device with which a user directly interacts. Examples of personal computing devices include smartphones, tablet computing devices, personal computers, smart thermostats, portable media players, global positioning system units, and display panels.

In this illustrated example, a first personal computing device, tablet 20a, is used by the medical practitioner to review and record medical details of the patient. The medical details are stored in a database server 24 accessed by the tablet 20a over an intranet 28. In addition, a second personal computing device, desktop computer 20b, is used by the medical practitioner to schedule patients and prepare invoices. The invoices include a calculation of the amount payable by the patient net of any amounts payable under the patient's insurance plans. In order to determine the amounts payable under the patient's insurance plans, the medical practitioner uses the desktop computer 20b to access an insurance Web portal operated by a Web portal server 32 via the Internet 36 from behind a firewall 40.

FIG. 2 shows the various software applications executing on the tablet 20a and the desktop computer 20b that the medical practitioner uses. A first software system 44a includes a patient medical database client 48 executing on the tablet 20a that is in communication with the database server 24 to access and update the data stored in a patient medical database 52 managed by the database server 24. The patient medical database client 48 is a native application for the tablet 20a that provides access to patient medical data stored in the patient medical database 52, and enables diary entries for procedures performed, medications prescribed, and observations made. The patient medical database 52 maintains data for patients across a number of medical practitioners. Each patient's patient medical data in the database 52 is associated with a patient ID.

A second software system 44b includes a clinical management application 56 for scheduling patient consultations and procedures, recording billable services and products provided to the patient, and generating invoices for patient visits for each patient and recording other accounting information. The clinical management application 56 enables entries to be made for visits, medications prescribed and provided, procedures, phone consultations, equipment provided, etc. As will be understood, some of the same entries made in the patient medical database client 48 are duplicated in the client management application 56. Patients are set up in the clinical management application 56, together with details for any insurance plans under which they have coverage, such as the name of the insurance company and the number of the insurance policy under which the patient has coverage. In addition, the corresponding patient ID from the patient medical database 52 is entered into the clinical management application 56 to enable rapid lookup of the patient's medical data via the patient's medical database client 48. Once the list of services and products provided to a patient has been entered, the gross charges are then determined for the services and products by the clinical management application 56. The amounts covered under the patient's insurance plans for each service and product can be then entered into the clinical management application 56 to enable it to generate a detailed breakdown of the net amount payable by the patient for each product or service, as well as a total.

A third software system 44c for determining the amounts payable under a patient's insurance plans includes a Web portal page 60 that is generated by the Web portal server 32 and presented on a Web browser executing on the personal computing device 20b. The Web portal page 60 includes an insurance claim portlet 64 selected from a portlet library 68 that is injected into the Web portal page 60 by the Web portal server 32. The Web portal page 60 enables the medical practitioner to select an insurance company, an insurance policy number corresponding to an insurance policy under which a patient has coverage, and a procedure, consultation or product code, and returns an amount covered by the insurance plan in question for the procedure or consultation.

FIG. 3 shows the interaction required of a user 72 with the three software systems 44a, 44b, and 44c in order to create an invoice for a patient. The lack of integration between these software systems means that the user 72 is burdened with the complex, time-consuming and error-prone job of logging into and interacting with each software system individually and trying to perform a coordinated task across them. The user 72 spends valuable time copying and pasting and re-entering information, switching between the applications and individual web pages he or she need to use, while at the same time trying to remember the information obtained from one application that needs to be entered into another.

To start, the user 72 launches the clinical management application 56 on the desktop computer 20b and views the schedule to see the scheduled list of patients for the day. When a patient is to be examined, treated, etc., the user 72 manually re-enters the patient ID from the clinical management application 56 on the desktop computer 20b into the patient medical database client 64 on the tablet 20a. The user 72 then uses the patient medical database client 48 to pull up the patient's data, review previous entries made for the patient and then register observations, procedures performed, medication prescribed, etc. When the work has been performed for a patient, the user 72 then returns to the clinical management application 56 executing on the desktop computer 20b, re-enters the information regarding the procedures performed, the consultations given, etc. Next, the user 72 enters the patient's ID, insurance policy information and the procedure/consultation codes for the work performed into the insurance claim portlet 64 on the Web portal page 60 so that the amounts payable under the patient's insurance plan(s) can be determined. This can be done using copying-and-pasting or manual entry. The amounts payable under the patient's insurance plan(s) are then entered by the user 72 into the clinical management application, again either via copying-and-pasting or manually, so that the patient-payable amount can be determined and a comprehensive invoice can be prepared for the patient by the clinical management application 56.

As can be appreciated, the amount of human interaction and potential for human error for using software systems in this manner is significant. Whether the task relates to a person trying to use the Internet to research and arrange their dream vacation, an agent in a customer services department trying to resolve an issue, a physician in an emergency ward trying to quickly access all of the information available about their patient, or a lawyer delving into various software systems to assemble a full picture of a client, the problem surfaces everywhere people use software systems during their day. The effects of the problem are universal and far-reaching, negatively affecting individual productivity, costs, quality of work and satisfaction. In aggregate, the implications are staggering and represent an untapped potential source of improvement in almost every industry.

Where two or more software systems are on separate computing devices, such as in the system of FIGS. 1 to 3, cutting and pasting or client-side integration of such software systems may not be an option. In these cases, data is generally shared by user re-entry of data from one software system into another software system, or by some manual transfer of information, such as via email or the like. This process can be cumbersome and error-prone.

One approach taken to address this type of problem is to integrate the software systems to enable data sharing between them. System integration has traditionally been done in a point-to-point fashion using programmatic connections between the server-side components of the separate systems in an invocation/response pattern. Usually, the connection is made via an application programming interface ("API") exposed by one of the software systems to be integrated. As these APIs are typically software system-specific, knowledge of various APIs is generally required when integrating new software systems with others. Each software system generally has different identifiers for data items, thus requiring the integrator to have knowledge of the data items and structures for each software system that is to be integrated. Further, the events for each integrated software system need to make sense of the data moving between integrated software systems. These events are typically custom-designed and have to correspond with events occurring in other software systems. Examples of events include the completion of a database transaction, the appearance of a file in a directory, or the appearance of a message in a queue. Each of these events may require translating into something locally meaningful for each integrated software system.

Integration systems have been developed to handle the integration between different software systems, but these integration systems can encounter all the same issues as when directly integrating software systems.

In some cases, the use of an integration server is not feasible as a cost-efficient solution for integrating software systems.

Turning back to the software systems of FIGS. 2 and 3, as will be readily understood, there isn't a feasible manner in which an integration server could be used to reduce the manual interaction of a user in order to complete a task. The patient medical database 52 maintains patient medical data that is confidential and is not directly cross-relatable to the information maintained by the Web portal server 32. As a result, there is no easy way to integrate these two resources. The data held within the clinical management application 56 is stored on the desktop computer 20b and is thus not readily integrated with the patient medical database 52 nor with the Web portal server 32. Theoretically, the clinical management application 56 could be customized to retrieve insurance information from various insurance portals, but it would have to be updated whenever there is a change in the location or format of this information for any of the insurance portals.

Server-side integration becomes even more challenging with so many widely-separated software systems coming together only on a computing device being used by an end-user and, often, on an ad-hoc basis. Predicting the software systems that a single user, let alone multiple users, may wish to interact with to complete a task is highly challenging. The integration of all of the servers for each of these software systems is still more cumbersome. Even where server-side integration has been performed for two servers, user authentication may be very onerous. The user has to log in to a first server with a first set of login credentials and then have the first server use a system account to access resources and/or functionality available via a second server. The second server would have to extend a broad range of trust to a system account and won't know at all on whose behalf the first server is acting during a particular transaction. Thus, server-side integrations are high-cost solutions that can be inappropriate for such ad-hoc pairings of software systems by users.

Point-to-point integrations can work acceptably for small numbers of software systems with relatively simple data to be shared. Due to the complexity of such integrations, they are generally reserved for enterprise systems. As the interaction of each software system with each other software system is explicitly programmed, the integration of each additional software system requires significantly-increased effort. Another issue is that it is generally very difficult for a third party to enhance the integration between software systems.

There are issues with integrating software systems on the personal computing device. In some circumstances, personal computing devices (i.e., those with which an end user directly interacts) upon which such software systems operate may have processing power that is constrained. It can, however, be desirable to have software systems interact with components, services and/or databases that are located on remote computer systems. In some scenarios, there can be latency issues or relatively high data transmission costs associated with the connections to such remote computer systems. Further, communicating all of the data from a database required to generate a user interface can increase the security risk level. Communications between the personal computing device and resources such as database servers can be hindered by firewalls. Still further, if the personal computing device undergoes a system failure, all of the data would be lost if the software systems are integrated client-side. As a result, it can be undesirable to have integration occur on the computing device.

Yet another issue is that data persistence is not handled very well in most integrations. During the processing of a transaction, if a software system responsible for performing a task is not present, generally the transaction will fail. In order to instill robustness into such integrated software systems, event-handling and/or message queuing has to be added as fail-safes for various scenarios, adding further to the complexity of such integrations.

One solution proposed, and deprecated, for data sharing by Google can be found at http://code.google.com/apis/gadgets/docs/pubsub.html. The proposal describes a publish-subscribe framework to pass messages from one gadget to another. Google gadgets are canned sets of functionality that can be included in a web portal, such as iGoogle. Google previously supported this functionality which would not be present in other portals. Gadgets with data to share would publish the data using a set of defined identifiers via channels, as long as the gadgets were aware that at least one other gadget was interested in the data. Gadgets interested in the data would declare their interest in knowing when the values of those data items have changed. As the data is pushed via channels at the time there is a change, however, the state of the data may be unavailable to new gadgets. Further, gadgets have to have been programmed with knowledge of the defined data identifiers. This solution is specific to Google gadgets and is not portable to other types of software systems.

It is therefore an object of the invention to provide a novel method and system for enabling data sharing between software systems.

SUMMARY OF THE INVENTION

In accordance with an aspect of the invention, there is provided a method for enabling data sharing between software systems, comprising:

managing at least one data-sharing session for each of a plurality of users with a server computer system, each said data-sharing session having a set of software systems associated with said user participating therein, said server computer system maintaining requests for said software systems to be notified of updates to values of sets of requested data items, said set of software systems sharing data item values in said data-sharing session, said server computer system storing said shared data item values, resolving said shared data item values to said requested data items using semantic descriptions provided for said shared data item values and said requested data items, and providing available updates to said shared data item values resolving to said sets of requested data items to said software systems.

The server computer system can maintain separate user spaces in storage of the server computer system for each user in which the data item values shared by software systems associated with the user are stored.

The at least one of the software systems associated with each user can be executing on a personal computing device operated by the user. The personal computing device can communicate login credentials for the user to the server computer system to associate the at least one software system with the user.

Each data-sharing session can correspond to one of a plurality of data-sharing session types, and the server computer system can use a collaboration definition for each data-sharing session type to define what types of software systems can participate in the data-sharing sessions of the data-sharing session type. The server computer system can use a participant definition for each software system type to define what data items it can request values for. The participant definition can include the semantic descriptions for the data items that the software system type can request values for. The participant definition can define which the data items the software systems of the software system type can share values for. The participant definition includes the semantic descriptions for the data items that the software systems of the software system type can share values for.

The server computer system can use at least one ontology dataset to resolve the shared data item values to the requested data items.

The collaboration definition can specify at least one ontology dataset that the server computer system uses to resolve the shared data item values to the requested data items.

The participant definition can include configuration information for configuring the software systems of the software system type.

The server computer system can create each data-sharing session in response to receiving a collaboration creation request specifying the collaboration definition corresponding to the data-sharing session type that is desired.

The server computer system can permit only one of the software systems of each software system type specified in the collaboration definition to participate in the data-sharing session. The server computer system can receive a request from one of the software systems to participate in a data-sharing session, the request identifying the software system type of the one software system, the server computer system only permitting the software system to participate in one of the data-sharing sessions for which the corresponding collaboration definition specifies that the software system type of the one software system is permitted to participate therein.

The server computer system can register the one software system outside of the data-sharing sessions if all of data-sharing sessions in which the one software system is permitted to participate in already have other of the software systems of the software system type participating therein, and can subsequently register the one software system in one of the data-sharing sessions in which the one software system is permitted to participate in has capacity for the one software system.

The server computer system can maintain separate user spaces in storage of the server computer system for each user in which the data item values shared by the software systems associated with the user are stored, and register the one software system in the user space corresponding to the user with which the one software system is associated and outside of the data-sharing sessions if all of the data-sharing sessions in which the one software system is permitted to participate in already have other of the software systems of the software system type participating therein until one of the data-sharing sessions in which the one software system is permitted to participate in has capacity for the one software system.

The server computer system can determine that only one of the data-sharing sessions in which the one software system is permitted to participate in has capacity for the one software system, and can register the one software system in the one data-sharing session.

The server computer system can determine that at least two of the data-sharing sessions in which the one software system is permitted to participate in has space for the one software system, and can report an error to the one software system.

The server computer system can receive a request from one of the software systems to participate in a data-sharing session, the request specifying an identifier for a particular one of the data-sharing sessions managed by the server computer system, the server computer system placing the one software system in the particular one data-sharing session if the collaboration definition associated with the particular data-sharing session indicates that the one software system is permitted to join the particular data-sharing session and if the particular data-sharing session has capacity for the one software system.

The server computer system can determine that at least two of the data-sharing sessions in which the one software system is permitted to participate in has space for the one software system, and can register the one software system in one of the at least two data-sharing sessions based on heuristics.

The server computer system can register the one software system in a later created one of the at least two data-sharing sessions, in an earlier created one of the at least two data-sharing sessions, or in one of the at least two data-sharing sessions having more recent data-sharing activity.

According to another aspect of the invention, there is provided a computer system for enabling data sharing between software systems, comprising:

a processor;

storage; and a server executed by said processor and managing at least one data-sharing session in storage for each of a plurality of users, said server having an interface receiving registration requests from software systems, each of said software systems being associated with one of said users, said server being configured to register each of said software systems in one of said data-sharing sessions of said associated user, said server maintaining a request for a set of data items from a first of said software systems in said data-sharing session and resolving said requested set of data items to a set of data item values shared by other of said software systems in said one data-sharing session based on semantic descriptions of said requested set of data items and said shared data item values, said server providing said shared data item values resolving to said requested set of data items to said first software system.

The server can maintain separate user spaces in storage of the computer system for each user in which the data item values shared by software systems associated with the user are stored.

At least one of the software systems associated with each user can be executing on a personal computing device operated by the user, and the server can receive login credentials for the user from the personal computing device to associate the at least one software system with the user.

Each data-sharing session can correspond to one of a plurality of data-sharing session types, and the server can use a collaboration definition for each data-sharing session type to define what types of the software systems can participate in the data-sharing sessions of the data-sharing session type. The server can use a participant definition for each software system type to define what data items it can request values for. The participant definition can include semantic descriptions for the data items that the software system type can request values for.

The participant definition can define which data items the software systems of the software system type can share values for.

The participant definition can include the semantic descriptions for the data items that the software systems of the software system type can share values for.

The server can use at least one ontology dataset to resolve the shared data item values to the requested data item values.

The collaboration definition can specify at least one ontology dataset that the server computer system uses to resolve the shared data item values to the requested data items.

The participant definition can include configuration information for configuring the software systems of the software system type.

The server can create each data-sharing session in response to receiving a collaboration creation request specifying the collaboration definition corresponding to the data-sharing session type that is desired.

The server can permit only one of the software systems of each software system type specified in the collaboration definition to participate in the data-sharing session. The server can receive a request from one of the software systems to participate in a data-sharing session, the request identifying the software system type of the one software system, the server only permitting the software system to participate in one of the data-sharing sessions for which the corresponding collaboration definition specifies that the software system type of the one software system is permitted to participate therein.

The server can register the one software system outside of the data-sharing sessions if all of the data-sharing sessions in which the one software system is permitted to participate in already have other of the software systems of the software system type participating therein, and subsequently register the one software system in the data-sharing sessions in which the one software system is permitted to participate in has capacity for the one software system.

The server can maintain separate user spaces in the storage for each user in which the data item values shared by the software systems associated with the user are registered, and can register the one software system in the user space corresponding to the user with which the one software system is associated and outside of the data-sharing sessions if all of the data-sharing sessions in which the one software system is permitted to participate in already have other of the software systems of the software system type participating therein until one of the data-sharing sessions in which the one software system is permitted to participate in has capacity for the one software system.

The server can determine that only one of the data-sharing sessions in which the one software system is permitted to participate in has capacity for the one software system, and register the one software system in the one data-sharing session.

The server can determine that at least two of the data-sharing sessions in which the one software system is permitted to participate in has space for the one software system, and report an error to the one software system.

The server can receive a request from one of the software systems to participate in a data-sharing session, the request specifying an identifier for a particular one of the data-sharing sessions managed by the server computer system, and can register the one software system in the particular one data-sharing session if the collaboration definition associated with the particular data-sharing session indicates that the one software system is permitted to join the particular data-sharing session and if the particular data-sharing session has capacity for the one software system.

The server can determine that at least two of the data-sharing sessions in which the one software system is permitted to participate in has space for the one software system, and register the one software system in one of the at least two data-sharing sessions based on heuristics. The server can register the one software system in a later created one of the at least two data-sharing sessions, in an earlier created one of the at least two data-sharing sessions, or in one of the at least two data-sharing sessions having more recent data-sharing activity.

According to a further aspect of the invention, there is provided a method for enabling data sharing between software systems, comprising:

receiving requests via a server computer system from software systems to join data-sharing sessions managed by said server computer system, each of said software systems being associated with a user;

registering, by said server computer system, for each user, said software systems associated therewith in a subset of said data-sharing sessions managed for said user;

maintaining requests for said software systems to be notified of updates to values of sets of requested data items;

storing data item values shared by said associated software systems in each said data-sharing session;

resolving said shared data item values to said requested data items for said data-sharing session using semantic descriptions provided for said shared data item values and said requested data items; and notifying said software systems requesting said requested data items when updates to said shared data item values resolving to said sets of requested data items are available.

According to yet another aspect of the invention, there is provided a method for enabling data sharing between software systems, comprising:

receiving a request to participate in a data-sharing session from a software system associated with a user via said server computer system;

registering, via said server computer system, said software system in a data-sharing session associated with said user and managed by said server computer system;

maintaining requests for said software system to be notified of updates to values of sets of requested data items;

storing data item values shared by other software systems in said data-sharing session;

resolving said shared data item values to said requested data items using semantic descriptions provided for said shared data item values and said requested data items; and notifying said software system when updates to said shared data item values resolving to said sets of requested data items are available.

According to still yet another aspect of the invention, there is provided a method for enabling data sharing between software systems, comprising:

receiving a request via a server computer system from a software system associated with a user to participate in a data-sharing session;

determining, by said server computer system, if a data-sharing session associated with said user is available;

creating, by said server computer system, said data-sharing session for said software system, if said data-sharing session is unavailable; and registering, by said server computer system, said software system in said data-sharing session.

BRIEF DESCRIPTION OF THE DRAWINGS

Embodiments will now be described, by way of example only, with reference to the attached Figures, wherein.

DETAILED DESCRIPTION OF THE EMBODIMENTS

Figure 1:
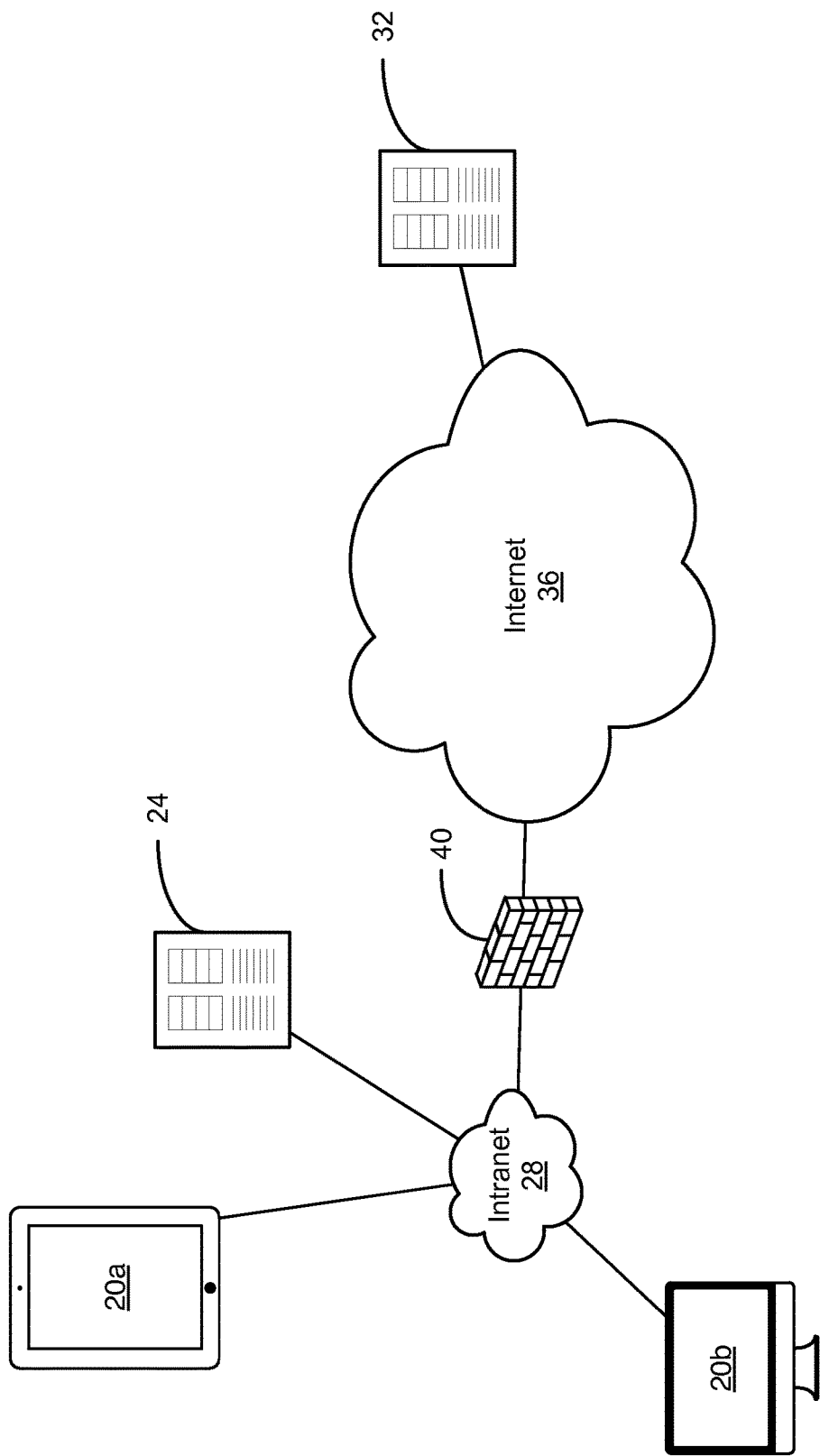
FIG. 1 shows a high-level architecture of a prior art system wherein a user interacts with various resources via two separate personal computing devices to complete a task.

The invention provides a new method and system for enabling data sharing between software systems using shared semantics managed by a data-sharing server computer system. The system enables people to complete tasks using a variety of software systems that work together in a very loosely coupled manner without programmatic knowledge of the other software systems.

Software systems generally represent resources that a person has access to. The resources can include data sources and/or functionality, such as web applications, databases, REST services and desktop applications, such as Microsoft Excel. Further, software systems can have multiple components that execute on the same or on two or more computing devices. For example, a Web page that is served to and is executed by a personal computing device can interact with a Web server computer system to provide access to resources available through the Web server computer system, such as an application server or a database. Collectively, the Web page, the Web server computer system and other resources to which it is coupled form a software system.

Instead of integrating the software systems programmatically or manually transferring the data from one software system to another, the invention enables software systems to assist in the completion of tasks in the system by participating in data-sharing sessions referred to as "collaborations". A "collaboration" is an arena managed by a stateful data-sharing service executed on the data-sharing server computer system in which each software system can share semantically identified data items and specify data that they need based on the semantics of that data. A collaboration is typically designed for the completion of a task. The stateful data-sharing service matches data shared by software systems with data other software systems requested using the semantic descriptions provided for both, and then notifies those other software systems when data matching what they requested is updated.

By having the stateful data-sharing service provided on a data-sharing server computer system manage the exchange of data, many advantages are realized. Data can be readily shared between software systems operating on the same or multiple computing devices and participating in the same collaboration. Additionally, as data shared by software systems is stored in a collaboration independent of the persistence of the software systems, two benefits are achieved. Firstly, the data can live independent of the state of the software systems and personal computing device(s). Secondly, software systems can share data asynchronously and without creating a dependency or a shared agreement on the structure of and protocol for exchanging the shared data. Thus, it is possible to have a first software system operating on a first computing device share some data and then, at a later time, even after the termination of operation of the first software system and/or the first computing device, a second software system operating on a second computing device can receive the data shared by the first software system. Further, no explicit programmatic coding is required for a software system to handle the event of data it desires being shared by another software system. The data shared and desired by each software system is simply declared, and the stateful data-sharing service executing on the data-sharing server computer system handles the channeling of data between software systems.

Additionally, the data-sharing server computer system may be better able to coordinate the exchange of data between the various computer systems in some circumstances, such as where a user is interacting via a wireless personal computing device with one or more software systems in a collaboration managed by the data-sharing server computer system, and one or more other software systems operating on other computer systems are also participating in the same collaboration. Latencies between the personal computing device and other computer systems can make it beneficial to have data sharing managed by the data-sharing server computer system in some circumstances. Also, by offloading the responsibility of coordinating the exchange of data between software systems to the data-sharing server computer system, the processing and memory demands of personal computing devices can be reduced. Still further, by enabling the sharing of data that forms part of the context of a user, semantically, instead of performing an enterprise integration, significant cost savings can be achieved.

This approach facilitates scaling to accommodate a large number and range of software systems. Using the invention, many software systems can participate without significantly increasing the integration complexity and without privileged access to the server infrastructure since integration is done on behalf of, and for the context of, a user. Instead, all of the software systems contribute to the shared data set in a way that enriches the available data for all software systems. Further, as the integration is not programmatic/point-to-point, and as it provides persistence of shared data after it is provided, it allows multiple software systems to asynchronously share data. Both the shared data and the shared semantics can be made persistent and externalized from the software systems. This combination of data and semantics can be valuable independent of any of the software systems. Network effects have long been recognized in connected software systems, a network effect occurring when the value of the system as a whole can go up quickly as a result of the number of connected software systems. The data sharing method and system of the invention exhibit network effects as the number of software systems and the quantity of shared data increase. Multiple software systems can be simultaneously working with the same shared data and can act to increase the value of the total shared data across the system. The stateful data-sharing service coordinates transactions by simply receiving requests for data, and responding to the requests when values for data items that semantically match the requested data are available, making such transactions data-driven and not event-driven.

As an example, if software system 1 requires both value A and value B to do its job, then software system 2 could contribute value A and software system 3 could contribute value B. As far as software system 1 is concerned, it would get the information it needs and wouldn't even be aware that multiple software systems were participating. In addition, it would not matter when the information was provided by the first two software systems, on which computing devices, as long as software system 1 was able to receive values A and B on or after when they became available. That is, software systems 2 and 3 may very well have ceased participating but the information they provided can still live in a collaboration and can be used to fulfill future queries.

Figure 4:
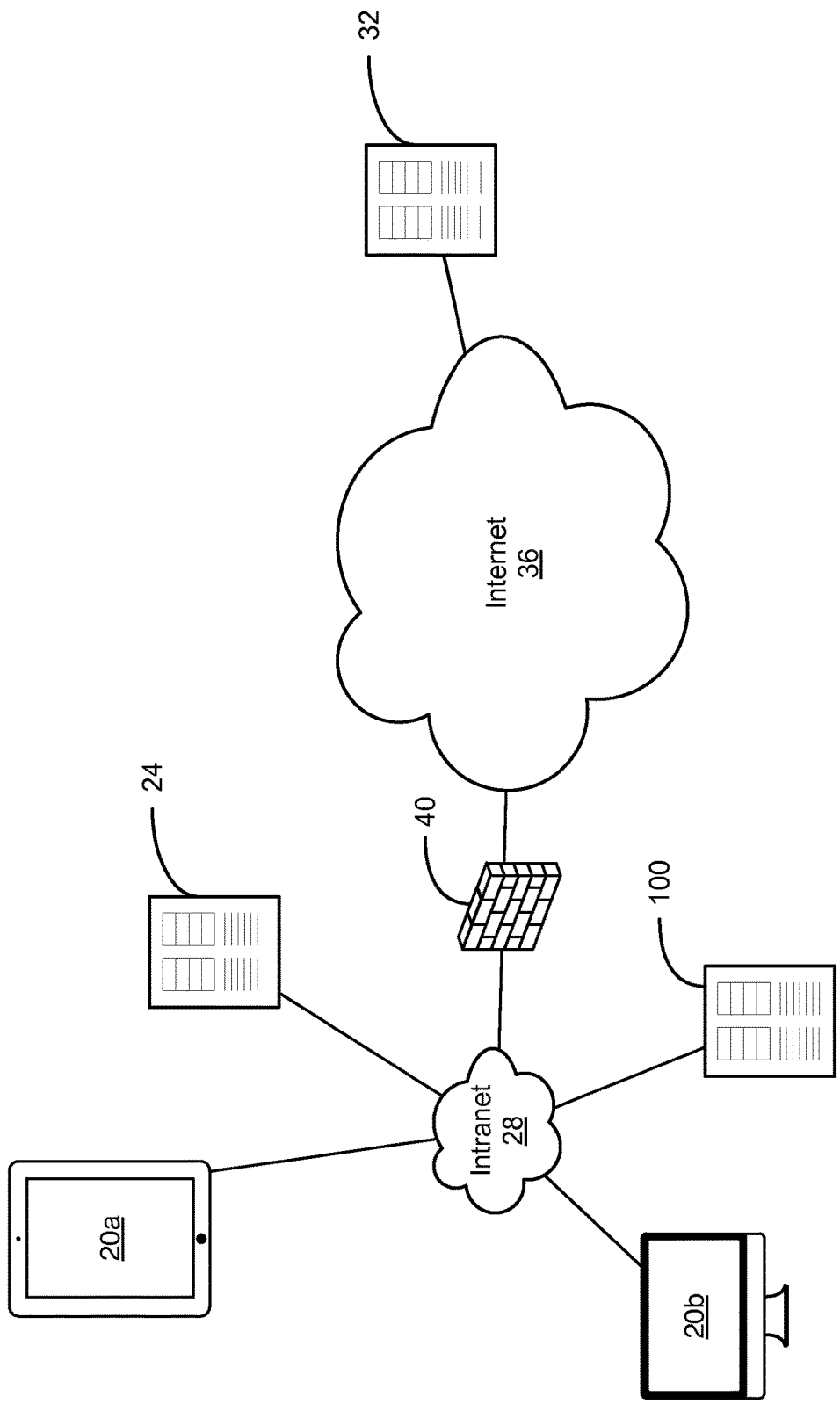
FIG. 4 shows a high-level architecture of a data-sharing server computer system for enabling data-sharing between software systems that are similar to those of FIG. 2 in accordance with an embodiment of the invention and its operating environment.

A system in accordance with an embodiment of the invention and its operating environment is shown in FIG. 4. As can be seen, the system of FIG. 4 is similar to that of FIG. 1, with the introduction of a new component. A data-sharing server computer system 100 that manages the exchange of data is shown in communication with the database server 24 via the intranet 28. The data-sharing server computer system 100 and the database server 24 are computer systems that can include one or more physical computers, but are each a single physical computer in the illustrated embodiment. The intranet 28 may be a wired network, a wireless network, or a combination thereof. The pair of personal computing devices, namely the tablet 20*a* and the desktop computer 20*b*, are in communication with the data-sharing server computer system 100 via the intranet 28. The intranet 28 is coupled to a large, public communications network, such as the Internet 36, via the firewall 40. The tablet 20*a*, the desktop computer 20*b*, and the data-sharing server computer system 100 are also in communication with the Web portal server 32 via the Internet 36.

Data-Sharing Server Computer System

Figure 5:
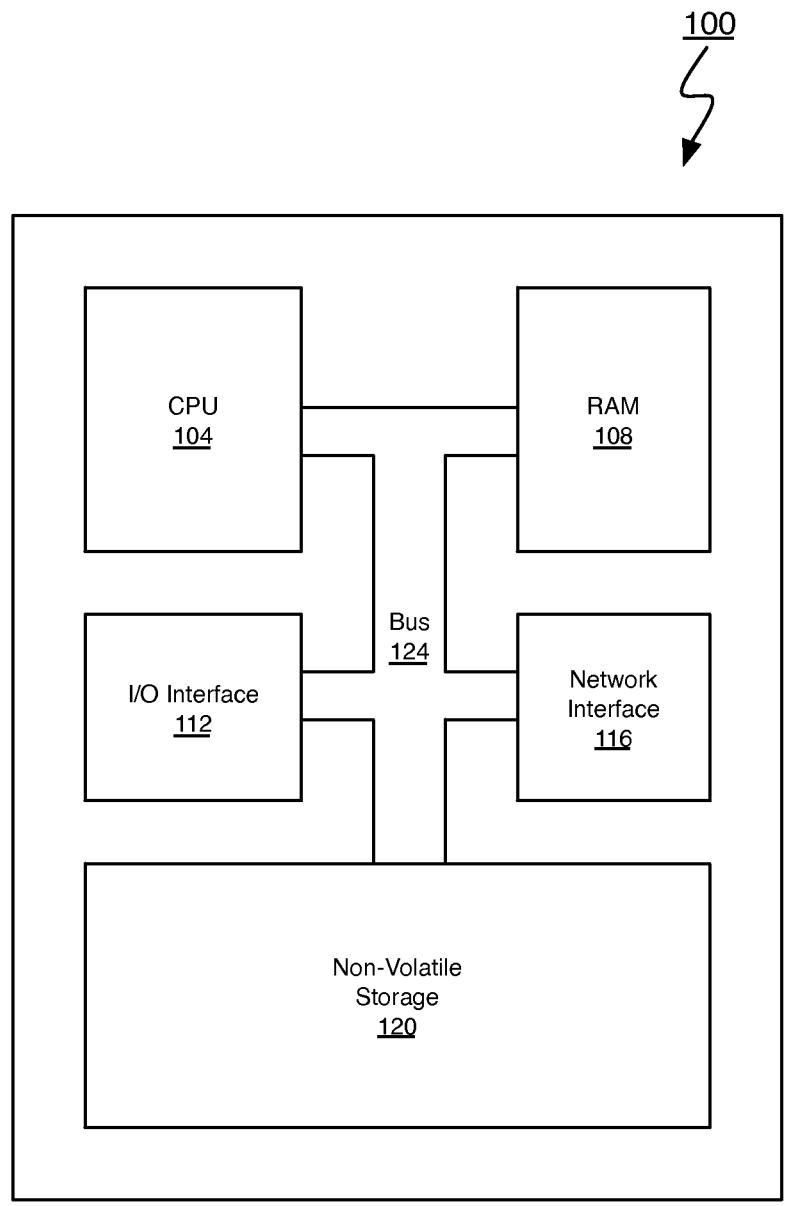
FIG. 5 shows a schematic diagram of the data-sharing server computer system of FIG. 4.

FIG. 5 is a high-level schematic diagram of the data-sharing server computer system 100 of FIG. 4. As shown, the data-sharing server computer system 100 has a number of physical and logical components, including a central processing unit ("CPU") 104, random access memory ("RAM") 108, an input/output ("I/O") interface 112, a network interface 116, non-volatile storage 120, and a local bus 124 enabling the CPU 104 to communicate with the other components. The CPU 104 executes an operating system, a stateful data-sharing service and possibly one or more software system components. RAM 108 provides relatively-responsive volatile storage to the CPU 104. The I/O interface 112 allows for input to be received from one or more devices, such as a keyboard, a mouse, etc., and outputs information to output devices, such as a display and/or speakers. The network interface 116 permits communication with other computing devices, such as tablet 20*a* and desktop computer 20*b*. Non-volatile storage 120 stores the operating system and programs, including computer-executable instructions and artefacts for implementing the stateful data-sharing service and the software system components, if any. The data-sharing server computer system 100 may also use part of the non-volatile storage 120 as a temporary swap file that augments the volatile storage provided by RAM 108. During operation of the data-sharing server computer system 100, the operating system, the programs and the artefacts may be retrieved from the non-volatile storage 120 and placed in volatile storage to facilitate execution. Data shared by software systems is maintained by the stateful data-sharing service in volatile storage.

Figure 6:
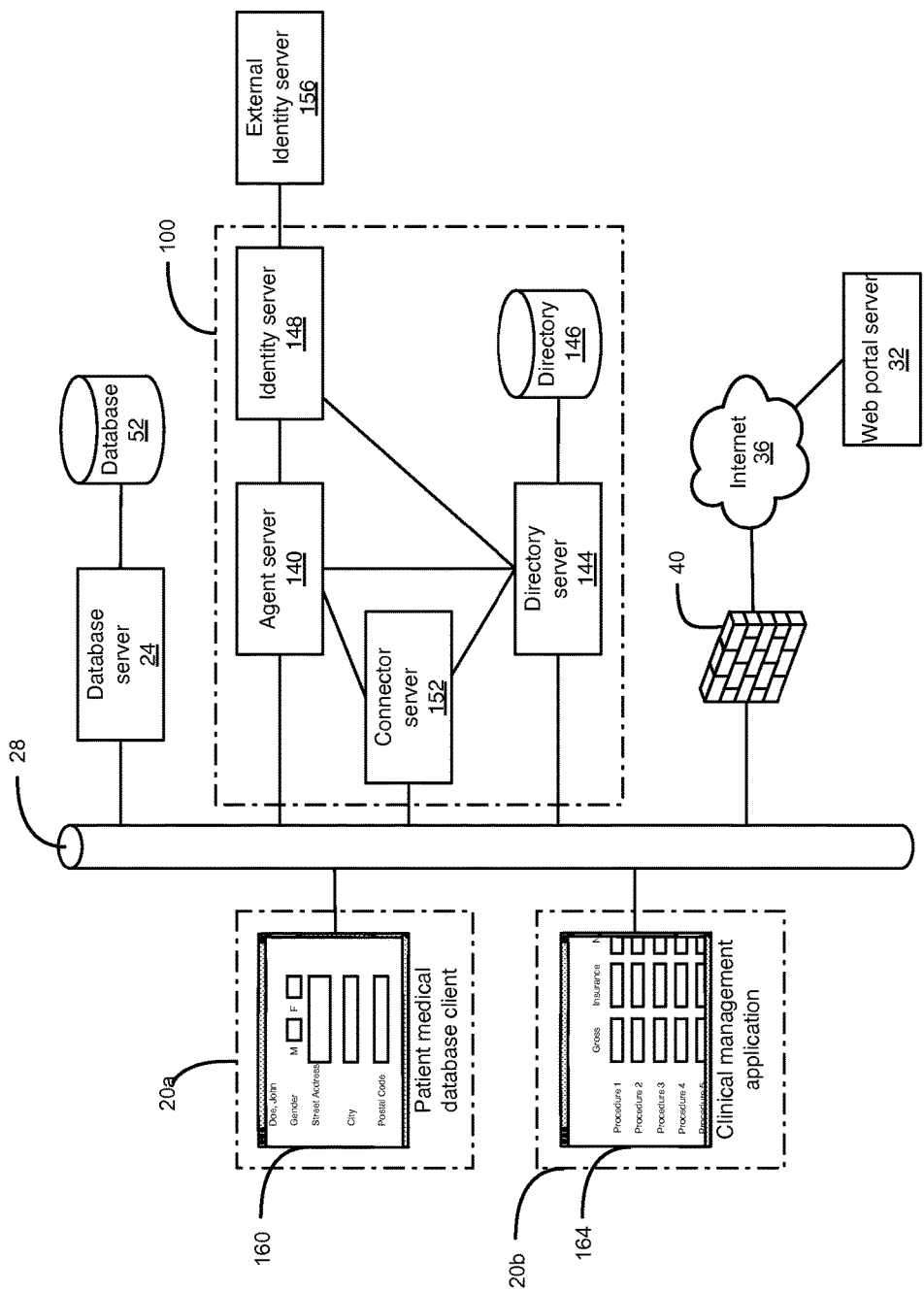
FIG. 6 shows software systems similar to those of FIG. 2 and various components of a stateful data-sharing service executing on the hardware of FIG. 4.

Referring now to FIGS. 4 and 6, various logical and physical components of the system are shown and will be described. The stateful data-sharing service executing on the data-sharing server computer system 100 for managing collaborations includes various software modules, including an agent server 140, a directory server 144 that manages a directory 146, an identity server 148, and a connector server 152. The agent server 140 orchestrates the grouping of software systems into collaborations, and the exchange of data between the software systems via the collaboration. The directory 146 managed by the directory server 144 stores static artefacts used by the agent server 140 to create and manage collaborations. The identity server 148 manages user identities in the stateful data-sharing service, and can communicate with an external identity server 156 to retrieve authorization information for users via standards, such as Lightweight Directory Access Protocol ("LDAP"). The connector server 152 executes various "connectors". Some connectors communicate with various resource types, such as relational databases or Web services. Other connectors are helper applications that perform simple functions like unit conversions.

Figure 2:
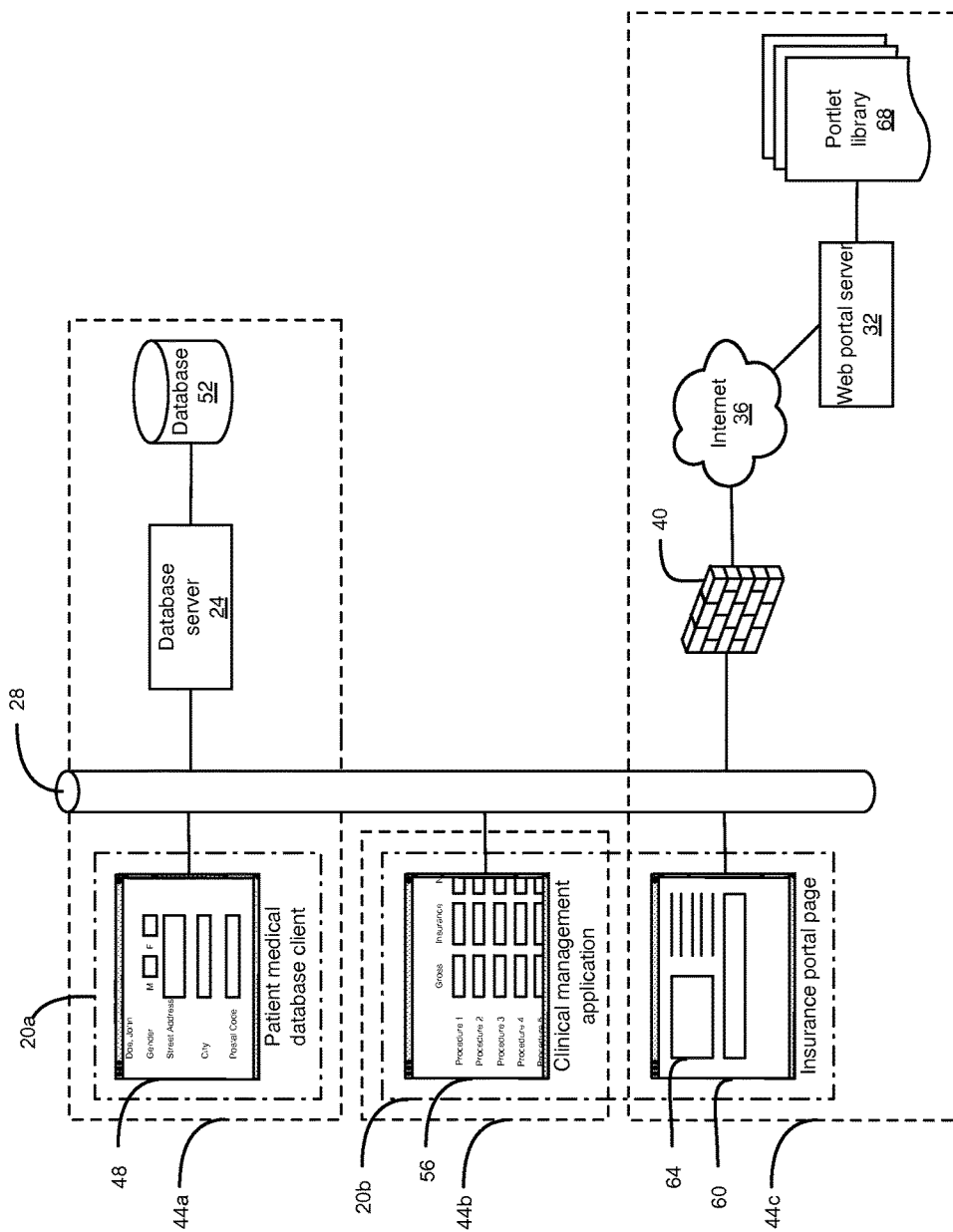
FIG. 2 shows various software systems executing on the hardware shown in FIG. 1.
Figure 3:
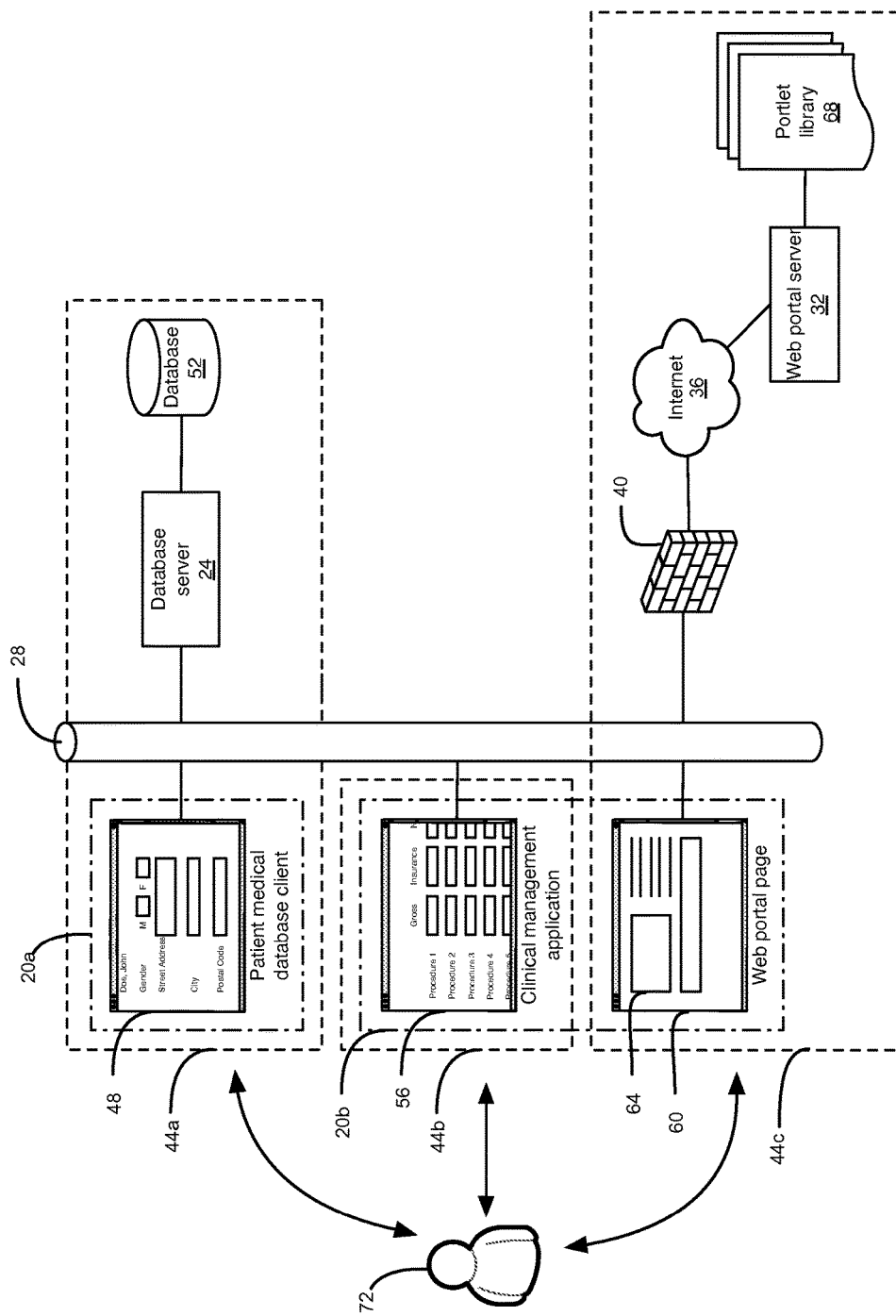
FIG. 3 shows the user interaction with the software systems of FIG. 2 to perform the task.

A set of representative software systems are shown as at least partially executing on the tablet 20*a* and the desktop computer 20*b*. The resources provided by the software systems shown generally match those of the software systems in FIG. 2.

In particular, a first software system includes a patient medical database client 160 executing on the tablet 20*a* in communication with the database server 24 to provide access to data in the patient medical database 52 managed by the database server 24. The patient medical database client 160 is similar to the patient medical database client 48 shown in FIG. 2, except that it has been customized to communicate with the agent server 140 in order to participate in collaborations.

A second software system includes the clinical management application 164 for scheduling patient consultations and procedures, generating invoices for patient visits for each patient and recording other accounting information. The clinical management application 164 is similar to the clinical management application 56 of FIG. 2, except that it has been customized to communicate with the agent server 140 in order to launch collaborations and to participate in them.

A third software system includes a proxy connector participant executed by the agent server 140 in communication with a Web connector executed by the connector server 152. The Web connector uses information received from the collaboration via the proxy connector participant and from the directory server to retrieve information from the Web portal server 32 when provided information from the collaboration, and can return information received from the Web portal server 32, the insurance coverage amount(s) in this particular case, to the collaboration via the proxy connector participant.

Each collaboration relates to a task, and software systems used to complete that task are participants in that collaboration. As used hereinafter, it should be understood that "participant" refers to a software system that participates in a collaboration, or a component of a software system that participates in a collaboration on behalf of the software system. As previously noted, software systems can include one or more applications, programs, services, databases, firmware, executed scripts, middleware, sets of functionality available via web pages, etc. that share and/or receive data. It is said that the software system participates in a collaboration even when only a component thereof interacts with the agent server 140. Where such software systems have one or more components that execute on a personal computing device, such as the tablet 20a and the desktop computer 20b, one of these components typically communicates with the agent server 140 on behalf of the software system. These types of software systems are referred to as client-side participants. Client-side participants generally actively initiate communications with the agent server 140 to register in a collaboration. In contrast, server-side participants are components of software systems that are executed remotely on servers on behalf of users to perform actions and/or access data that a user would otherwise perform through a database client, Web browser, etc. Typically, server-side participants are invoked by the agent server 140 when a collaboration in which they are to participate is created.

Collaborations generally include at least one client-side participant that receives some data from a user and/or provides some data and/or feedback to the user.

In the system shown in FIG. 6, the patient medical database client 160 and the clinical management application 164 are client-side participants and the Web connector executed by the connector server 152 acts as a server-side participant in a collaboration.

The agent server 140 is responsible for managing collaborations and the participation of various software systems therein for each of a number of users that may be in the process of completing the same task, albeit for their context (s), and/or different tasks. In some cases, a user may be in the process of completing different tasks simultaneously, or even a particular task multiple times simultaneously. To safeguard against accidental access of a first user's data by a second user, the agent server 140 maintains the data shared by each user in separate user spaces. The user spaces are virtual sandboxes that ensure the information of a given user is only available to that user in the presence of their authentication. In addition, the agent server 140 manages a separate collaboration in the corresponding user space for each task that the user is pursuing.

The agent server 140 ensures that the participants share data according to an established set of rules. For example, the agent server 140 ensures that each data item value shared by a participant can be associated with a share declaration that includes a semantic description so that its semantics can always be determined. Semantic descriptions allow the agent server 140 to define and then process non-explicit relationships between the data items shared by software systems and data items requested by other software systems using ontologies. Semantics and ontologies enable, for example, two different properties like "YearsOld" and "Age" to be equated; even something this simple can require extensive rework without semantic descriptions, especially over a large number of software systems. These declarative semantics enable the software systems to declare the data items they share values for and the data items for which they would like to receive, or "consume", values in a manner that is independent of their internal representation, and allow them to be unambiguously identified. The use of semantics and ontologies allows the agent server 140 to properly determine the relationships between data items and software systems without point-to-point connections established by the software systems themselves or an external integration system.

The agent server 140 includes a query evaluator that evaluates whether there is a change in the state of consume requests registered by software systems. Consume requests are akin to standing queries for sets of one or more data item values as they become available or are updated. The state of a consume request is determined by whether or not the consume request is satisfied and, if satisfied, the data item values that satisfied it. A consume request is deemed satisfied when values are available for each data item in the set specified by the consume request. Thus, the query evaluator determines that there is a change in the state of a consume request if one or more new values are shared and the consume request is satisfied, or if the consume request becomes unsatisfied as a result of one or more values being removed from the collaboration. Consume requests are defined such that software systems are not notified of new shared values unless values are available for each of the set of data items specified in the consume request. In this manner, control is afforded to the software systems as to when notifications occur.

The data items for which values are desired are described semantically in the consume requests. The query evaluator includes a reasoner module that semantically resolves the data requested in the consume requests to data items for which values have been received, if possible, via their semantic descriptions using ontologies. The reasoner module does this by computing inferences between the semantic description of the requested data and the semantic description of the data items shared in the collaboration. It will be appreciated that, in some cases, the query evaluator may be unable to resolve the requested data to data items in the collaboration. For example, the requested data may not yet be available as a particular software system type having data items to which the requested data semantically resolves may not have registered yet or has not shared values for these data items yet, or the requested data may simply not match any of the data items defined in the share declarations of the participant definitions for a collaboration. The query evaluator then determines if values for the matched data items have been received by checking the collaboration instance data. The particular query evaluator implemented in this embodiment is from Jena, an open source Java framework for building semantic web applications, information about which can be found at http://jena.sourceforge.net/.

The agent server 140 manages the shared data set as it is shared by software systems and then subsequently provided to other software systems 116. The data shared in a collaboration is stored during the lifetime of the collaboration, or for some shorter period, such as the lifetime of a participant, a set period of time, etc. The shared data is stored in a non-permanent manner in volatile storage, such as in RAM 108, a temporary swap file that may be stored in non-volatile storage 120, etc. The agent server 140 does not need a database or other persistence mechanism because, by design, it does not permanently store the information it manages. By not storing the shared data permanently, greater security is afforded to the data shared.

The agent server 140 is implemented as a Java Web application deployed on the data-sharing server computer system 100. An administrative user interface of the agent server 140 enables configuration thereof, but most of its functionality is exposed as multi-user Web service API via HyperText Transfer Protocol ("HTTP") and Secure HTTP ("HTTPS") that is used during regular operation. The API provides access to collaborations and participants and supports core operations, namely:

- create a collaboration
- destroy a collaboration
- register a participant
- de-register a participant
- suspend a participant
- enable notifications for consume requests for a participant
- share information in the collaboration from a participant
- remove shared information from the context for a participant
- send notification of shared information to a participant The directory server 144 maintains information used by the agent server 140 to manage collaborations and the participation of software systems in those collaborations, and by the connector server 152 to configure connectors.

Figure 7:
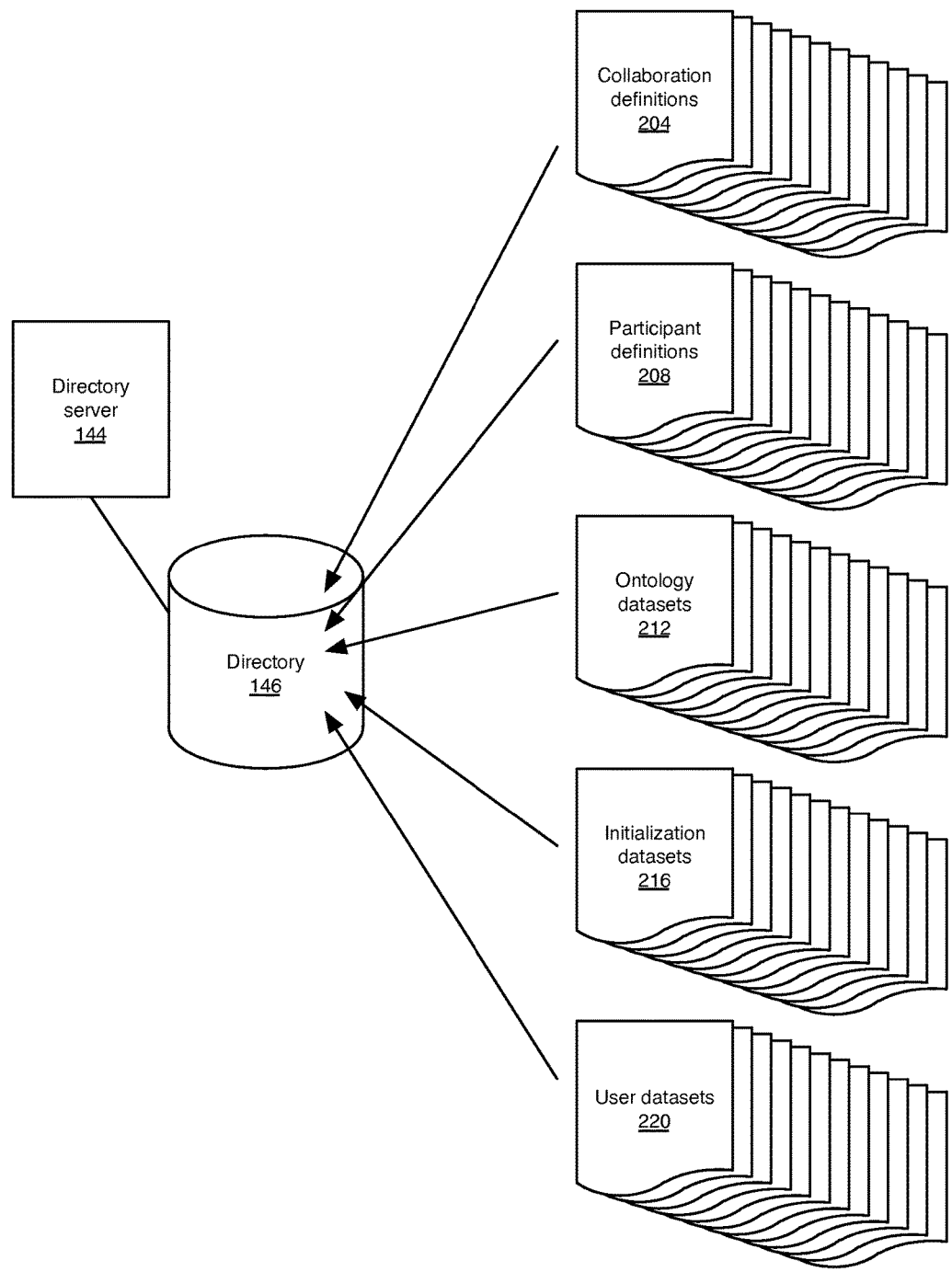
FIG. 7 shows the directory server of the data-sharing server computer system of FIG. 6, together with various artefacts stored in a directory it maintains.

Referring now to FIGS. 6 and 7, the directory server 144 is shown managing the directory 146. The directory 146 stores various static artefacts, including collaboration definitions 204, participant definitions 208, ontology datasets 212, initialization datasets 216 and user datasets 220. The collaboration definitions 204 and the participant definitions 208 represent collaboration and participant policy statements regarding what can happen in a collaboration and what each participant can do in a collaboration respectively.

Collaboration definitions 204 are used by the agent server 140 to create and manage collaborations. Each collaboration definition 204 delineates a pre-defined type of collaboration, and is set out in Terse RDF Triple Language ("Turtle"); that is, a serialization format (the standard for which the latest version can be found at http://www.w3.org/TeamSubmission/turtle/) for Resource Description Framework ("RDF") graphs. RDF is a metadata data model that is defined via a family of World Wide Web Consortium ("W3C") specifications for modelling information conceptually that can be found at http://www.w3.org/standards/techs/rdf#w3c_all. The RDF statements specify the participant definitions 208 for the types of participants allowed in a collaboration of the type defined by the collaboration definition, the initialization datasets 216 that the collaboration is to be populated with at initialization, and the ontology datasets 212 that are to be used in the collaboration.

A collaboration only has capacity for (I.e., allows participation therein by) one participant of each participant type matching the specified participant definitions 208 in the collaboration definition 204 used to create the collaboration. This ensures that two participants of the same type do not provide competing data to the collaboration. The collaboration definitions 204 are identified using a universal resource identifier ("URI") and, likewise, refer to the participant definitions 208, the ontology datasets 212, and the initialization datasets 216 via URIs. The URIs are unique identifiers that identify the collaboration definitions 204, the participant definitions 208, the ontology datasets 212, and the initialization datasets 216 within a scope owned by the author of the software system, for example the domain name system ("DNS") name of the company that authored the component could be used to scope the identifier to that company with a suffix identifying the particular data item being shared.

During runtime, the agent server 140 retrieves collaboration definitions 204 from the directory server 144 and uses them to create and initialize collaborations, as will be described below.

Each participant definition 208, like the collaboration definitions 204, is specified in Turtle that includes a set of RDF statements for the participant type including participant configuration information, share declarations defining what data the participant type is allowed to share, and consume request definitions defining what data the participant type is allowed to receive when it is available and/or updated within the scope of the particular task associated with the collaboration. Thus, participant definitions 204 are like policy statements that delineate what a participant can and cannot do. Participants are loosely coupled in collaborations. For this purpose, the details of the participant configuration information, consume request definitions and share declarations as specified in each participant definition 208 are only used in the management of that particular participant by the agent server 140, and not shared with other participants of other types. Neither the participant configuration information, the consume request definitions nor the share declarations for participant types form part of the collaboration definition 204 other than by reference to the participant definition 208 that contains them. This enables participant types to be swapped in a collaboration definition 204 without worrying about any binding other than that expressed by their share declarations and consume request definitions.

As noted, each participant definition 208 has a URI. Software systems that participate in collaborations identify themselves using the URI of the corresponding participant definition 208 when registering with the agent server 140.

The participant configuration information includes a description of the participant type and other desired declarations, enabling the storage of configuration information for software systems in their corresponding participant definitions 208. The participant configuration information included in the participant definition 208 is loaded by the agent server 140 from the directory 146 via the directory server 144 when a collaboration is created. Participants can get access to the participant configuration information for their participant type by registering a consume request for it. Examples of participant configuration information include a name for the participant, a description for the participant, and a URL for a resource or other server to connect to.

The share declarations in a participant definition 208 represent the sets of data items allowed to be shared by a participant type. Each share declaration delimits and identifies a set of information that the participant type may provide to the collaboration. Each participant type can have zero to many share declarations. The share declarations provide a list of the data items to be shared, including the formal semantic definition for these data items to permit useful matching and discovery of the data items by the reasoner module of the agent server 140, as well as transformation of the data items.

Share declarations are uniquely identified by URI. Uniqueness across all the software systems enables each use of that data item identifier (i.e., the URI) to reliably identify a data item with the same characteristics. In simple terms, if software system A publishes a value for data item with a URI of http://example.com/2010/C1 and software system B wants to consume data with a semantic description matching that of the data item, it can count on the fact that the data item with the URI http://example.com/2010/C1 from software system A is the expected data.

At runtime when a participant wants to share data item values, it refers to the URI of a valid share declaration specified in the participant definition 208 corresponding to the type of the participant. This limits information shared by the participant to a subset of the information specified in the share declarations set out in the participant definition 208.

As previously noted, consume requests are akin to standing queries for sets of data item values as they become available (thus satisfying the consume requests), are updated while the consume request is satisfied, and/or are removed from the collaboration (thus causing the consume requests to become unsatisfied). In all of these cases, the state of the consume requests change. The consume request definitions specified in the participant definition 208 delimit the consume requests allowed to be registered by a participant. Each consume request definition specifies a standing query for data item values from the collaboration with sufficient semantics to enable the agent server 140 to semantically resolve the requested data item values to the values of one or more data items, when available. Each participant type can have zero to many consume request definitions. The consume request definitions in a participant definition 208 for a software system type are standing queries written in the SPARQL Protocol and RDF Query Language ("SPARQL") that is another W3C specification for querying information semantically. Consume request definitions are identified by URIs. When a participant registers with the agent server 140, it provides a list of consume request definition URIs that it wants to be notified of; those URIs should relate to a subset of the consume request definitions defined in the participant definition 208. When a participant provides the URIs of one or more consume request definitions with the participant registration request, it is said that it is providing consume requests.

Consume request definitions can be defined for information from the participant definition 208. Consume requests derived from such consume request definitions are referred to as directory consume requests, as the information being requested is ultimately stored in the participant definition 208 in the directory 146. This enables configuration information used by participants of that type to be stored in the participant definition 208, thereby permitting its central management and removing the need to recode participant types for configuration changes. A participant type can be designed to register a directory consume request for configuration information, and then use the configuration information once received from the agent server 140, enabling a participant to be reconfigured as needed via changes to the configuration information in the participant definition 208. Of note is that changes to the configuration information in the participant definition 208 will only be implemented in collaborations created thereafter and will not affect previously-created collaborations. In addition, to support automated discovery of allowable consume requests, participant types can be configured to register with the agent server 140 with a directory consume request for the consume request definitions from its corresponding participant definition 208, and then re-register with consume requests corresponding to all of the consume request definitions found in the participant definition 208.

These artefacts are static as they don't change based on the current context of any user. The directory 146 holds these definitions and, whenever other components of the system need access to this information, they request it from the directory server 144. The definitions can be updated in the directory 146 and immediately have the agent server 140 use the updated definitions for new collaborations.

Ontology datasets 212 provide information about data items and how they are interrelated. The ontology information from the ontology datasets 212 extends the semantics of the participant share declarations and consume request definitions by stating relations between the semantic descriptions of the data items. Using these relations, the reasoner module of the agent server 140 can semantically resolve information requested in consume requests to data item values shared in the collaboration despite mismatches in the literal identifiers of the data items in the consume request definitions and the share declarations of the various participants.

Initialization datasets 216 are also specified in Turtle and include a set of RDF statements for data that can be used to populate a collaboration at initialization. The data can include, for example, days of the week, months of the year, number of days in each month, provinces and states, etc.

The directory server 144 can store user-specific information, like the user's name and login credentials, on behalf of the user for resources that are accessed by a participant during a collaboration in user datasets 220. These resources can be Web pages, databases, services, etc. The agent server 140 collects login credentials for each site and system from interactions of the user with the site via a participant and stores them in the user dataset 220 maintained for the particular user; that is, the user datasets 220 are associated with identities of the users. The user datasets 220 may also be proactively populated with these login credentials. The user datasets 220 are not referenced by any collaboration definitions 204. Instead, the user dataset 220 corresponding with the identity of the user is retrieved by the agent server 140 from the directory server 144 when creating a collaboration for a user based on user identity available from the user's authentication token.

The directory server 144 has a minimal administrative user interface for facilitating access to and management of the artefacts, but most of the capability is exposed as a HTTP and HTTPS API that affords flexibility in its location. The API provides access to the artefacts and supports operations like create, update and delete, as well as more complex logical operations like adding a participant type to a collaboration definition.

The identity server 148 acts as an identity gateway and may manage the identity of users in the system, including any roles that the users have. These identities are used by the agent server 140, the directory server 144 and the connector server 152. The agent server 140 reviews the roles the user has, as provided by the identity server 148, to determine if the user is authorized to launch certain collaborations in accordance with configuration information in the directory server 144.

There are a number of ways in which software systems can identify themselves with a user. Software systems that execute at least partially on a user's personal computing device can be configured with user credentials, can retrieve these user credentials from another location or directory, or can obtain them from the user as part of the initialization process. When one software system provides the user credentials to the agent server 140, the agent server 140 relays them to the identity server 148, which generates and returns a user token associated with the identity of the user to the software system to the agent server 140 if the user is authenticated. The agent server 140 provides the user token to the software system, which can then share this user token with other software systems on the personal computing device. Alternatively, other software systems can be configured with the same user credentials and use the same process to receive a user token corresponding to the same identity. The software systems of the stateful data-sharing service can then use these user tokens to assert the identity of the user with various components of the stateful data-sharing service.

The connector server 152 executes "connectors" that provide access to resources. Each connector is a generally stateless service that provides functionality to interact with a particular resource type, such as an SQL database or a REST server, or to perform a particular type of translation. Connectors are interacted with via server-side participants known as proxy connector participants. Proxy connector participants are instantiated and registered in a collaboration by the agent server 140 when the proxy connector participant is identified as a participant in the collaboration definition 204. When a consume request is satisfied for a proxy connector participant, the agent server 140 notifies the proxy connector participant with the following information:

the user token;
a participant token generated by the agent server 140 that uniquely identifies the connector participant;
the participant definition URI;
the URI of the consume request definition that was satisfied;
the data item values satisfying the consume request; and
the transaction ID, if any.

In response, the proxy connector participant passes this information, except for the participant token and the transaction ID, to the appropriate connector server 152. The connector does not need the participant token as it does not need to know which collaboration it is participating in or for what transaction, and merely performs the action requested by the proxy connector participant as long as the identity associated with the user token has the appropriate rights to do so.

Upon receiving the information from the proxy connector participant, the connector server 152 requests the consume request definition corresponding to the participant URI and consume request URI from the directory server 144. The consume request definitions include the URL for the resource to be connected to, the syntax of the message to be sent to the resource, and any required parameters for such communications. In many cases, consume request definitions for proxy connector participants involve retrieving data from a resource. For example, data item values from a collaboration can be used to generate a structured query language ("SQL") query to a database that returns one or more values. In such cases, a share declaration associated with the consume request definition in the participant definition 208 is returned by the directory server 144 with the consume request definition.

The connector confirms that it has the right to perform the requested action on behalf of the identity associated with the user token and then performs the requested action. If there is an associated share declaration, the connector provides the data item values for the share declaration, together with the share declaration URI, to the proxy connector participant for sharing with the collaboration. Upon providing any results back to the proxy connector participant, the connector server 152 and the connector retain no knowledge of the data exchange; i.e., they are stateless. The proxy connector participant can then share the resulting data item values, if any, from the connector with the agent server 140 using the share declaration URI and the transaction ID, if any.

When the agent server 140 destroys a collaboration, it also destroys the proxy connector participants registered in that collaboration.

The data consumed and shared by connectors is tightly restricted by the consume request definitions and share declarations set out in the corresponding participant definitions 208. Thus, the connectors will not share or consume data unless explicitly specified.

Connector types include, but are not limited to, database connectors, REpresentational State Transfer ("REST") connectors, terminal services connectors, Web connectors, content connectors, and persist connectors.

Database connectors enable the exposing of data in a database in a collaboration. In response to receiving the above-noted information from the proxy connector participant, database connectors generate and execute database queries on or writes data to the database 52 via the database server 24. In the case of a database query, database connectors return the results to the proxy connector participant that shares them with the collaboration. Thus, as new data forming part of the basis for a query is added to the collaboration, the data is passed to the database connector, which forms a query or write message sent to the database server 24, and the collaboration is further enhanced by the corresponding new query results.

REST connectors enable Web services data to be exposed in a collaboration. In response to receiving the above-noted information from the proxy connector participant, REST connectors generate and transmit HTTP Get requests to a REST server for data accessed via the REST server. After receiving data back from the REST server, REST connectors return any results to the proxy connector participant, which shares them with the collaboration. Alternately, the consume request definition may direct REST connectors to generate and transmit HTTP POST requests to a REST server to cause a change in the data maintained via the REST server.

Terminal services connectors expose terminal services data in a collaboration. In response to receiving the above-noted information from the proxy connector participant, terminal services connectors generate and transmit terminal commands to a terminal server. Any data returned by the terminal server can be returned by the terminal services connector to the collaboration via the proxy connector participant.

Web connectors enable data exchange with Web applications that are not designed to natively interact with collaborations. In response to receiving the above-noted information from the proxy connector participant, Web connectors complete a request for a Web page, either by completing a form or by generating a request for a Web page with a Universal Resource Locator ("URL") constructed using the data. The Web connector then returns data from the resultant Web page to the proxy connector participant so that it can be shared in the collaboration.

Content connectors expose file contents in a collaboration. They are used to access content from applications such as Microsoft Excel or flat file text formats. In response to receiving the above-noted information from the proxy connector participant, content connectors generate read or write requests for a data source. Where data is read by the content connector, it is passed back to the associated proxy connector participant for sharing in the collaboration.

Persist connectors enable the persistence of data from the collaboration beyond the lifetime of the collaboration where explicitly configured to do so. The agent server 140 stores data shared in a collaboration in a volatile manner to afford it security. In some scenarios, however, it can be desired to persist data across collaborations for a user. For example, it can be desirable to store an audit trail of the information available in the collaboration instance data across the lifetime of multiple collaborations. In response to receiving the above-noted information from the proxy connector participant, persist connectors store specified data persistently or retrieve data stored in RDF statements in a data store it maintains. Alternatively, this data could be stored by the persist connectors in the directory 146. The consume requests for the persist connectors are designed so that only the data that should persist beyond the lifetime of a collaboration does.

Additionally, the connector server 152 executes "transformers" that perform translations on the data. Transformers are similar to connectors and are invoked by the agent server 140 in a similar manner, but do not connect to other resources. Transformers transform data in a collaboration from one form to another. For example, transformers can perform a simple transformation on data provided by a proxy transformer participant and then provide the transformed data back to the proxy transformer participant to share in the collaboration for other participants to consume. A first example of a data transformation is the conversion of data values from one unit of measure to another. Another example of a transformation performed by transformation connectors is the reformatting of dates from one format to another.

Each connector (or transformer) and its associated proxy connector participant (or proxy transformer participant), if any, when configured using a participant definition 208, and the resource(s) and/or other server(s) it connects to form a software system that can participate in a collaboration.

The portlets contained in the portlet library 176 external of the data-sharing server computer system 100 can be custom-designed participant types that act as participants in collaborations, and communicate with other resources and/or servers, such as a Web site or a database server. Each portlet and the resource(s) and/or other server(s) it couples to forms a software system. These portlets are designed to be readily incorporated into Web portal pages.

Collaboration and Participant Life Cycles

The life cycles of collaborations and participants are intertwined. While a participant can exist without a collaboration, it neither adds value to others nor is its own data enriched. Likewise, a collaboration without participants can neither aggregate new information nor share any information that it might have previously obtained from a participant that is no longer active.

Figure 8:
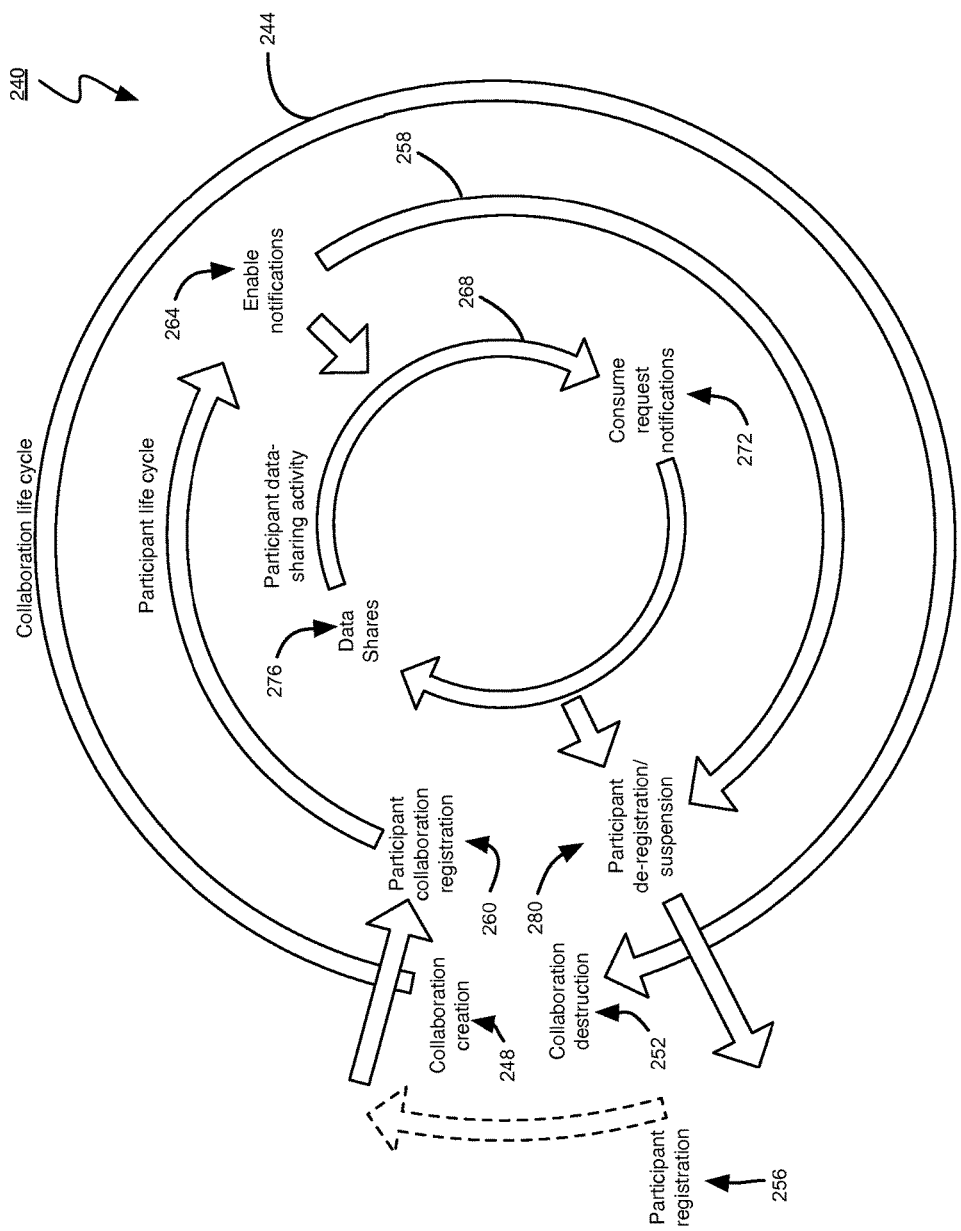
FIG. 8 shows the general lifecycle for a collaboration in the system of FIGS. 4 to 6.
Figure 9:
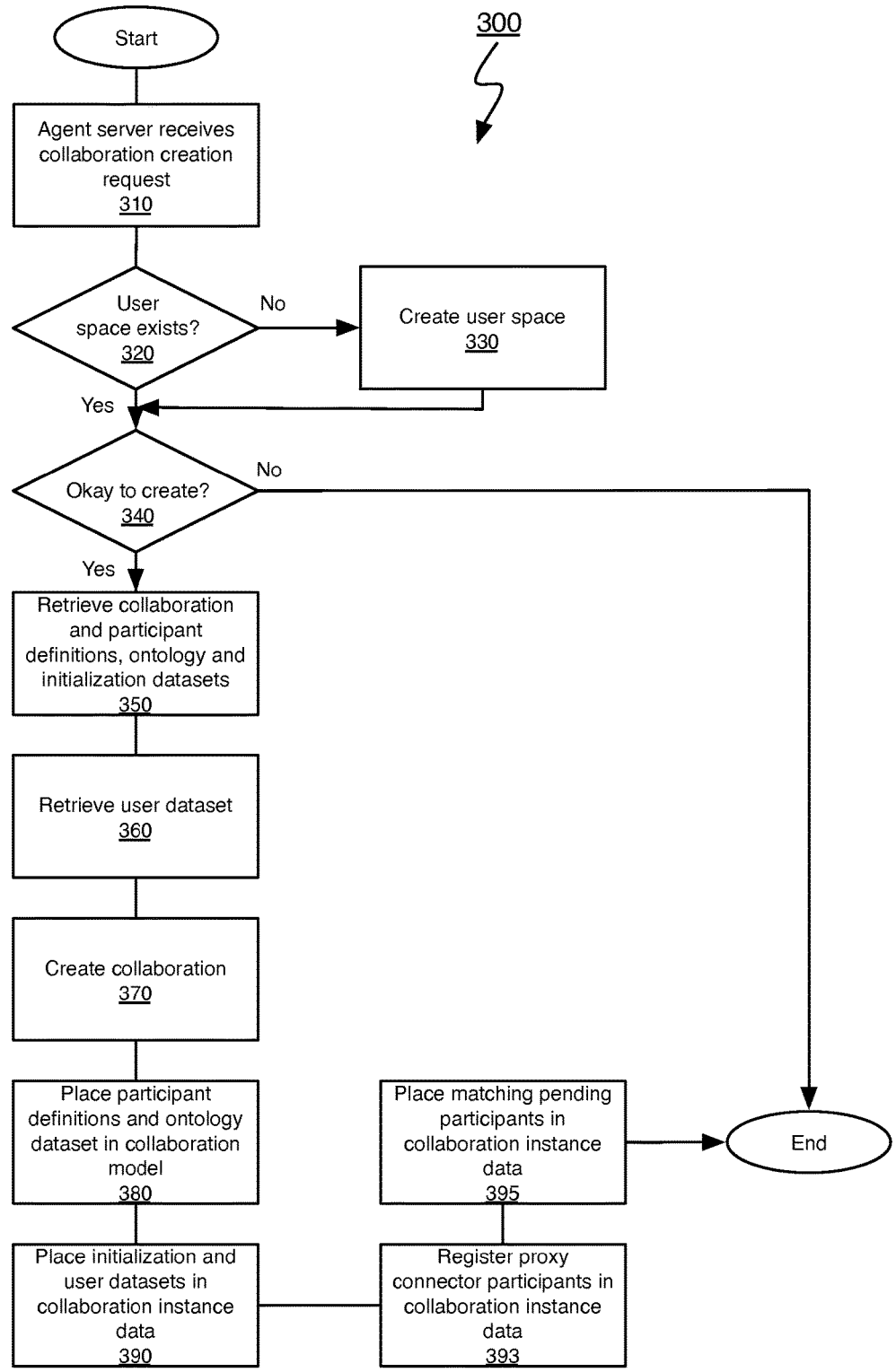
FIG. 9 is a flow chart of the general method of creating a collaboration employed by the data-sharing server computer system of FIGS. 4 to 6.

FIG. 8 shows the life cycles of collaborations and participants. A collaboration life cycle 244 is shown. Collaboration creation 248 is effected by the agent server 140 in response to receiving a collaboration creation request. As noted above, collaboration creation requests are typically generated by one of the software systems that would like to participate in a collaboration or some programming code that is related thereto. The agent server 140 creates a collaboration should it determine that certain conditions have been met. Once a collaboration is active, collaboration destruction 252 is effected by the agent server 140 as a result of any one of a set of conditions being satisfied, or upon request of a participant or other related software system component. Conditions for the lifetime of a collaboration can include, but are not limited to, the lifetime duration of a collaboration, the time elapsed since any sharing activity has occurred, the time elapsed since any data item values have been shared, the time elapsed since a particular participant has checked for new notifications, or the presence of a particular participant or participants.

If a participant registration 256 with the agent server 140 occurs prior to the availability of a collaboration that it can join, the participant is made pending until such a corresponding collaboration is created. Participant life cycles 258 within the collaboration life cycle 244 commence with a participant collaboration registration 260. As software systems configured to participate in the collaboration generate registration requests, the agent server 140 registers these participants in the collaboration. Additionally, if a participant has registered prior to the creation of the collaboration, the pending participant is registered into the collaboration by the agent server 140 when the collaboration is created. The registration requests received from the software systems include consume requests in the form of identifiers of the consume request definitions from the corresponding participant definitions 208 for the sets of data item values that the software system wishes to receive updates for. The participant may be configured to request to commence receiving notifications of updates to sets of data item values in the collaboration matching its consume request(s) via an enable notifications request 264 either immediately or at a later time. In some cases, a participant may be configured to delay receiving notifications of data item values as they become available (thus causing a change in state of its consume requests), are updated while the consume request is satisfied, and/or are removed from the collaboration (thus causing the consume requests to become unsatisfied) until the participant has completed its initialization.

Once the enable notifications request 264 from a participant has been received, the participant data-sharing activity 268 commences. When the agent server 140 processes the enable notifications request 264, it evaluates all consume requests registered for the participant to determine whether the state of a consume request has changed. If the satisfaction state of any consume request has changed, or if the values that satisfy a consume request change, the agent server 140 flags the consume request for notification as its state has changed. Additionally, when data item values are received by the agent server 140 from any participant and updated in the collaboration instance data, the agent server 140 determines which registered consume requests, if any, have states that have changed and flags these consume requests for notification. Participants poll the agent server 140 regularly for consume request notifications. When the agent server 140 receives this poll message, it replies with an identification of the registered consume requests that have undergone state changes via a consume request notification 272. Upon receiving the consume request notification 272, the participant generates a request for the data item values identified as updated in the consume request notification 272 and is provided these values by the agent server 140. If the consume request notification was triggered as a result of the consume request becoming unsatisfied, the agent server 140 provides a notice of the consume request's state to the participant instead of the values. During the course of participant data-sharing activity 268, the participant can provide data to the collaboration via data shares 276. The pattern of data shares 276 and consume request notifications 272 can vary entirely from participant to participant. Participants may be configured to only share data, to only consume data or to both share and consume data. It will be understood that the data-sharing activity of one participant can impact the pattern of consume request notifications for another participant.

The participant life cycle 258, and thus the participant data-sharing activity 268, can end in a number of manners, including the de-registration of the participant in the collaboration via a de-registration or suspension request generated by the participant, or the destruction of the collaboration. A participant can generate a de-registration request or suspension request 280 to indicate that it would like to permanently or temporarily stop participating in the collaboration. The agent server 140 receives polls from participants regularly or intermittently to check if there are updated values they would like to receive. If the agent server 140 has not received a poll from a participant within a specified period of time, it can suspend and/or de-register the participant. Where a participant has been suspended, consume request notifications 272 are halted until the participant becomes active again via a participant collaboration registration 260. During this period of participant suspension, the agent server 140 continues to determine which consume requests for the participant have undergone state changes, and flags these consume requests. Upon re-registration of the suspended participant, the agent server 140 notifies the participant of the consume requests that have undergone state changes since suspension. Where a participant has de-registered and then registers again via a participant collaboration registration 260, the agent server 140 treats the participant as if the participant never previously participated and evaluates all consume requests for the participant to determine if any have undergone state changes. After a software system has registered, it may share data in the collaboration. The data to be shared may be generated by the software system independent of data received from a collaboration as part of a new transaction, or may be generated in response to receiving data from a collaboration and form part of that existing transaction.

Collaboration Creation

The method 300 of creating a collaboration will be described with reference to FIGS. 4 to 9. This method 300 commences with the agent server 140 receiving a collaboration creation request (310). The collaboration creation request is typically generated by a software system that is configured to participate in a collaboration, but may be also generated by another related software system. This collaboration creation request includes a user token associated with the identity of the user and the URI of the collaboration definition 204 to be used to create a collaboration. In addition, a collaboration ID may optionally be provided with the collaboration creation request. The collaboration ID uniquely identifies a collaboration to enable referral to the specific collaboration in communications from the participants to the agent server 140. One or more participants may be provided with this collaboration ID prior to attempting to join a collaboration to ensure that they share data with other specific participants. Upon receiving the collaboration creation request, the agent server 140 then determines if it is already managing a user space for the user (320). The agent server 140 maintains user spaces for each user that has ever had an active collaboration or one or more active participants waiting to join a collaboration. These user spaces are tied to the identities of the users managed by the identity server 148. If the agent server 140 determines that a user space does not exist for the identity associated with the user token provided with the collaboration creation request at 320, the agent server 140 creates a user space (330).

The agent server 140 then determines if creation of the collaboration is possible (340). In order for the agent server 140 to create a collaboration, a number of conditions must be met. The directory server 144 must be responding to communications from the agent server 140. A collaboration definition 204 having the collaboration definition URI specified in the collaboration creation request must exist in the directory 146. The collaboration ID (if provided) must not already be in use for the particular user. If any of these conditions are not met, then the method 300 ends.

If, instead, the agent server 140 determines that creation of the collaboration is possible, it sends a request via HTTPS to the directory server 144 to retrieve the collaboration definition 204 identified by the collaboration definition URI specified in the collaboration creation request and referenced artefacts (350). The directory server 144 retrieves the specified collaboration definition 204 from the directory 146 and parses it to determine what participant definitions 208, ontology datasets 212, and initialization datasets 216 are referred to therein. The collaboration definition 204 specifies these artefacts by URI. The directory server 144 then retrieves each of these additional artefacts and returns the collaboration definition 204, as well as the referenced participant definitions 208, ontology datasets 212 and initialization datasets 216, back to the agent server 140. The agent server 140 then requests the user dataset 220 that contains user-specific data, such as the user's name and login credentials for services accessed by the user in interacting with various participants, from the directory server 144 (360). The directory server 144 retrieves the user dataset 220 from the directory 146 and returns it to the agent server 140.

Upon retrieving all of the artefacts and user data associated with the collaboration, the agent server 140 creates the collaboration (370). The agent server 140 maintains the collaboration in volatile storage, such as RAM 108 and/or a swap file, so that none of the information therein is stored persistently unless explicitly specified. A unique identifier for the collaboration, referred to as the collaboration ID, is generated for the collaboration by the agent server 140 if it was not provided with the collaboration creation request. The agent server 140 then places the participant definitions 208 and the ontology datasets 212 in the collaboration as a collaboration model (380). The collaboration model stores what is referred to as directory information; that is, information that is retrieved from the directory 146. The collaboration model serves as a policy description of what data the participants can and cannot share and request. Further, the ontology information from the ontology datasets 212 extends the semantics of the participant share declarations and consume request definitions, enabling the reasoner module of the agent server 140 to semantically resolve information requested in consume requests to data items shared in the collaboration. The agent server 140 generates a graph data structure definition in the collaboration model from the collaboration definition 204, and the share declarations, consume request definitions, and participant configuration information in the participant definitions 208 using the ontology datasets 212.

Once the information model for the collaboration is complete, the agent server 140 places the initialization datasets 216 and the user dataset 220 into the instance data of the collaboration (390). The instance data represents data that can change during the lifetime of a collaboration. As previously noted, the initialization datasets 216 contain parameters used within collaborations, such as the number of days in each month, the names of provinces and states, etc. The user dataset 220 contains login credentials and other user-specific information, such as a name.

Upon instantiating the collaboration model and instance data, the agent server 140 registers any proxy connector participants and proxy transformer participants in the collaboration instance data (393). If there are proxy connector participants or proxy transformer participants specified for the collaboration, as identified by the participant definitions 208 referenced in the collaboration definition 204, the agent server 140 registers the proxy connector participants and/or proxy transformer participants in the collaboration instance data.

The agent server 140 then registers any matching pending participants in the collaboration instance data (395). Participants that registered with the agent server 140 prior to the availability of a joinable collaboration with capacity and were made pending can now be registered in the newly-created collaboration if their participant definition URI is included in the collaboration definition 204 and the collaboration has capacity for a participant of that type. Upon registering any matching pending participants, the method 300 of creating a collaboration is complete.

Figure 10:
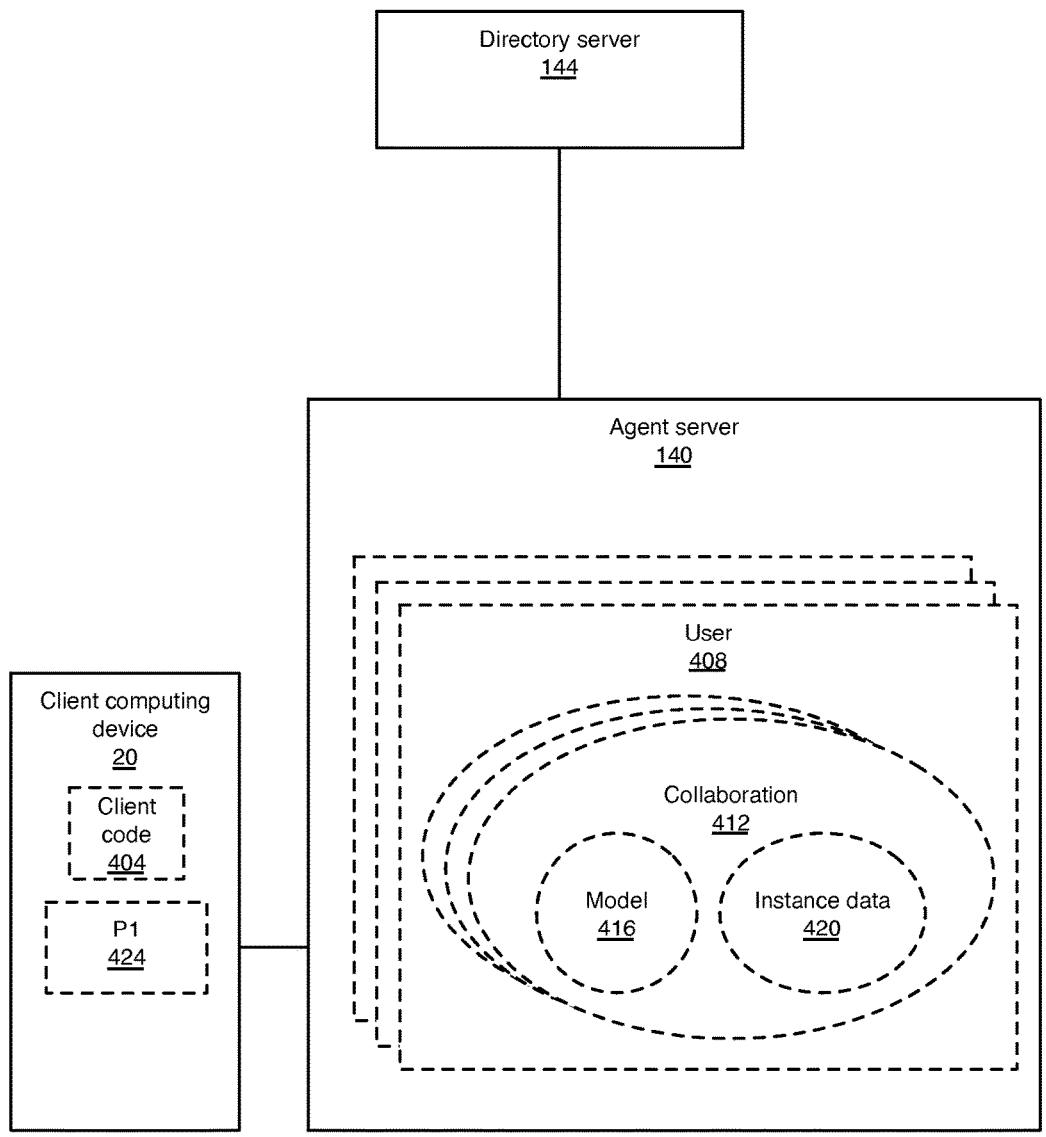
FIG. 10 illustrates the logical creation of a collaboration by the data-sharing server computer system of FIGS. 4 to 6.
Figure 11A:
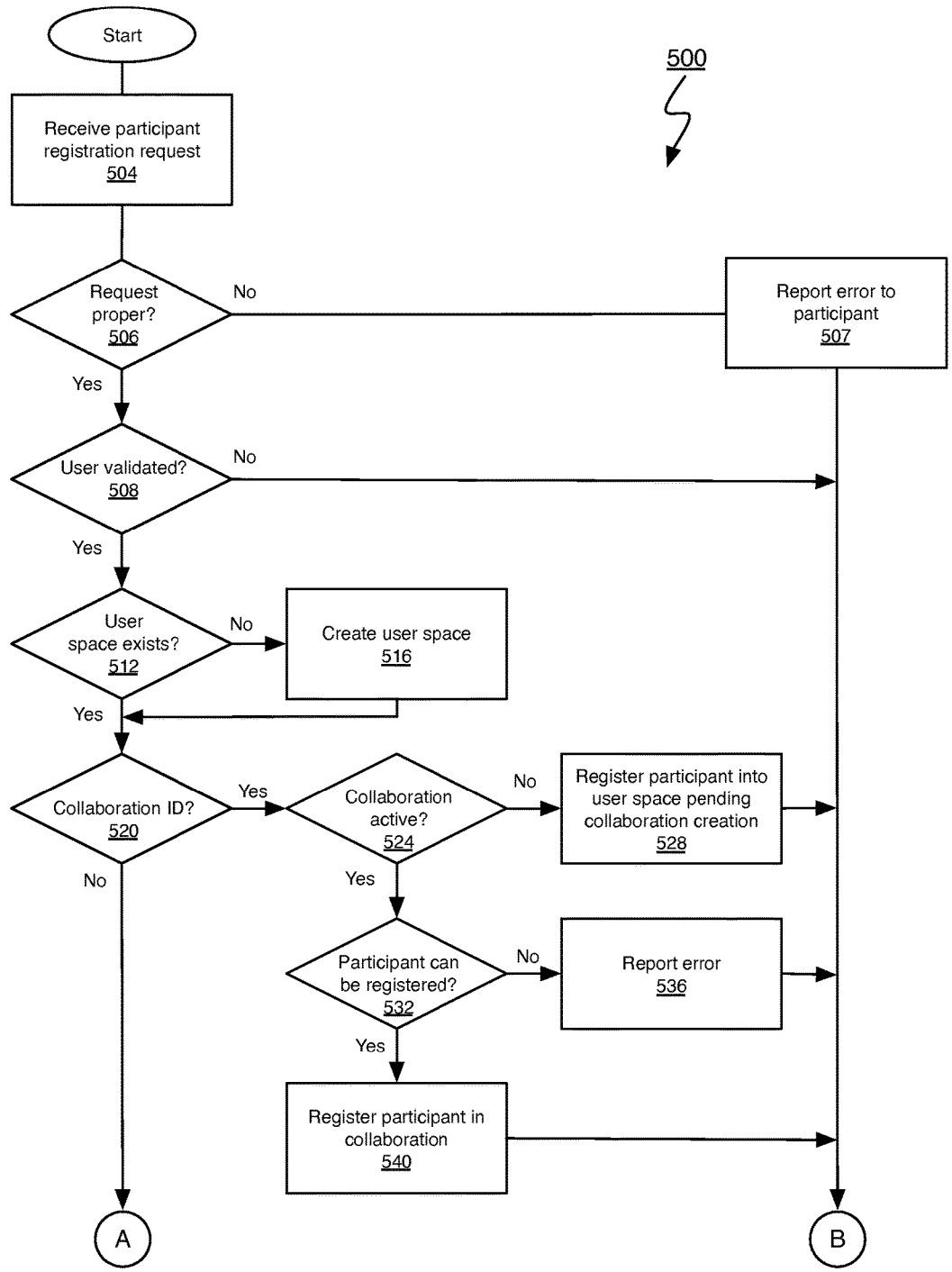
FIGS. 11A and 11B show a flow chart of the general method of registering a client-side participant by the data-sharing server computer system of FIGS. 4 to 6.
Figure 11B:
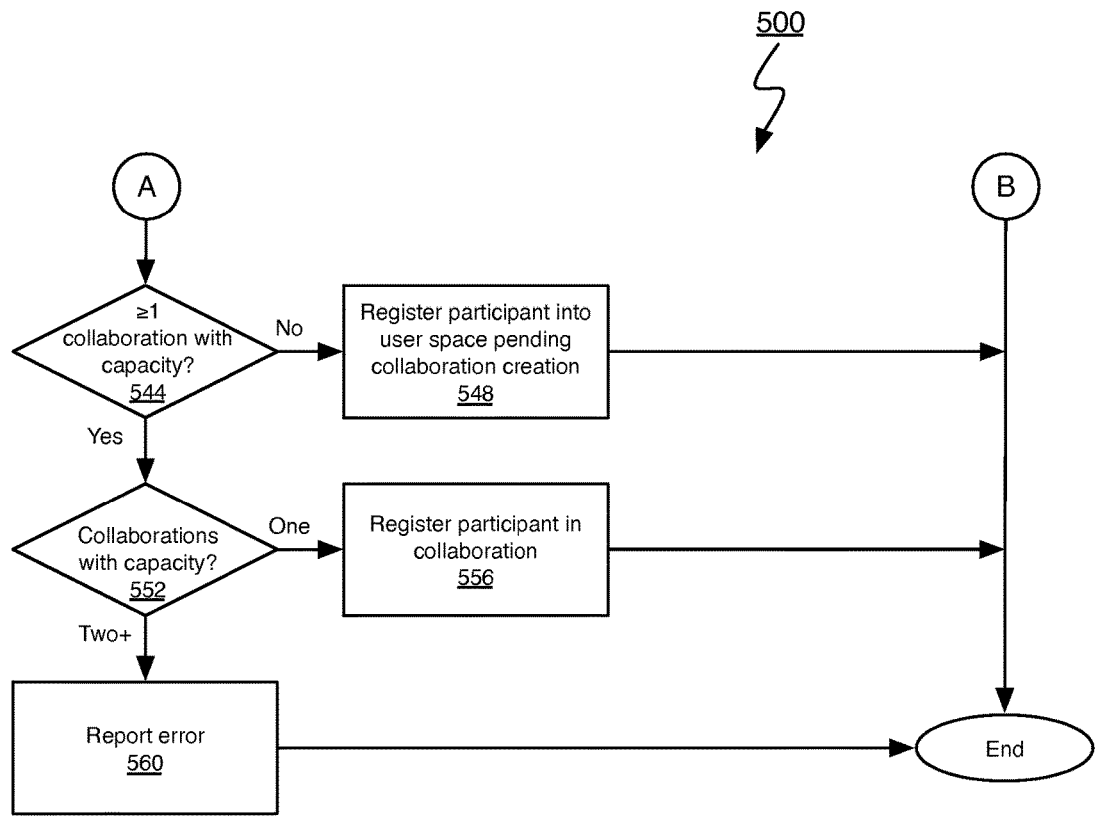

FIG. 10 illustrates client code 404 executing on a personal computing device 20 that communicates a collaboration creation request to the agent server 140 via the API made available by the agent server 140 to launch a collaboration. The agent server 140 manages a number of user spaces 408 in virtual memory spaces that are isolated from each other to avoid cross-contamination of data. Within each user space 408, the agent server 140 can maintain one or more collaborations 412 created via method 300. Each collaboration 412 contains a collaboration model 416 and instance data 420. The collaboration model 412 contains information about the participant types allowed to join the collaboration, the participant configuration information, the share declarations and consume request definitions for each participant type, and the ontology sets that are employed to resolve consume request definitions to data items in the share declarations. The instance data 420 contains a list of currently registered participants, initialization data, user data such as name and login credentials, and any data item values shared by any participant during the life of the collaboration.

The instance data 420 is maintained internally and includes a rich semantic model based on RDF triples using the collaboration model 416 and any associated ontology. Additionally, participants registered in the collaboration 412, as well as their consume requests, are registered in the instance data 420.

Client-Side Participant Registration

The method 500 of registering client-side participants by the agent server 140 will now be described with reference to FIGS. 4 to 11A and 11B. Client-side participants are generally initialized on a personal computing device and attempt to register with the agent server 140. Server-side participants are, instead, invoked by the agent server 140 as previously described.

The method 500 commences with the receipt of a participant registration request (504). When a software system component that acts as a participant is launched, it attempts to register with the agent server 140 by generating a participant registration request. The participant registration request includes:

the user token;
the URI of the participant definition 208 corresponding to the participant requesting registration;
the URI of any consume request definitions listed in the participant definition identifying what sets of data items the participant would like to receive when the state of the consume request changes; and
optionally, a collaboration ID identifying a specific instance of the collaboration that the participant wishes to join.

Participants are configured with knowledge of the corresponding participant definition URI. The consume requests provided by the participant in the participant registration request, as specified by the consume request definition URIs, should be subsets of the consume request definitions set out in the corresponding participant definition 208. While the participant definition 208 delineates what data items participants of that type are allowed to share and consume, the participants may actually be configured to share and/or consume a subset of the data items that it is permitted to share and/or consume. The collaboration ID optionally provided with the participant registration request specifies a particular collaboration that the participant is configured to be registered in.

Upon receipt of the participant registration request, the agent server 140 determines if the request is proper (506). If the agent server 140 determines that the participant definition URI provided in the participant registration request does not correspond with a participant definition 208 in the directory 146, the agent server 140 determines that the participant registration request is improper. Further, if the agent server 140 determines that the consume request definition URIs specified in the participant registration request do not match ones in the corresponding participant definition 208, the agent server 140 determines that the participant registration request is improper. If the agent server 140 determines that the participant registration request is improper, the participant registration request is discarded, and the agent server 140 reports an error to the participant (507), after which the method 500 ends.

Upon validating the participant registration request, the agent server 140 authenticates the user (508). The agent server 140 passes the user token it receives with the participant registration request to the identity server 148. In response, the identity server 148 either confirms or rejects the authenticity of the user to the agent server 140. If the user is not authenticated by the identity server 148 at 508, the participant registration request is discarded and the method 500 ends. If, instead, the user is authenticated at 508, the agent server 140 determines if it is managing a user space for the user (512). If the agent server 140 is not yet managing a user space on behalf of the user, the agent server 140 creates a user space for the user (516).

Once the agent server 140 has a user space for the user, the agent server 140 determines if a collaboration ID was provided with the participant registration request (520). If a collaboration ID was included in the participant registration request received at 504, the agent server 140 determines if it is managing an active collaboration with that collaboration ID (524). If the agent server 140 determines that it is not actively managing a collaboration with that collaboration ID, the agent server 140 generates a participant ID for the participant and registers the participant ID, its participant definition, and the consume requests received with its participant registration request in the user space pending the creation of a collaboration with the specified collaboration ID (528), after which the method 400 of registering the participant ends. The agent server 140 generates a corresponding participant token, records its association to the participant ID and forwards it to the participant.

Figure 12:
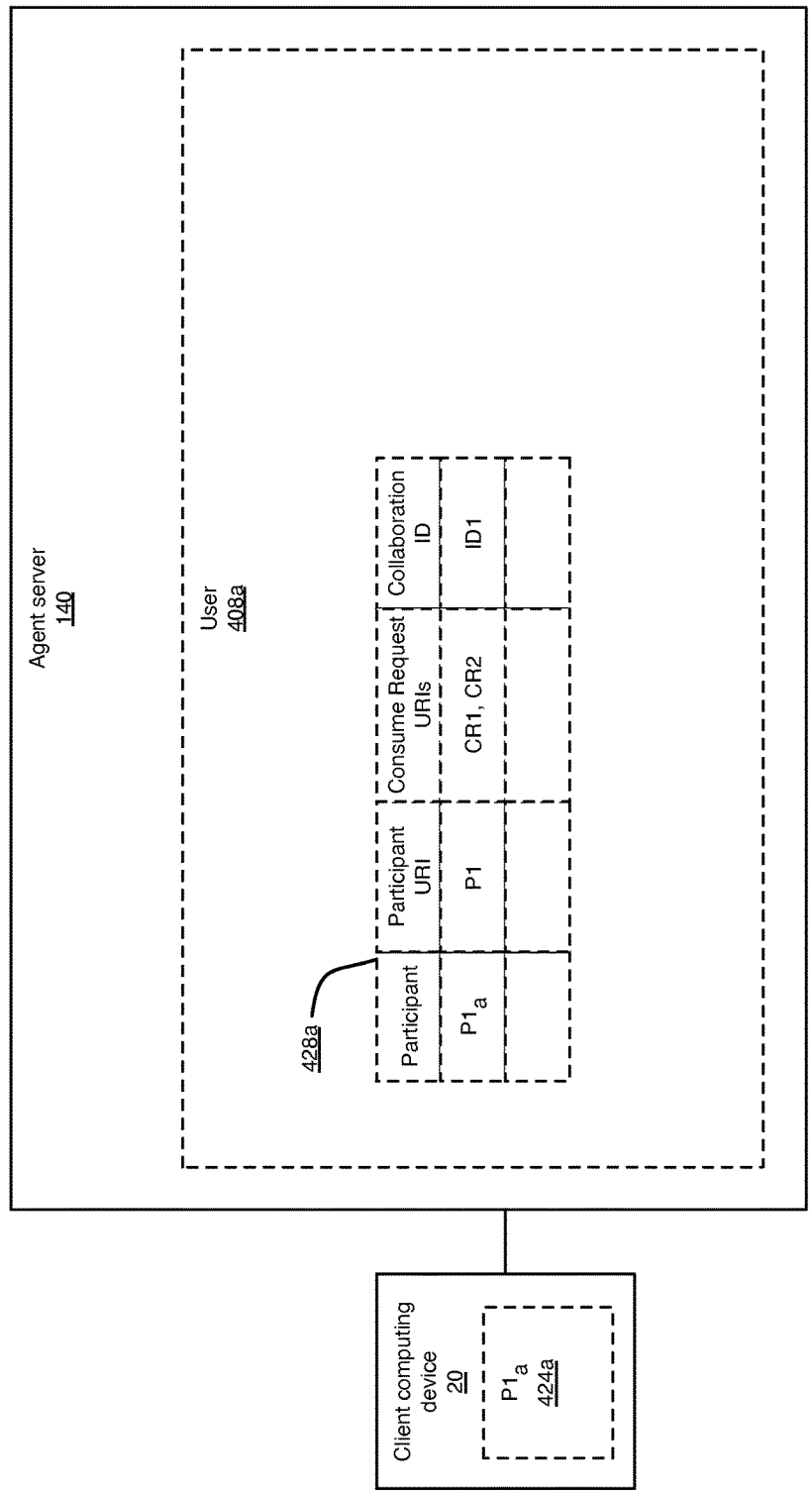
FIG. 12 shows the registration of a participant in a user space by the data-sharing server computer system of FIGS. 4 to 6 when the collaboration specified by the participant does not exist in the user space.

FIG. 12 illustrates the agent server 140 having created a user space 408a for the user of the personal computing device 20. A participant software system $P1_a$ 424a is executing on the personal computing device 20. Participant $P1_a$ 424a is an instance of participant type P1. Upon receiving a participant registration request for a collaboration having a particular collaboration ID from participant $P1_a$ 424a and having determined that a collaboration having the collaboration ID specified in the participant registration request does not yet exist, the agent server 140 creates a pending participant entry 428a for the participant P1$_a$ 424a in the user space 408a. The pending participant entry 428a includes a participant ID for the participant, the URI of the corresponding participant definition 208, the consume request URIs it is registering, and the collaboration ID of the collaboration that it would like to join.

Returning again to FIGS. 11A and 11B, if, instead, the agent server 140 determines that it is actively managing a collaboration with the particular collaboration ID specified in the participant registration request, the agent server 140 determines if the participant can be registered in the specified collaboration (532). That is, the agent server 140 determines if (a) the participant is of a participant type permitted to be registered in the collaboration; and (b) if the participant is permitted to be registered therein, whether the specified collaboration has capacity for that particular participant type. A participant can be permitted to be registered in a collaboration if the corresponding collaboration definition (instantiated in the collaboration model) includes the URI for the participant definition 208 corresponding to the participant. As only one participant of each participant type specified by the participant definitions 208 identified in the collaboration definition 204 is permitted in a collaboration, the agent server 140 ensures that there is capacity (i.e., a vacant slot) for the participant in the collaboration. If the participant is not permitted to be registered in the collaboration because the collaboration does not permit that particular participant type to register, or if the specified collaboration does not have capacity for the participant (that is, if a participant of the same participant type has already been registered in the collaboration), the agent server 140 reports an error (536), after which the method 500 of registering the participant ends.

Figure 13:
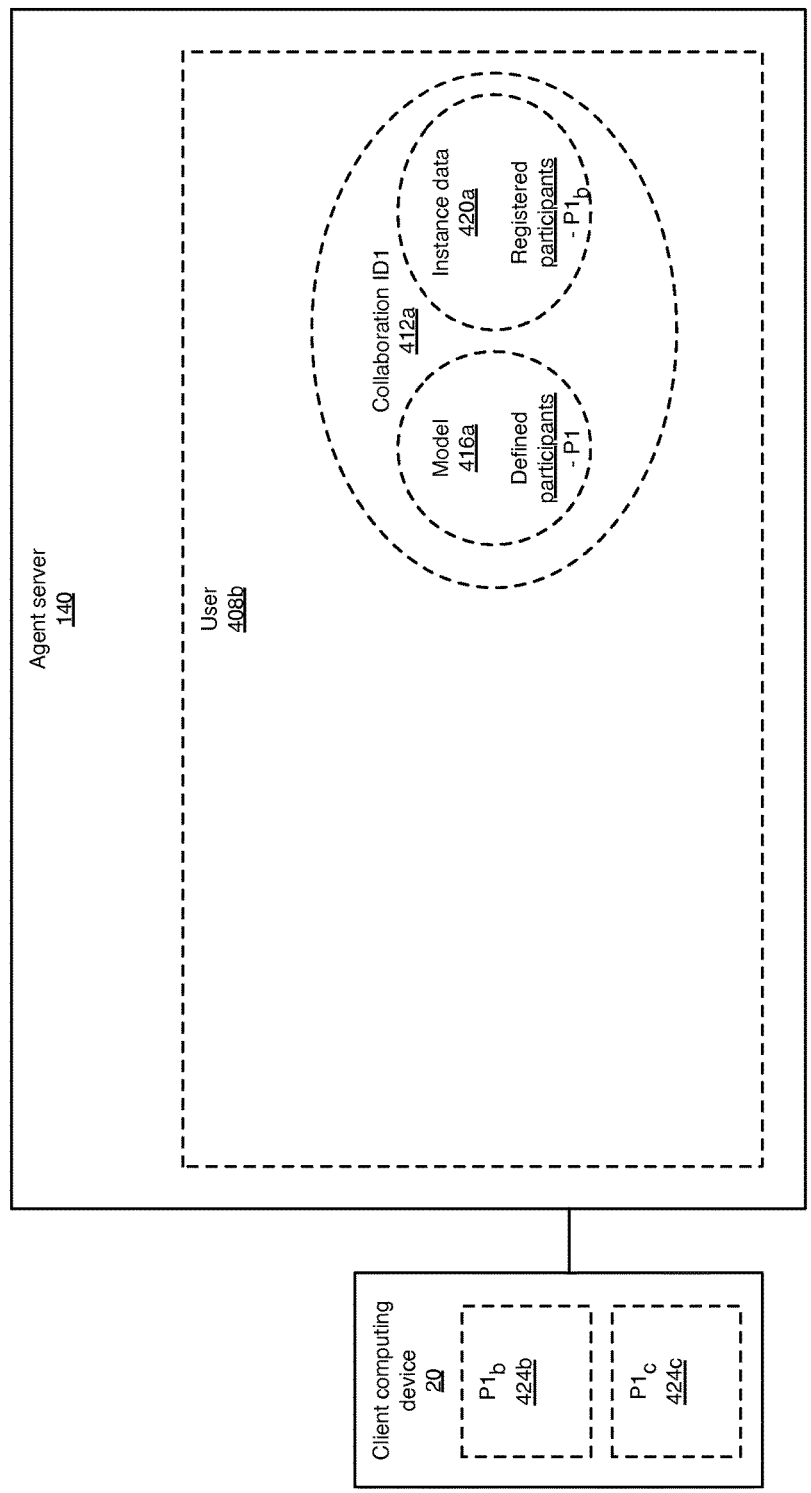
FIG. 13 shows a single collaboration managed in a user space by the data-sharing server computer system of FIGS. 4 to 6 that does not have capacity for a new participant of type P1.

FIG. 13 illustrates a circumstance where the personal computing device 20 executes two separate participants P1$_b$ 424b and P1$_c$ 424c of the same participant type, P1. The agent server 140 is managing a user space 408b for the user of the personal computing device 20, and a collaboration 412a within the user space 408b having a collaboration ID ID1. The model 416a of the collaboration 412a indicates that the collaboration 412a takes a participant of participant type P1. Participant P1$_b$ 424b has previously been registered in the instance data 420a of the collaboration 412a by the agent server 140. Upon receiving a participant registration request from participant P1$_c$ 424c for a collaboration having the collaboration ID ID1, the agent server 140 determines that the collaboration definition for the collaboration 412a permits the participant type P1 to be registered therein, but that the participant P1$_b$ 424b of the same type as participant P1$_c$ 424c has already been registered in the collaboration 412a that has this collaboration ID. As a result, the agent server 140 determines that the collaboration 412a has no capacity available for participant P1$_c$ 424c in. Accordingly, it generates and reports an error at 536.

Returning again to FIGS. 11A and 11B, if, instead, capacity is available for the participant in the specified collaboration, the agent server 140 registers the participant and its consume requests in the collaboration (540). The agent server 140 generates a unique participant ID for the participant, and registers the participant ID in the instance data of the collaboration. Further, the agent server 140 instantiates the consume request definitions from the collaboration model for the consume request definition URIs specified in the participant registration request. As the participant can be configured to register only a subset of the consume request definition URIs from the participant definition, not all of the consume request definitions from the participant definition in the collaboration model are necessarily instantiated in the collaboration instance data. The agent server 140 then generates a participant token and records the association between the participant token and the participant ID of the particular participant and the collaboration ID of the collaboration into which the participant has been registered. The agent server 140 returns the participant token to the participant for future use. The participant token can be re-provided by the participant to the agent server 140 with further communications to enable the agent server 140 to look up who the participant is and what collaboration the participant is participating in. Upon placing the participant in the collaboration, the method 500 ends.

Figure 14:
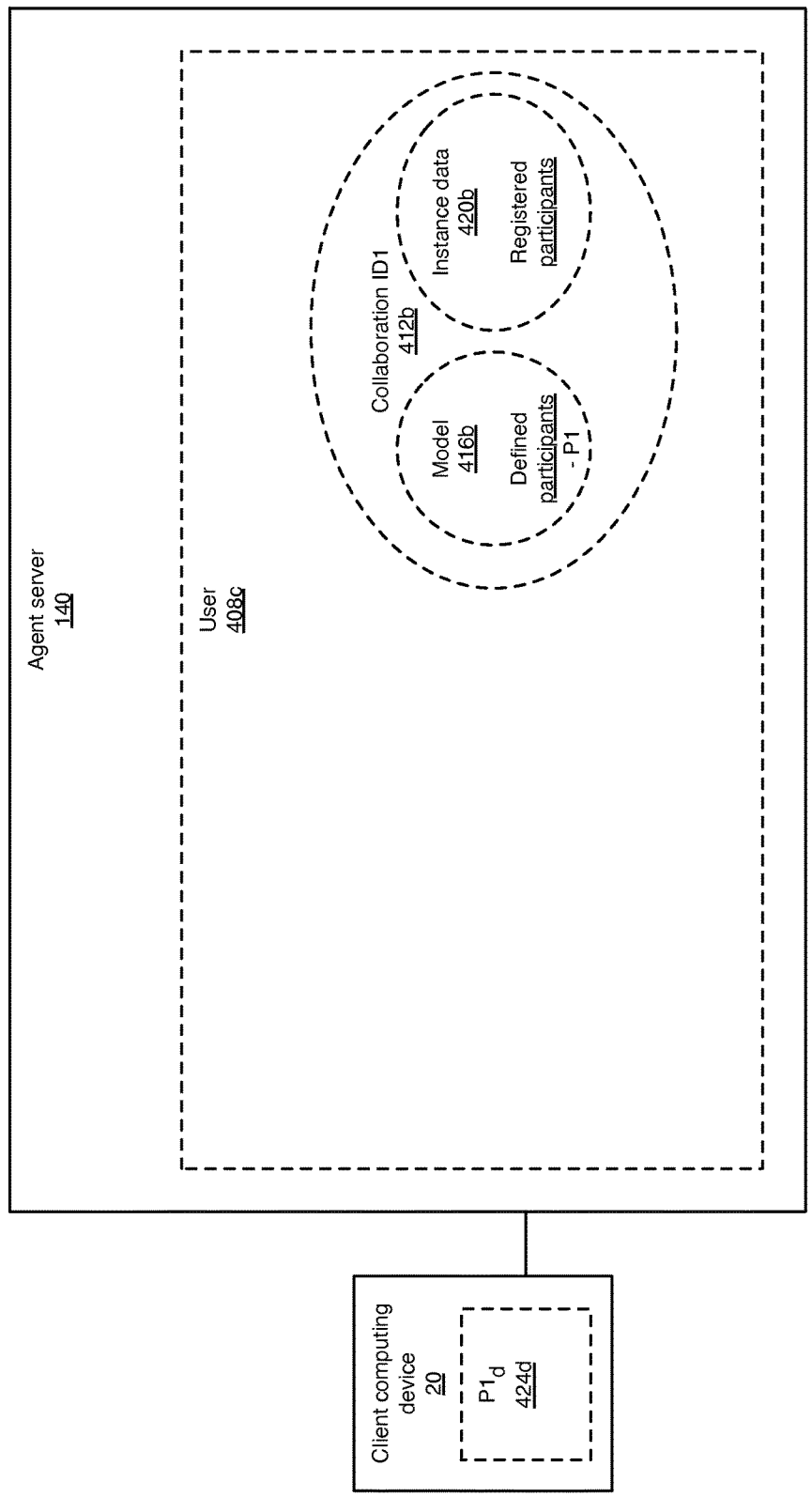
FIG. 14 shows a single collaboration managed in a user space by the data-sharing server computer system of FIGS. 4 to 6 that has capacity for a new participant of type P1.

FIG. 14 illustrates a circumstance where the personal computing device 20 executes a participant P1$_d$ 424d. The agent server 140 is managing a collaboration 412b in user space 408c for the user of the personal computing device 20. The model 416b indicates that the collaboration 412b takes a participant of participant type P1. A participant of participant type P1 is not currently registered in the collaboration 412b. Upon receiving a participant registration request from participant P1$_d$ 424d executing on the personal computing device 20 for a collaboration having the particular collaboration ID ID1, the agent server 140 determines that the collaboration definition 204 for the collaboration 412b that has that collaboration ID permits the participant type P1 to register, and that a participant of the participant type P1 is not currently registered in the collaboration 412b. Accordingly, the participant P1$_d$ 424d is eligible to be registered in the collaboration 412b.

Figure 15:
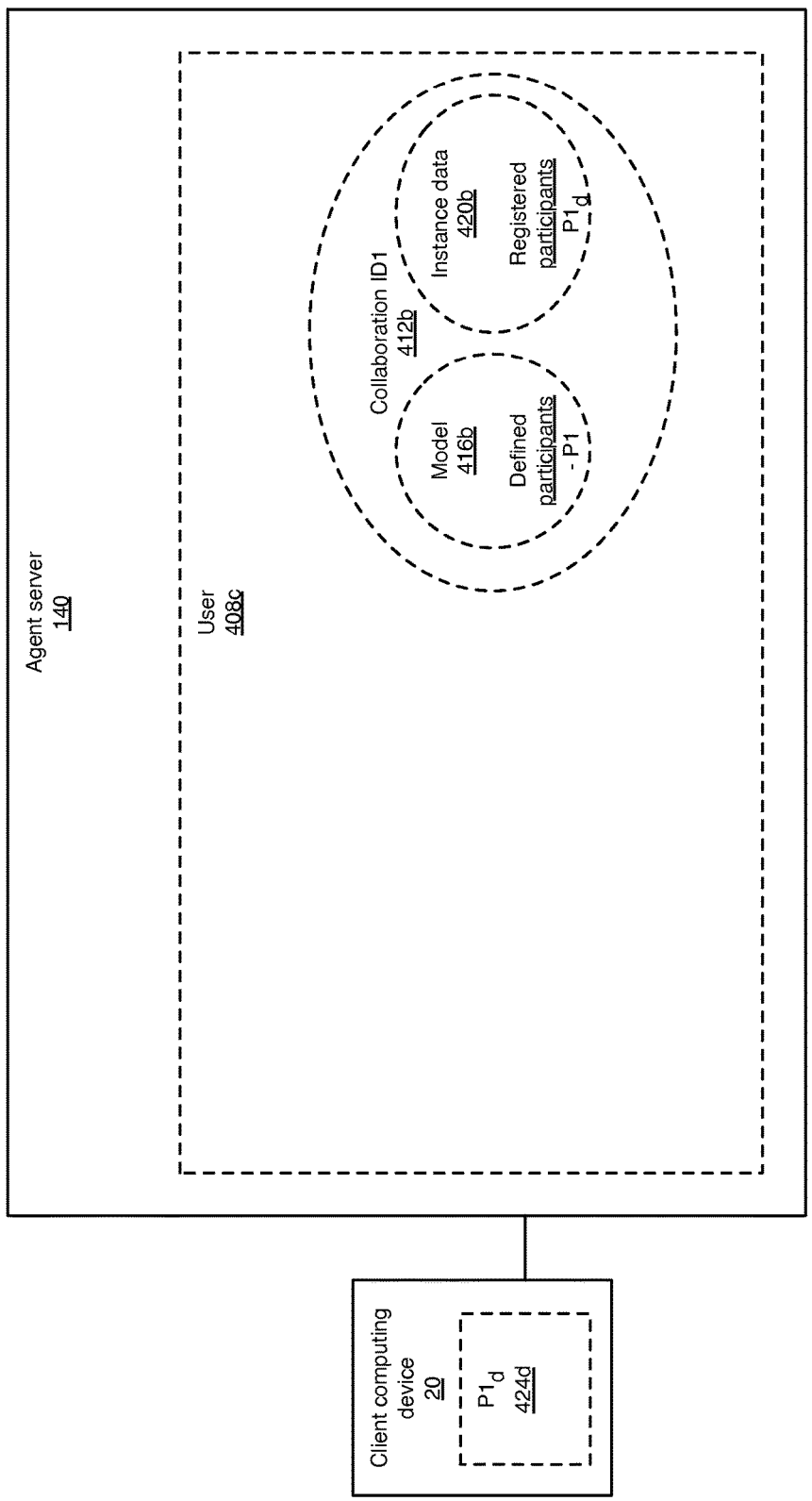
FIG. 15 shows the single collaboration of FIG. 14 after registration of a participant therein.

FIG. 15 illustrates the collaboration 412b of FIG. 14 after registration of participant P1$_d$ 424d in the instance data 420b of the collaboration 412b by the agent server 140.

Returning again to FIGS. 11A and 11B, if the agent server 140 instead determines that a collaboration ID was not included in the participant registration request received at 520, the agent server 140 determines if it is managing one or more collaborations that the participant that generated the participant registration request can be registered in and have capacity for the participant (544). As noted above, a participant can be registered in a collaboration if the corresponding collaboration definition 204 includes the URI for the participant definition 208 corresponding to the participant, and if the collaboration has capacity for that participant type. If the agent server 140 is not actively managing a collaboration that the participant is eligible to be registered in and that has capacity for the participant, the agent server 140 stores a pending participant entry in the user space pending the creation of a collaboration that the participant can be registered in (548), after which the method 500 ends. The pending participant entry includes a participant ID generated by the agent server 140 for the participant, its participant definition URI, and its consume requests, but does not include a collaboration ID as none was specified in the participant registration request.

Figure 16:
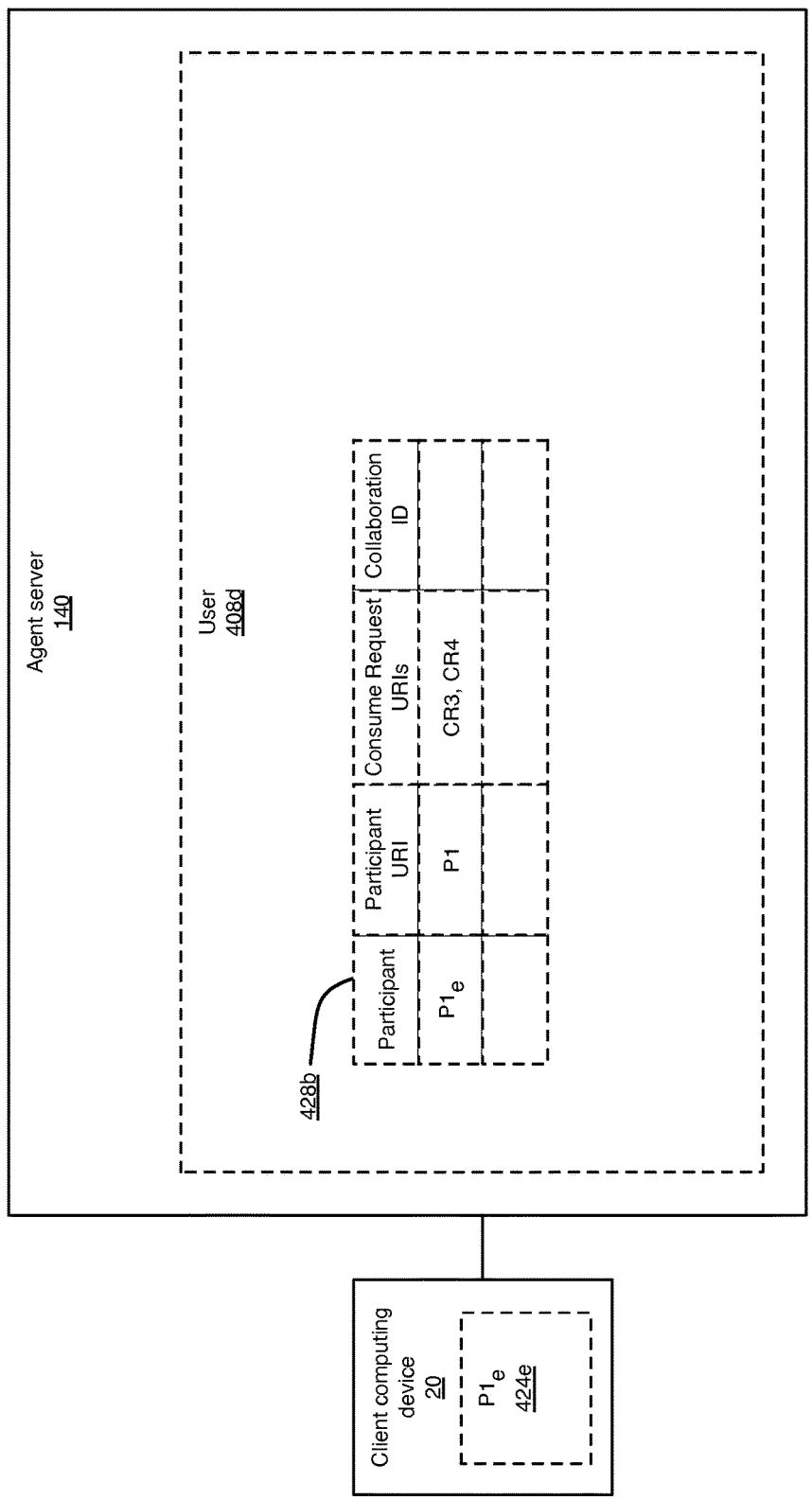
FIG. 16 shows the registration of a participant in a user space by the data-sharing server computer system of FIGS. 4 to 6 when a collaboration having capacity for the participant does not exist.

FIG. 16 illustrates a circumstance where the personal computing device 20 executes a participant P1$_e$ 424e. The agent server 140 is managing a user space 408d for the user of personal computing device 20. Upon receiving a participant registration request from participant P1$_e$ 424e without specification of a collaboration ID, the agent server 140 determines that a collaboration that the participant P1$_e$ 424e can be registered in and that has capacity for a participant of the participant type P1 of the participant P1$_e$ 424e does not exist. Accordingly, the agent server 140 creates a pending participant entry 428b for participant P1$_e$ 424e in the user space 408d.

Returning again to FIGS. 11A and 11B, if, instead, the agent server 140 is managing at least one collaboration that the participant is eligible to be registered in and that has capacity for the participant, the agent server 140 determines if one or more than one collaboration that the participant is eligible to be registered in has capacity for the participant type of the participant (552). If there is one active collaboration that the participant is eligible to be registered in that has capacity for a participant of the participant type of the participant, the agent server 140 generates a participant ID and registers the participant ID and the participant's consume requests in that collaboration (556). In addition, the agent server 140 generates a participant token that the agent server 140 has associated with the participant ID and the collaboration ID of the collaboration into which the participant has been registered, and provides the participant token to the participant for future use. The participant token can be re-provided by the participant to the agent server 140 with further communications to enable the agent server 140 to look up the identity of the participant and the collaboration in which it is participating. Upon placing the participant in the collaboration, the method 500 ends.

Figure 17:
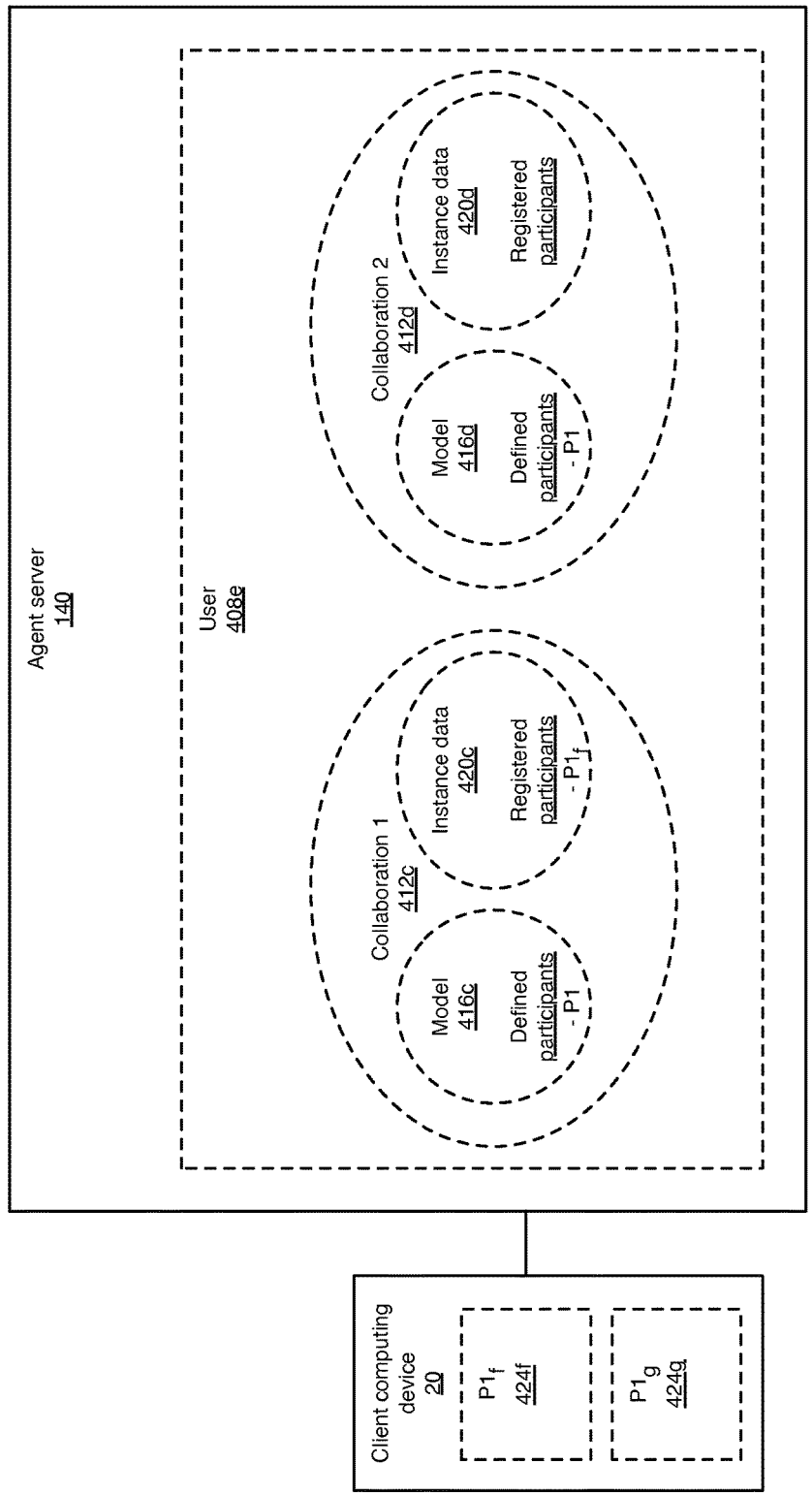
FIG. 17 shows two collaborations managed in a user space by the data-sharing server computer system of FIGS. 4 to 6, wherein one of the collaborations has capacity for a new participant of type P1.

FIG. 17 illustrates a circumstance where the personal computing device 20 executes two separate participants P1$_f$ 424f and P1$_g$ 424g of the same participant type P1. The agent server 140 is managing two separate collaborations 412c and 412d that take participants of participant type P1 in the user space 408e for the user of personal computing device 20. The models 416c, 416d of collaborations 412c, 412d respectively indicate that the collaborations 412c, 412d each take a participant of participant type P1. Participant P1$_f$ 424f has previously been registered in the instance data 420c of collaboration 412c by the agent server 140. The instance data 420d for collaboration 412d indicates that a participant of the participant type P1 is not currently registered therein. Upon receiving the participant registration request from participant P1$_g$ 424g, the agent server 140 determines that there is one and only one collaboration in which the participant P1$_g$ 424g is permitted to be registered and has capacity. As a result, the agent server 140 generates a participant ID for the participant P1$_g$ 424g and registers it in the instance data 420d of collaboration 412d, together with the consume requests of the participant P1$_g$ 424g.

Returning again to FIGS. 11A and 11B, if, instead, the agent server 140 determines at 552 that there are two or more active collaborations in which participants of the participant type that generated the participant registration request are eligible to be registered in and have capacity therefor, the agent server 140 does not try to determine which collaboration to register the participant in and reports an error (560), after which the method 500 ends.

Figure 18:
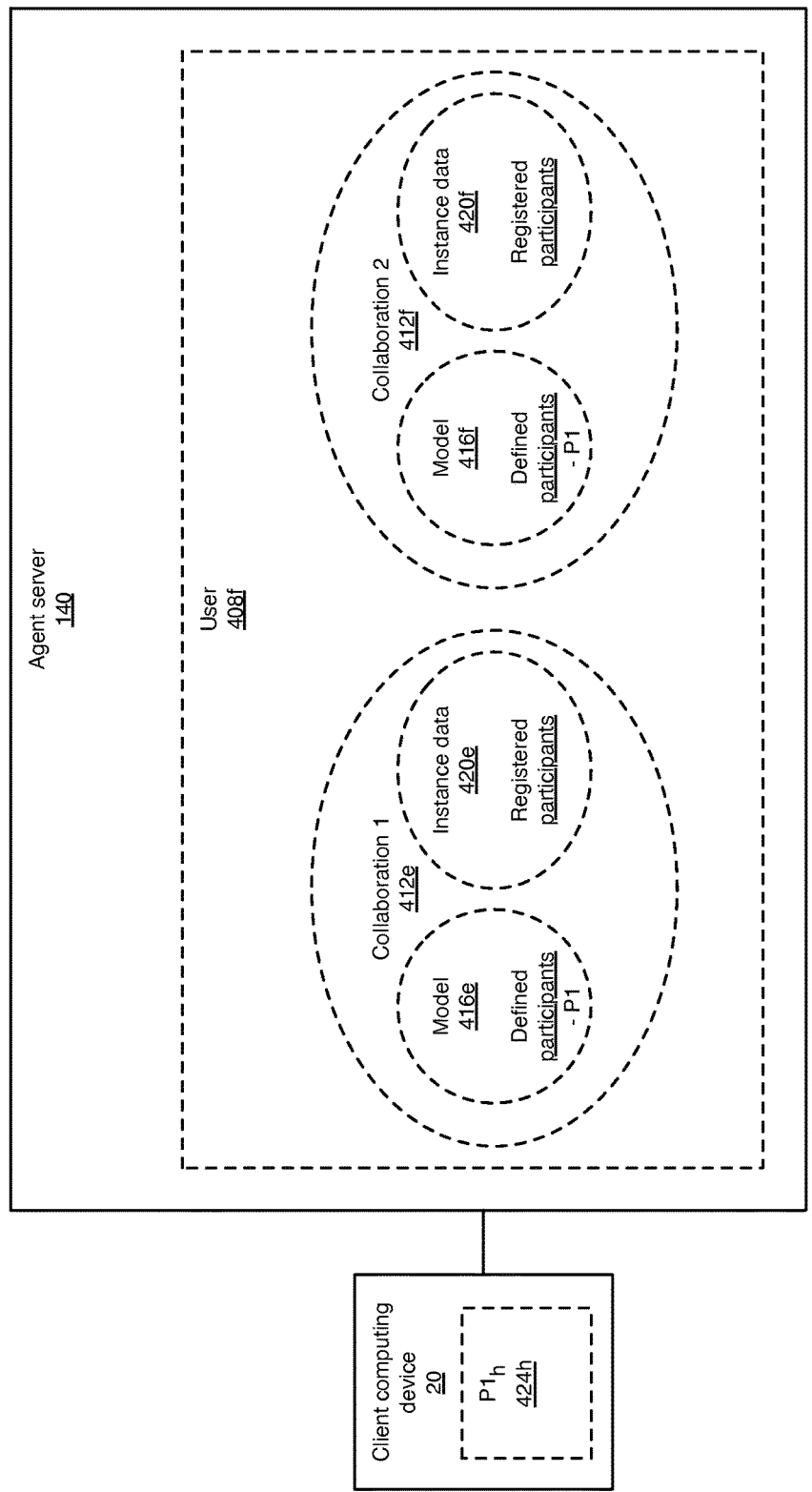
FIG. 18 shows two collaborations managed in a user space by the data-sharing server computer system of FIGS. 4 to 6, wherein both of the collaborations have capacity for a new participant of type P1.

FIG. 18 illustrates a circumstance where the personal computing device 20 executes a participant P1$_h$ 424h of the participant type P1. The agent server 140 is managing two separate collaborations 412e and 412f in which participants of the participant type P1 are permitted to be registered and that have capacity for a participant of this participant type in user space 408f for the user of the personal computing device 20. The models 416e, 416f of collaborations 412e, 412f respectively indicate that the collaborations 412e, 412f each permit a participant of participant type P1 to be registered therein. The instance data 420e, 420f for collaborations 412e, 412f respectively indicate that a participant of the participant type P1 is not currently registered in either of these collaborations. Upon receiving the participant registration request from participant P1$_h$ 424h for a collaboration of the collaboration type corresponding to the specified collaboration definition URI, the agent server 140 determines that there are at least two collaborations in which the participant P1$_h$ 424h can be registered. As a result, the agent server 140 does not register the participant P1$_h$ 424h in a collaboration and instead generates and reports an error to participant P1$_h$ 424h.

A participant will not receive any consume request notifications regarding updated data item values in the collaboration from the agent server 140 until it sends an enable notifications request to the agent server 140. This gives the participant time to finish its initialization before it starts receiving notifications from the agent server 140. Upon receiving an enable notifications request from a participant, the agent server 140 determines which, if any, of the participant's consume requests have undergone state changes and continually does so upon receipt of updates to data item values. Further, the participant regularly polls the agent server 140 to determine if the agent server 140 has flagged any consume requests as having undergone a state change. Continued receipt of these polls indicates to the agent server 140 that the particular participant is active. Conversely, cessation of receipt of these polls from a participant causes the agent server 140 to conclude that the particular participant has become inactive.

A participant may transmit a de-registration message to the agent server 140 to indicate that it no longer wants to participate in a collaboration. Alternatively, a participant can transmit a suspension request to indicate that it wants to temporarily suspend participation in the collaboration. Receipt of a de-registration request causes the agent server 140 to remove the participant and its consume requests from the instance data so that another participant of the same type can register in the collaboration, whereas receipt of a suspension request maintains the participant's spot in the collaboration. Thereafter, the suspended participant may re-register in the same collaboration to recommence participating in the collaboration.

The method by which a participant stops participating in a collaboration is relevant to the enable notifications request as it affects the consume requests that a participant receives when it enables notifications again. When a participant de-registers and then registers again, its consume requests are evaluated exactly the same as though the participant was joining for the first time. Any satisfied consume requests at the time the enable notifications request is made generate a consume request notification, even if the participant had already received a notification for the same values satisfying the consume request before de-registration. Instead, when a participant sends a suspension request, the behavior is slightly different. The participant will only be notified if there are newly-updated data item values for which the participant has not already received a consume request notification.

When a participant wishes to share data, it generates a data share message with the data item values and transmits it to the agent server 140. The data share message includes the URI of the share declaration in the participant definition 208 corresponding to the values being shared. Upon receiving the data share message, the agent server 140 determines if the participant is permitted to share the specified data item values using the participant definition 208 stored in the collaboration model. If the agent server 140 determines that the participant is permitted to share the particular data item values with the collaboration, the agent server 140 then processes the shared values to update the data item values in the collaboration and determine if any registered consume requests undergo a state change as a result.

Sharing Data

The method of receiving and providing shared data item values by the stateful data-sharing service will now be described with reference to FIGS. 4 to 8, and 19 to 21.

The agent server 140 uses the concept of transactions in processing data item value updates to properly isolate changes across participants so that the data item values passed on to participants upon a change of state of consume requests are consistent and current. For example, if a collaboration contains address information and a person, then transactions help to ensure that only address information related to the person currently active in the collaboration instance data is currently active, thus maintaining consistency in the information for the context of the user. Having several addresses for different people all active in the collaboration instance data at the same time could result in inconsistent information being delivered to participants that need relevant addresses. By grouping data item values according to transactions, consistency of data in a collaboration that is provided to participants can be ensured.

Transactions are sets of one or more logically-related operations performed on data item values. One or more participants can cooperatively perform the operations without knowledge of each other's existence or functions. When a set of data item values that was generated independent of any values received from the collaboration is shared via the agent server 140, it is referred to as the root of a transaction and is assigned a new transaction ID. As any of the root set of data item values is used by other participants to generate values for additional data items, those data item values form part of the same transaction and are assigned the same transaction ID. Participants receive the current transaction ID when they are notified with values matching their consume requests, and communicate this transaction ID when sharing data item values derived from the received values to enable the agent server 140 to identify which transaction the shared data item values relate to. In this manner, the agent server 140 tracks and segregates data item values for separate transactions, ensuring that the data item values that it receives form part of the current transaction and not part of a prior transaction.

The agent server 140 coordinates the transactions by simply receiving consume requests for data, and registering when the state of these consume requests change. The state of a consume request includes whether or not the consume request is satisfied by the data item values in the collaboration instance data and, if satisfied, the data item values that satisfied it. The share declarations and consume requests defined for the participants enable such transactions to be data-driven.

Figure 19:
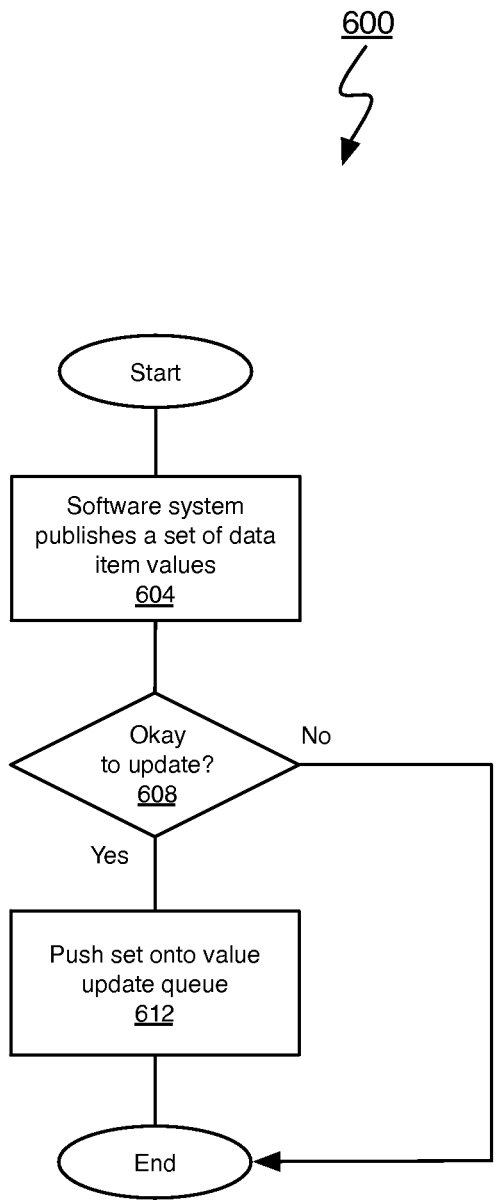
FIG. 19 is a flow chart of the general method of pre-processing sets of data item values shared by a participant used by the data-sharing server computer system of FIGS. 4 to 6.

FIG. 19 shows the method of pre-processing data item values shared by a participant (i.e., software system) generally at 600. The method 600 commences with a participant sharing a value of one or more data items (604). The participant provides the following as parameters of an HTTP request to the agent server 140:
the user token;
the participant token provided by the agent server 140 that the agent server 140 uses to look up the participant ID for the participant, and the collaboration ID of the collaboration in which the participant is participating;
a share declaration URI identifying what is being shared;
value(s) for the shared data items; and
a transaction ID for the set of data item value(s), if any, used to generate the data item value being published.

The agent server 140, upon receipt of the set of shared data item values, determines if the set of shared data item values is valid and should therefore be used to update the instance data in the collaboration (608). In particular, the agent server 140 determines if the share declaration URI provided with the shared values is present in the corresponding participant definition stored in the collaboration model, and that the values being shared match the criteria for the data items in the share declaration. If the agent server 140 determines that the share declaration URI is not in the corresponding participant definition in the collaboration model or if it determines that the values being shared do not match the criteria for the data items in the share declaration, the agent server 140 discards the shared set of data item values and the method 600 ends.

If, instead, the agent server 140 determines that the share declaration URI is in the corresponding participant definition in the collaboration model and if it determines that the values being shared match the criteria for the data items in the share declaration, the agent server 140 pushes the shared set of data item values onto a value update queue that it maintains (612). The agent server 140 also includes any transaction IDs received with the data item values. After placement of the set of data item values in the value update queue, the method 600 ends.

Updating Data in the Collaboration

The agent server 140 processes the sets of data item values in the value update queue and updates the instance data in the collaboration accordingly. In some cases, a software system may generate and share a set of data item values in response to receiving a set of data item values from the agent server 140 corresponding to one of its consume requests. The agent server 140, however, may know that the values used by the software system are obsolete due to a new transaction having been started. In this case, the agent server 140 discards the set of data item values received from the software system as it knows they relate to an old transaction. The agent server 140 assigns a unique transaction ID to each set of data item values that form part of a transaction.

Figure 20:
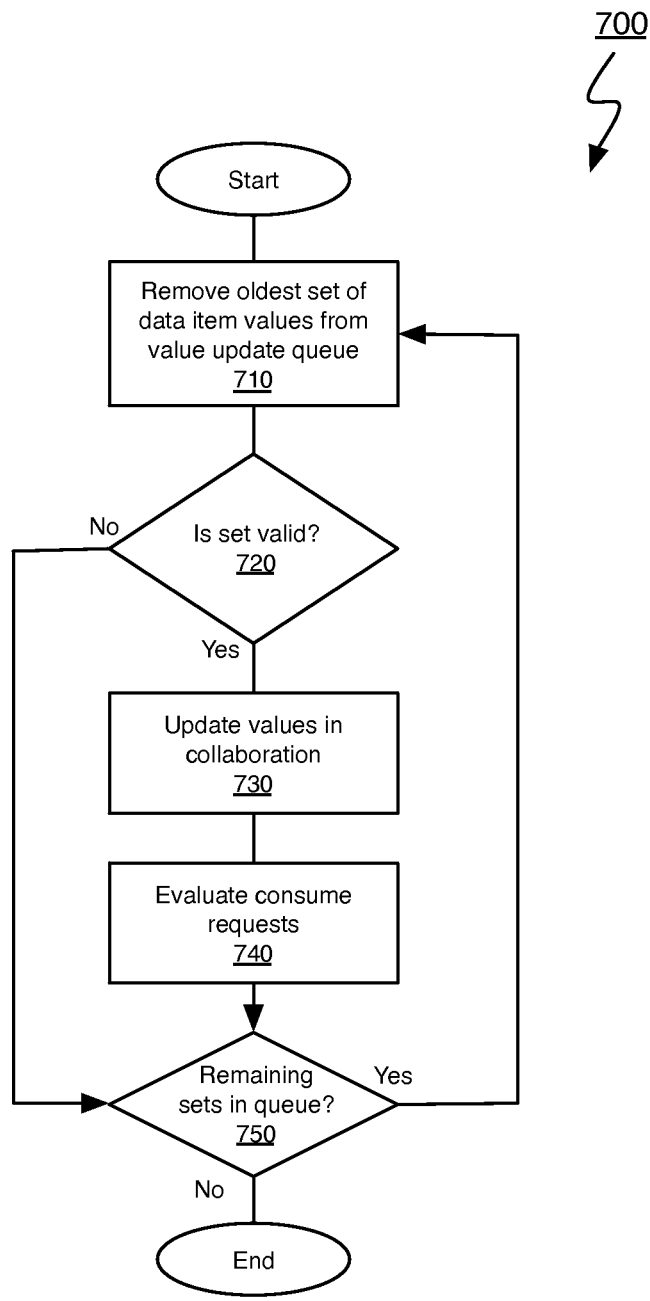
FIG. 20 is a flow chart of the general method of processing sets of data item values shared by a participant used by the data-sharing server computer system of FIGS. 4 to 6.

FIG. 20 shows the method of processing sets of data item values in the value update queue generally at 700. This method 700 is executed whenever the value update queue has at least one set of data item values for updating in it. The method 700 begins with the removal of the oldest set of data item values from the value update queue (710). The agent server 140 generally processes sets of data item values in the order that they are received. The set of data item values is accompanied by the URI of the share declaration for the set of shared values and the transaction ID, if any, identifying the transaction to which the data item values belong. The agent server 140 then determines if the data item values in the set removed from the value update queue are valid (720). In particular, the agent server 140 determines if the data item values are part of a current or outdated transaction. If the set of data item values removed from the value update queue was not accompanied by a transaction ID, the set of data item values are taken to begin a new transaction. If the set of data item values removed from the value update queue were accompanied by a transaction ID, the agent server 140 examines the transaction ID to determine if it is still current. That is, the agent server 140 determines if the set of data item values put into the value update queue correspond to an outdated or current transaction. If the data item values are part of a prior transaction, the data item values are deemed to be invalid.

If the set of data item values removed from the value update queue are determined to be valid by the agent server 140 at 720, the agent server 140 updates the set of data item values in the instance data of the collaboration (730). If the set of data item values does not have a transaction ID, then the agent server 140 also generates a new unique transaction ID for the set of data item values placed in the instance data of the collaboration.

Once the agent server 140 has updated the instance data in the collaboration for the new data item values, the agent server 140 evaluates the registered consume requests (740) for all participants. If a consume request has undergone a state change, the agent server 140 flags the consume request as having undergone a state change so that the participant will be notified upon receiving the next poll. For server-side participants, the agent server 140 provides the data item values to the corresponding proxy connector participant. Upon evaluating all of the registered consume requests for the data item values updated, the updating of the set of data item values is complete and the agent server 140 determines if there are remaining sets of data item values in the value update queue (750). Additionally, if the set of data item values are deemed invalid at 720, the agent server 140 then determines if there are remaining sets of data item values left in the value update queue at 750. If the agent server 140 determines there are remaining sets of data item values to be updated in the value update queue at 750, the method 700 returns to 710, wherein the agent server 140 removes the oldest remaining set of data item values from the value update queue. If, instead, the agent server 140 determines that there are no remaining sets of data item values in the value update queue, the method 700 ends.

Evaluating Consume Requests

Figure 21:
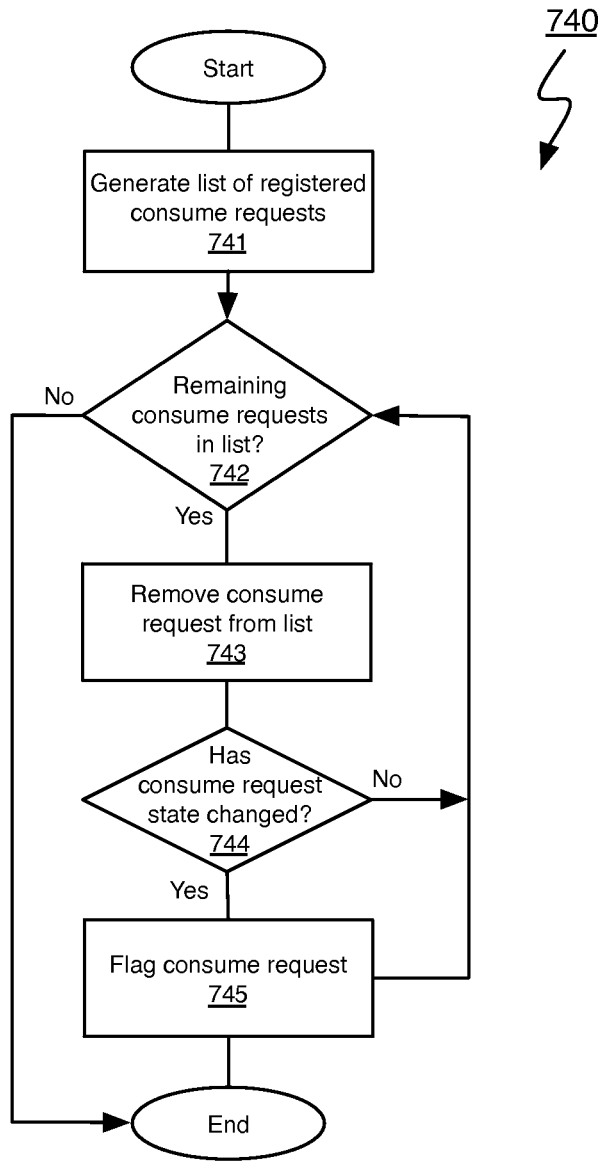
FIG. 21 is a flow chart of the general method of evaluating consume requests used by the data-sharing server computer system of FIGS. 4 to 6.

FIG. 21 shows the process of evaluating the consume requests at 740 in the method 700 in greater detail. First, the agent server 140 generates a list of all registered consume requests (741). The agent server 140 only reviews consume requests registered in the instance data in the collaboration; that is, registered consume requests for software systems that are believed to be active. The list of consume requests generated at 741 may be empty or may include one or more consume requests. The agent server 140 then determines if there are any remaining consume requests in the list (742).

If there are remaining consume requests in the list, then the agent server 140 removes a consume request from the list (743). The agent server 140 determines if the consume request removed from the list has undergone a state change (744). As previously noted, consume requests have undergone a state change if the consume request becomes satisfied or becomes unsatisfied, or, if satisfied, if the data item values that satisfied it have changed. The consume request is satisfied if the query evaluator can semantically resolve the data requested in the included standing query to valid data item values in the instance data in the collaboration using the semantic descriptors for those data items; that is, if the standing query returns results. If the consume request has not undergone a state change, the agent server 140 determines if there are remaining consume requests in the list at 742. If the consume request has undergone a state change, the agent server 140 flags the consume request (745). After the consume request is flagged at 745, the agent server 140 determines if there are remaining consume requests in the list at 742. Once the agent server 140 determines that there are no remaining consume requests in the list at 742, the process of evaluating the consume requests is complete.

It is undesirable to process consume requests for participants that are no longer registered in the collaboration. In order to ensure that the agent server 140 only processes consume requests for active or suspended participants in the collaboration, consume requests for de-registered participants are removed from the instance data in the collaboration. When a software system is configured to terminate participating in a collaboration, such as when it is shutting down, the software system transmits a de-registration request with its participant token and user token to the agent server 140. In response, the agent server 140 notes the de-registration of the software system and removes the consume requests of the software system and the registration of the software system itself from the instance data in the collaboration. Additionally, when the agent server 140 stops receiving polls from a software system, the agent server 140 can de-register the software system and its consume requests from the collaboration. The agent server 140 maintains the data item values in the instance data in the collaboration provided by a software system 116 that de-registers, unless directed otherwise by the software system.

Representative Types of Participants in Collaborations

Figure 22A:
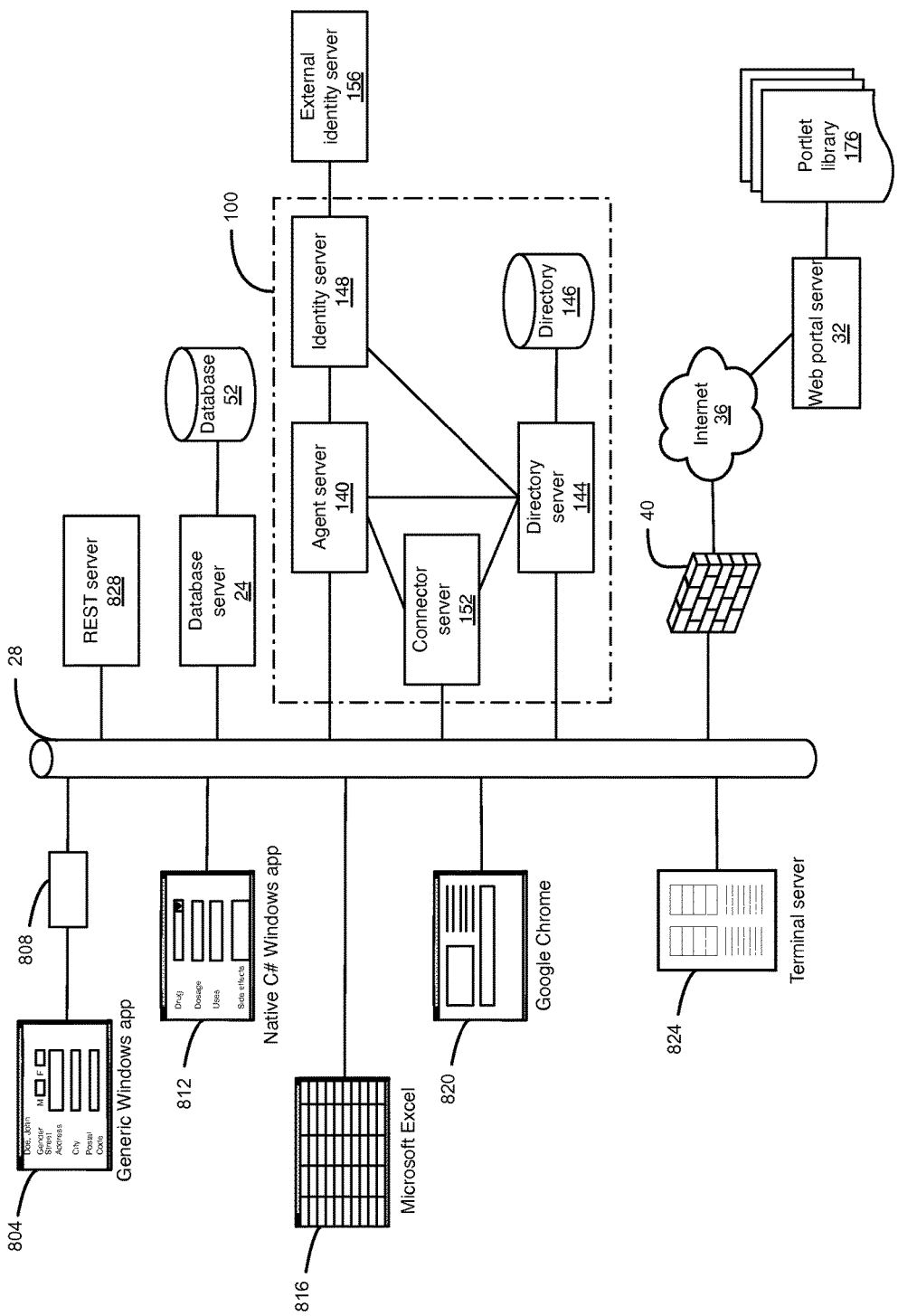
FIG. 22A shows a schematic diagram of various logical components of software systems that can participate in a collaboration managed by the data-sharing server computer system of FIGS. 4 to 6.

FIG. 22A illustrates various representative types of software modules, programs, applications, services, etc. that can make up software systems that can participate in a collaboration. A generic Microsoft Windows application 804 executing on a personal computing device is shown in communication with the intranet 28 via a Windows application adapter 808. A native C# Windows application 812, Microsoft Excel 816, and a Google Chrome Web browser 820 also executing on the same or other personal computing devices are also shown in communication with the intranet 28. Further, a terminal server 824, a REST server 828, and the database server 24 are in communication over the intranet 28. The Web portal server 32 is also in communication with the other components via the Internet 36 through the firewall 40. Further, the agent server 140, the directory server 144 and the connector server 152 are also in communication with some or all of the other above-noted components via the intranet 28.

Figure 22B:
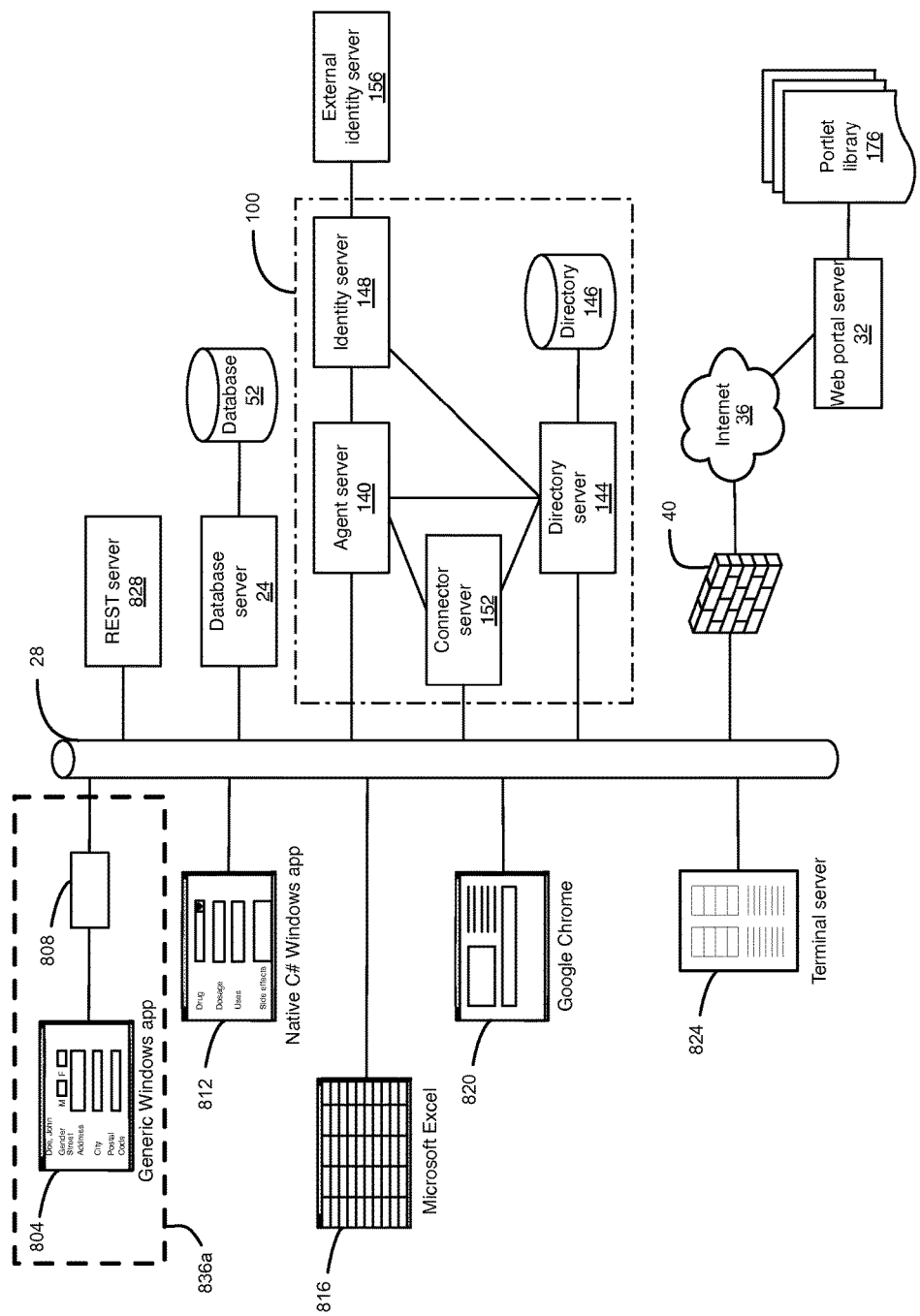
FIGS. 22B to 22H show the delineation of each separate software system that can participate in a collaboration managed by the data-sharing server computer system of FIGS. 4 to 6.

FIG. 22B identifies the generic Microsoft Windows application 804 and the Windows application adapter 808 as forming a first software system 836*a*. The Windows application adapter 808 communicates with the generic Windows application 804 via Microsoft User Interface Automation functionality. When this functionality is enabled on a Microsoft Windows-based computer, the Windows application adapter 808 can observe the generic Windows application 804 and share data item values that are updated therein. The Windows application adapter 808 polls the agent server 140 for consume request notifications and retrieves updated values for data items corresponding with consume requests and uses those values to populate the fields of the generic Windows application 804.

Figure 22C:
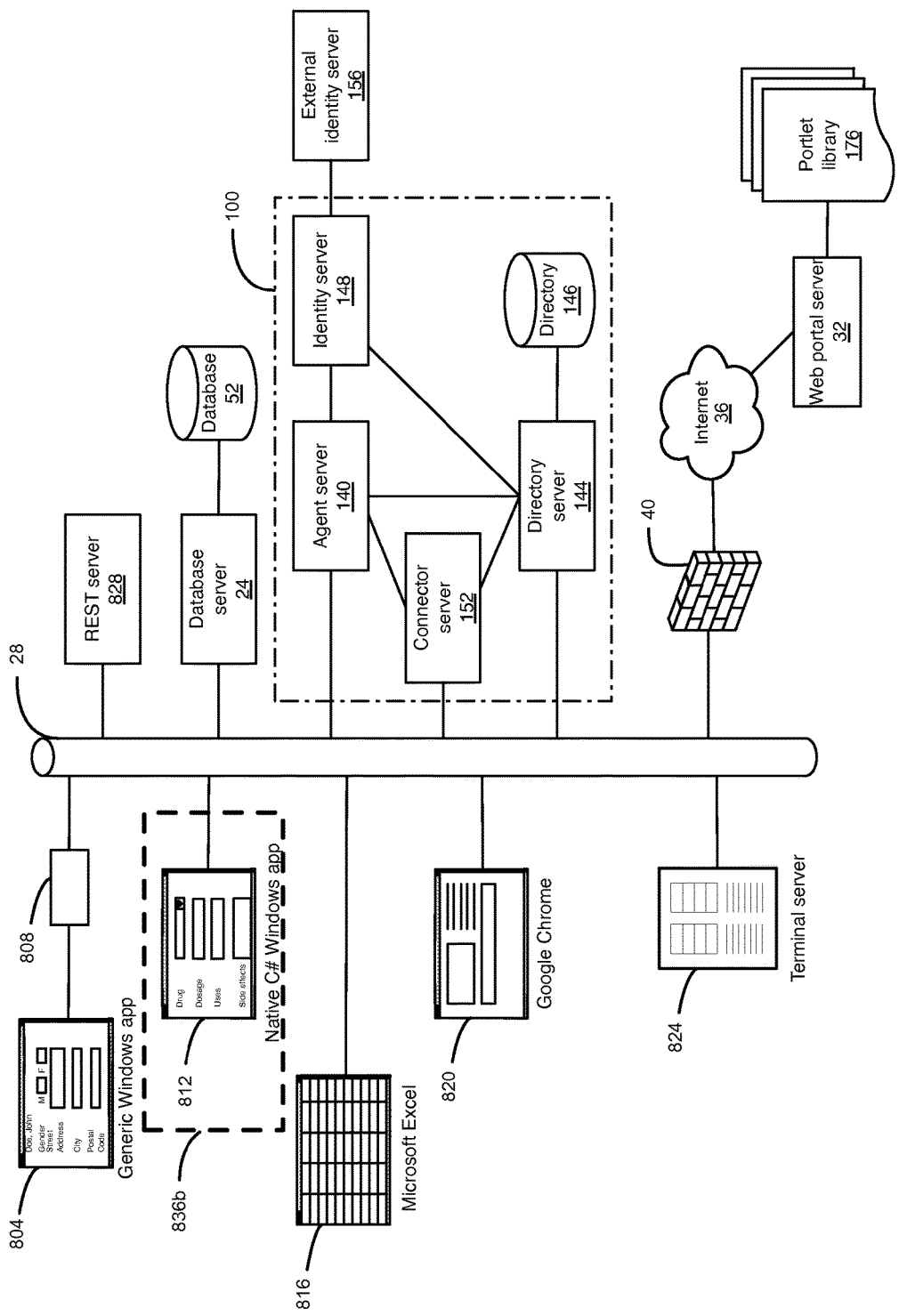

FIG. 22C shows a second software system 836*b*, wherein the native C# Windows application is programmed to interact with the agent server 140 to participate in collaborations.

Figure 22D:
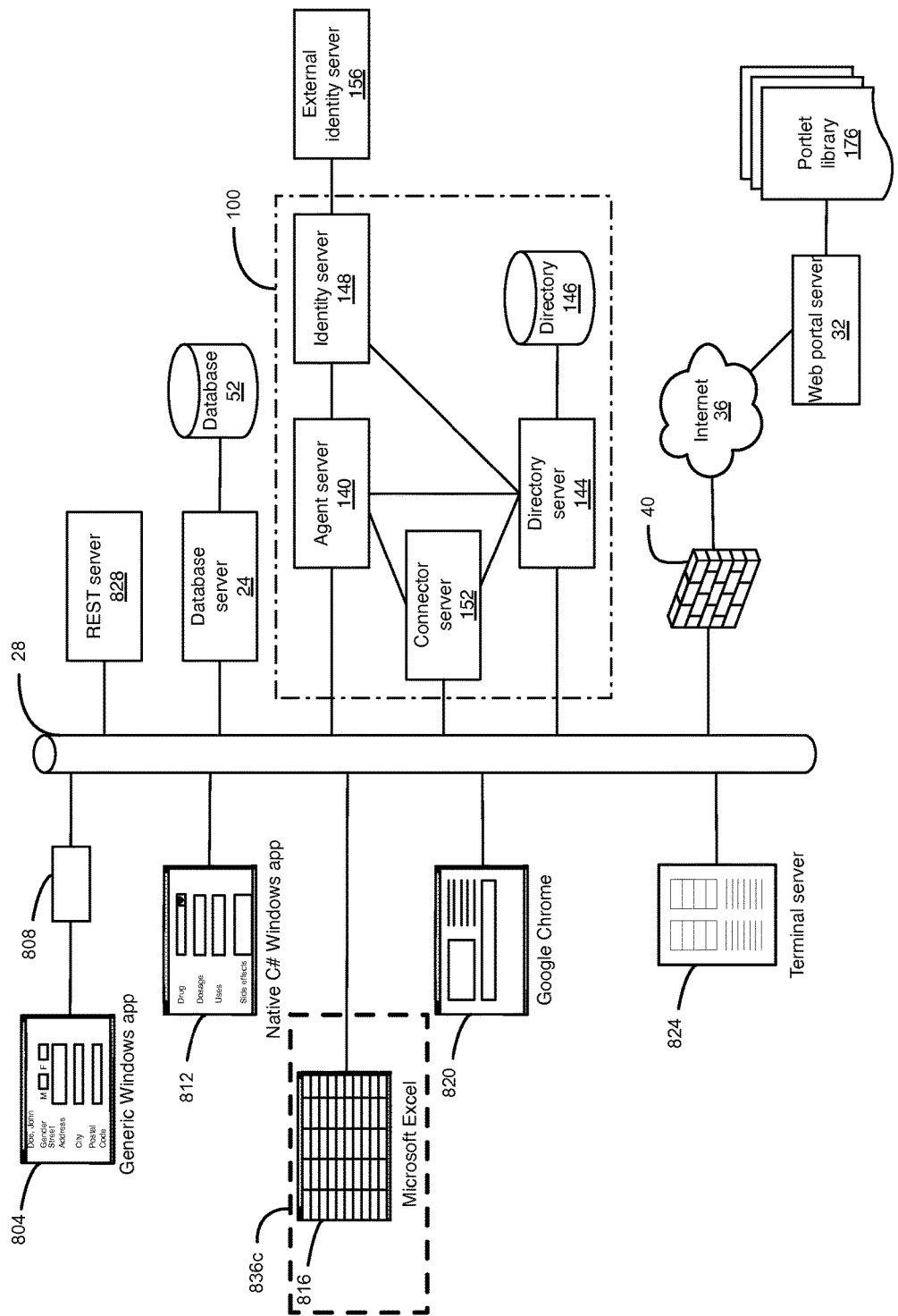

FIG. 22D shows a third software system 836*c* that includes Microsoft Excel 816. An add-in is installed in Microsoft Excel. The add-in extends the functionality of Excel by defining a set of custom functions that permit share declarations and consume requests to be defined in cells of a spreadsheet. In addition, the custom functions enable a user to provide login credentials entered in the spreadsheet to the stateful data sharing service when the spreadsheet is opened. The share declaration function provided with the add-in causes updated values of the function to be communicated to the agent server 140. The consume request function provided with the add-in periodically queries the agent server 140 for consume request notifications.

Figure 22E:
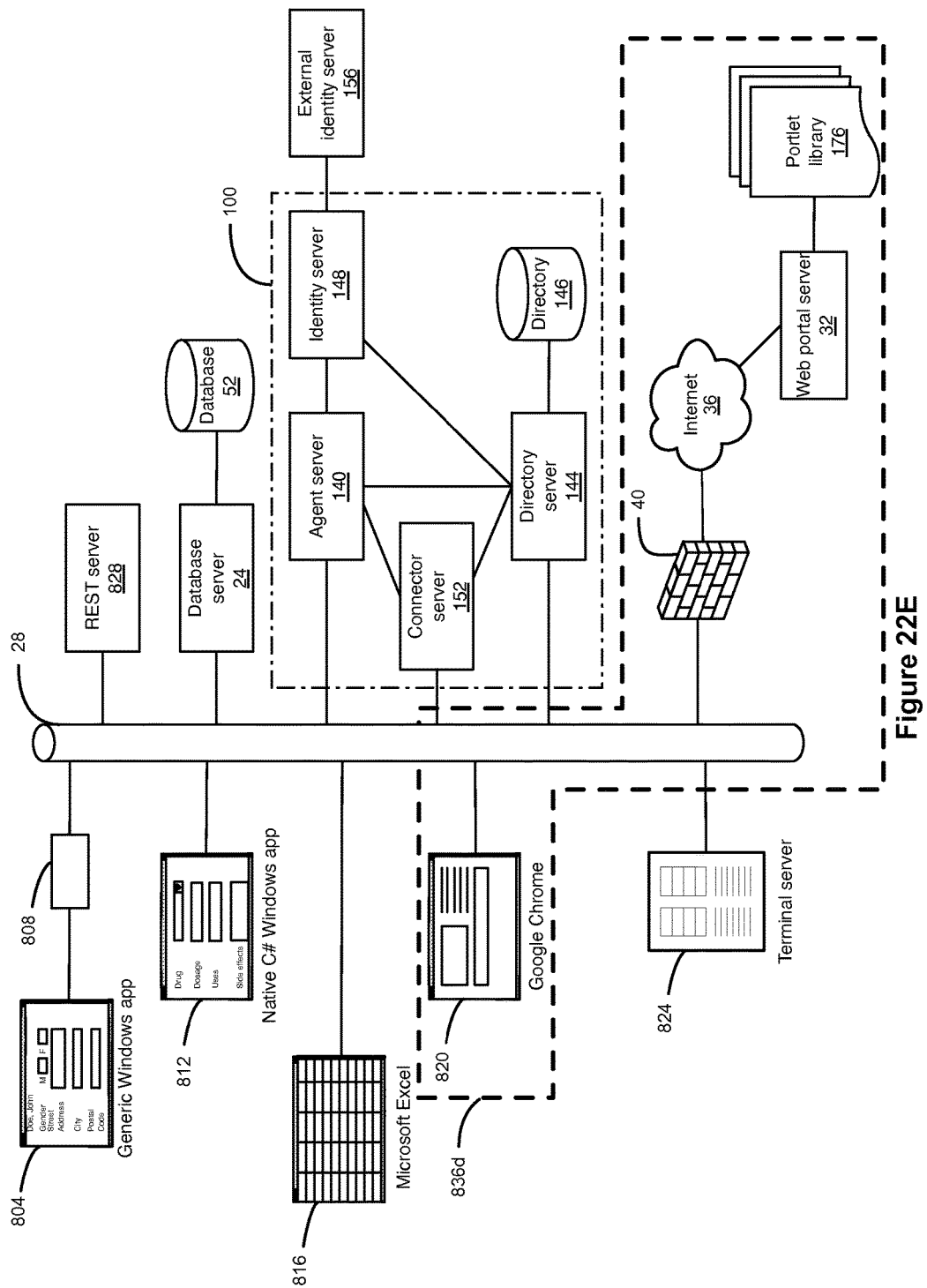

FIG. 22E shows a fourth software system 836*d*, wherein the Google Chrome Web browser 820 communicates with the Web portal server 32 to retrieve Web pages. This is implemented in one of two ways. In a first mode, native JavaScript is injected into Web pages received from the Web portal server 32, by a browser extension, dynamic proxy, or server side filter, enabling them to interact with the agent server 140 to participate in collaborations and share data within Web pages. In a second mode, the Web page generated by the Web portal server 32, or portlets therein as retrieved from the portlet library 176, include scripts to cause the Google Chrome Web browser 820 to interact with the agent server 140 to participate in collaborations and share data within Web pages.

Figure 22F:
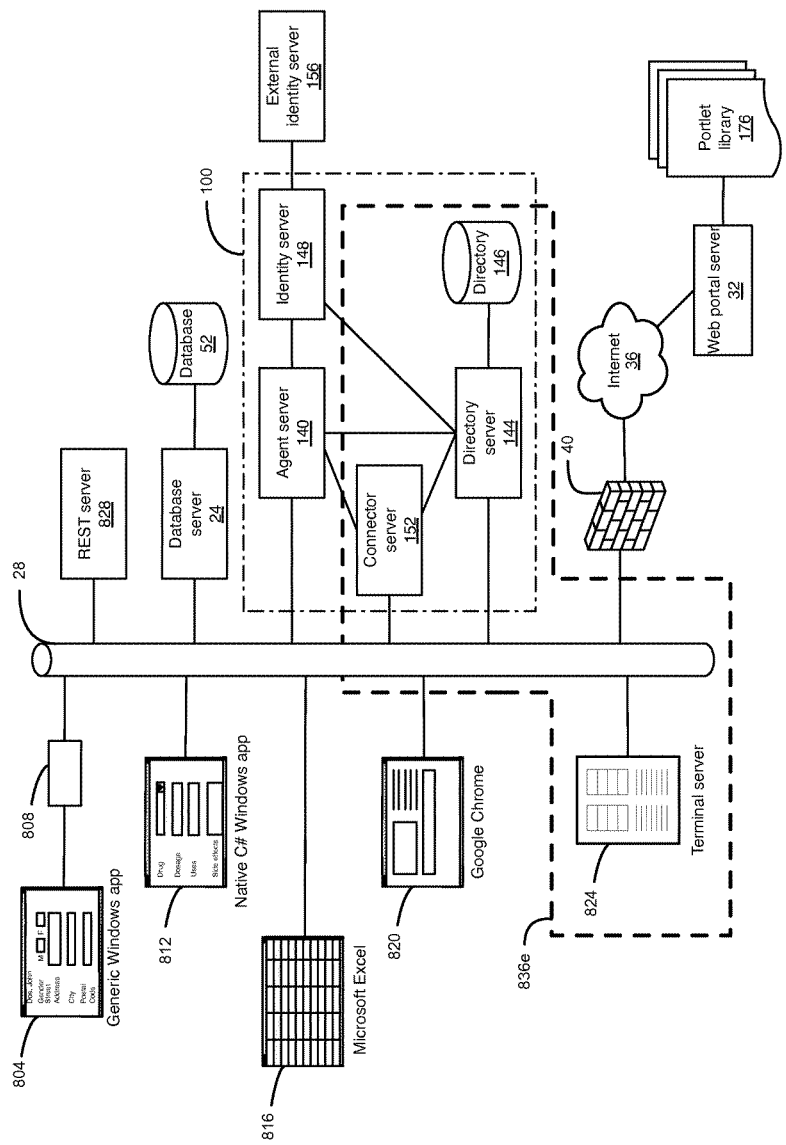

FIG. 22F shows a fifth software system 836*e*, wherein a terminal services connector executed by the connector server 152 connects to the terminal server 824. The consume requests within the participant definition 208 include the URL of the terminal server 824 and terminal commands to be executed when data item values in the collaboration cause the consume request state to change. A consume request can have an associated share declaration in the participant definition corresponding to data item values generated by the terminal server 824 in response to the terminal commands that are to be shared with the collaboration. When a collaboration is created that includes a proxy connector participant associated with the terminal services connector, the agent server 140 instantiates and registers the proxy connector participant. As the proxy connector participant is provided data item values for a consume request that underwent a state change, it passes the values to the terminal services connector, together with the user token, the participant definition URI, and the consume request definition URI. In response, the terminal services connector retrieves the consume request definition and any associated share declarations from the directory server 144. The consume request definition includes the URL of the terminal server 824 and any syntax for generating associated terminal commands. The terminal services connector then generates terminal commands including these data item values and transmits them to the terminal server 824, and provide data item values returned by the terminal server 824 to the proxy connector participant in response to the terminal commands. The proxy connector participant, in turn, shares these values with the collaboration via the agent server 140.

Figure 22G:
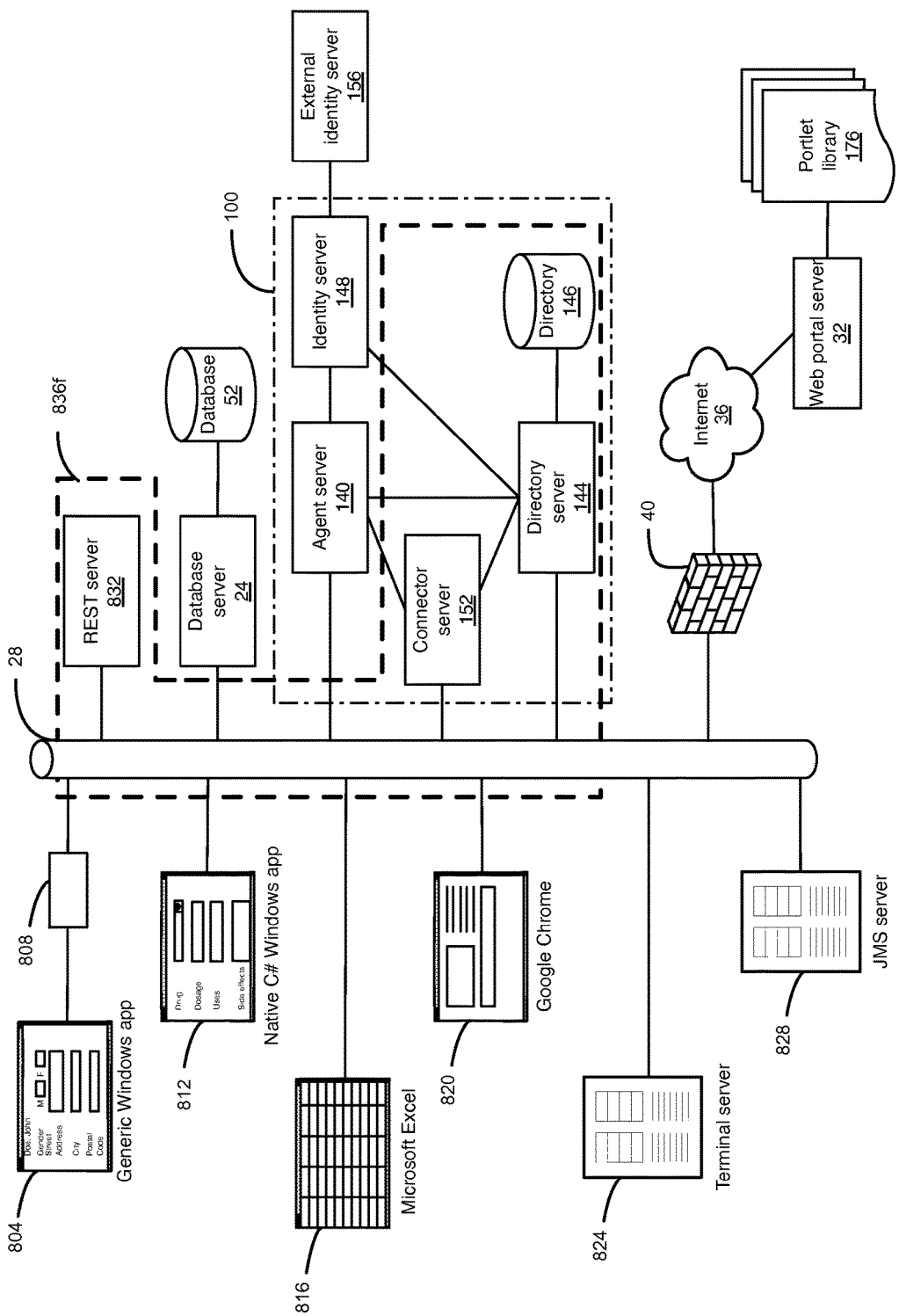

FIG. 22G shows a sixth software system 836*f*, wherein a REST connector executed by the connector server 152 connects to the REST server 828. The consume requests within the participant definition 208 include the URL of the REST server 828, as well as mapping statements that allow information from the collaboration to be used to generate, and determine the type (GET/POST) of the resource request. When a collaboration is created that includes a proxy connector participant associated with the REST connector, the agent server 140 instantiates and registers the proxy connector participant. As the proxy connector participant is provided data item values for a consume request that underwent a state change, it passes the values to the REST connector, together with the user token, the participant definition URI, and the consume request definition URI. In response, the REST connector retrieves the consume request definition and any associated share declarations from the directory server 144. The consume request definition includes the URL of the REST server 828 and any syntax for generating associated commands. The REST connector can then generate and send REST requests including the data item values to the REST server 828, and provide data item values returned by the REST server 828 to the proxy connector participant in response to the REST requests. The proxy connector participant, in turn, shares these values with the collaboration via the agent server 140.

Figure 22H:
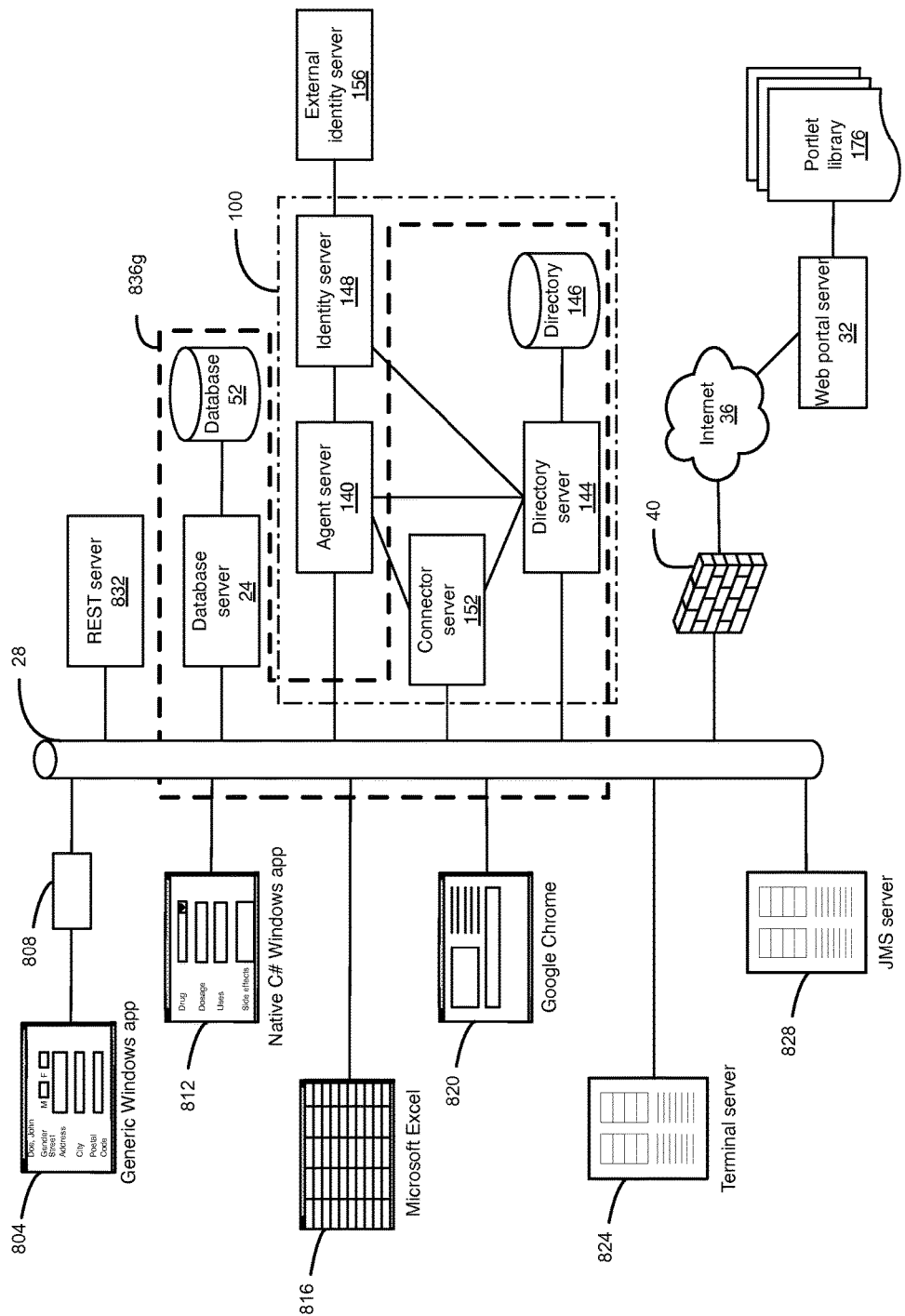

FIG. 22H shows a seventh software system 836*g*, wherein a database connector executed by the connector server 152 connects to the database server 24. The consume requests within the participant definition 208 include the URL of the database server 24 and parameters for constructing database queries and write messages. When a collaboration is created that includes a proxy connector participant associated with the database connector, the agent server 140 instantiates and registers the proxy connector participant. As the proxy connector participant is provided data item values for a consume request that underwent a state change, it passes the values to the terminal services connector, together with the user token, the participant definition URI, and the consume request definition URI. In response, the database connector retrieves the consume request definition and any associated share declarations from the directory server 144. The consume request definition includes the URL of the database server 24 and any syntax for generating associated database requests. The database connector then generates database queries and write messages using the information from the consume request definition and transmits them to the database server 24. The database connector can then provide data item values returned by the database server 24 to the proxy connector participant in response to the database queries. The proxy connector participant, in turn, shares these values with the collaboration via the agent server 140.

Figure 22I:
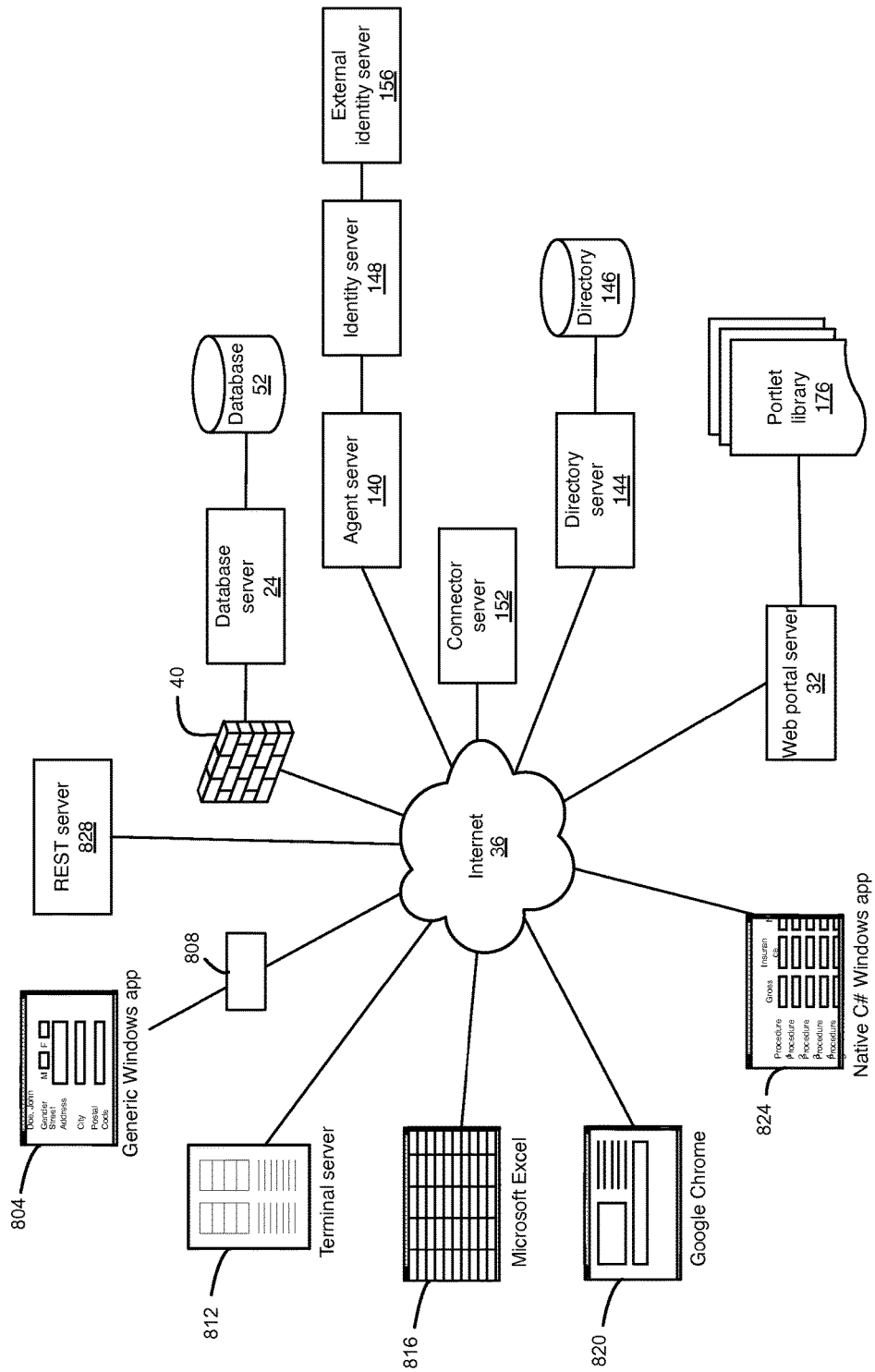
FIG. 22I shows an alternative configuration of the logical components of the software systems and the data-sharing server computer system of FIG. 22A.

FIG. 22I shows an alternative configuration for the components shown in FIG. 22A. In this alternative configuration, each of the components is in communication with the other components over the Internet 36. The directory server 144, connector server 152 and agent server 140 can all be located remotely from one another. Even though the identity server 148 and the external identity server 156 are shown in direct communication with the agent server 140, it should be understood that these services can also be located remotely from the other components. This is made possible as the addresses of each server are provided as a URL. In such a configuration, it may be desirable to have one or more ports opened on the firewall 40 for database connectors in the connector server 152 to talk to the database server 24.

In another configuration, it may be desirable to locate a connector server 152 topologically adjacent the resource(s) and/or server(s) providing functionality that they are accessing for performance and/or security reasons.

Illustrative Example of Operation of System

In order to illustrate the functioning of the system, its operation will now be described with reference to the configuration of FIG. 6.

As previously discussed, the first software system includes the patient medical database client 160 executing on the tablet 20*a* that communicates with the database server 24 to provide access to data in the patient medical database 52 managed by the database server 24. The patient medical database client 160 has been customized to communicate with the agent server 140 in order to participate in collaborations.

The second software system includes the clinical management application 164 for scheduling patient consultations and procedures, generating invoices for patient visits for each patient and recording other accounting information. The clinical management application 160 has been customized to communicate with the agent server 140 in order to launch collaborations and to participate in them.

The third software system includes a proxy connector participant executed by the agent server 140 in communication with a Web connector executed by the connector server 152. The Web connector uses information received from the collaboration via the proxy connector participant and from the directory server to retrieve information from the Web portal server 32 when a consume request is satisfied, and can return information received from the Web portal server 32, the insurance coverage amount(s) in this particular case, to the collaboration via the proxy connector participant.

A user would typically have the clinical management application 164 open during the course of the day to manage patients, invoices, etc. Upon executing the clinical management application 164 on the desktop computer 20*b* at the start of the day, programming code in the clinical management database obtains user login credentials from the user and communicates them to the agent server 140. In response, the agent server 140 provides these credentials to the identity server 148 for authentication. Once authenticated, the identity server 148 generates a user token associated with the user's identity and returns it to the agent server 140, which forwards it to the clinical management application 164. Upon receipt of the user token, the clinical management application 164 generates and transmits a collaboration creation request to the agent server 140. The collaboration creation request includes the URI of the collaboration definition 204 and the user token. No collaboration ID is included in the collaboration creation request in this example. The agent server 140 passes the user token to the identity server 148, which validates it. The agent server 140 then proceeds to create a collaboration using the method of FIG. 9 and generates a collaboration ID for the collaboration that is unique for the user.

Figure 23:
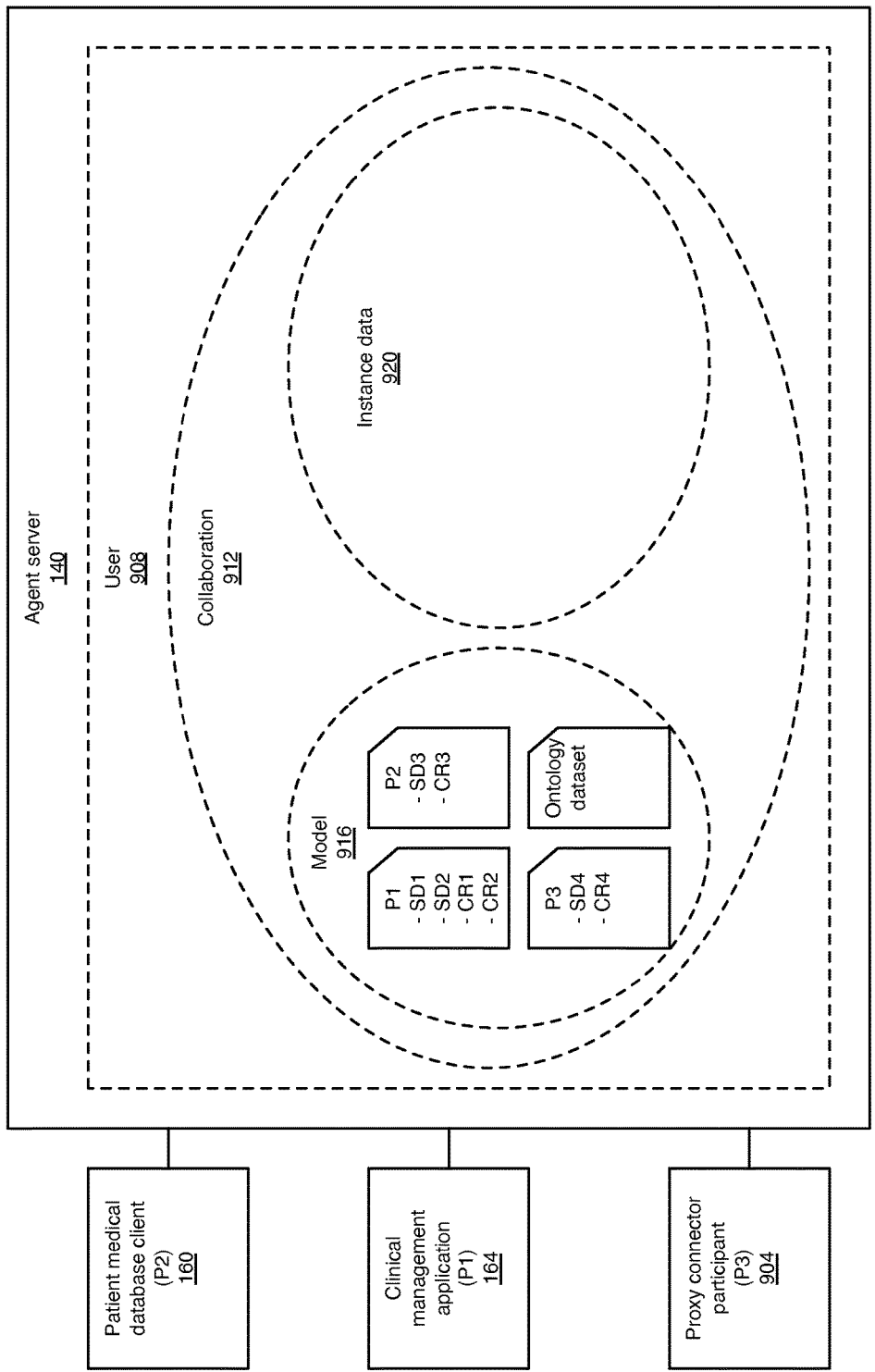
FIG. 23 illustrates the state of a collaboration after its creation by the data-sharing server computer system of FIGS. 4 to 6.

FIG. 23 shows the three participants (the clinical management application 164, the patient medical database client 160 and the proxy connector participant 904 that is in communication with the Web connector) in communication with the agent server 140 after the creation of the collaboration. The agent server 140 has created a user space 908 for the user and, in it, has created a collaboration 912 and generated a unique collaboration ID for it. The collaboration 912 has a collaboration model 916 and instance data 920. The collaboration model 916 includes the participant definitions for each of the three participants, including their consume request definitions and share declarations.

The participant definition for the clinical management application 164, labeled as P1 in FIG. 23, has the following consume request definitions (CR) and share declarations (SD):

CR1: "list of services provided" (the consultations, procedures, medications prescribed)
CR2: "insurance-covered amounts"
SD1: "patient ID"
SD2: "policy number", "person ID", "costs of services provided"

The participant definition for the patient medical database client 160, labeled as P2 in FIG. 23, has the following consume request definitions and share declarations:

SD3: "list of services provided"
CR3: "patient ID"

The participant definition for the proxy connector participant 904, labeled as P3 in FIG. 23, has the following consume request definitions (CR) and share declarations (SD):

CR4: "policy number", "person ID", "list of services provided", "costs of services provided"
SD4: "insured amounts"

In addition, the collaboration model 916 includes an ontology dataset specified in the collaboration definition. This ontology dataset is used by the agent server 140 to resolve the data item, "insurance-covered amounts", specified in the consume request CR2 to the data item shared by the proxy connector participant 904, "insured amounts".

These consume request definitions and share declarations are registered in the collaboration model 916 as shown. The agent server 140 provides the user token generated by the identity server 148 to the clinical management application 164.

The agent server 140 examines each participant definition and determines that the proxy connector participant P3 is a server-side participant. It then instantiates the proxy connector participant that communicates with the Web connector in the collaboration 912 and registers it therein.

Figure 24:
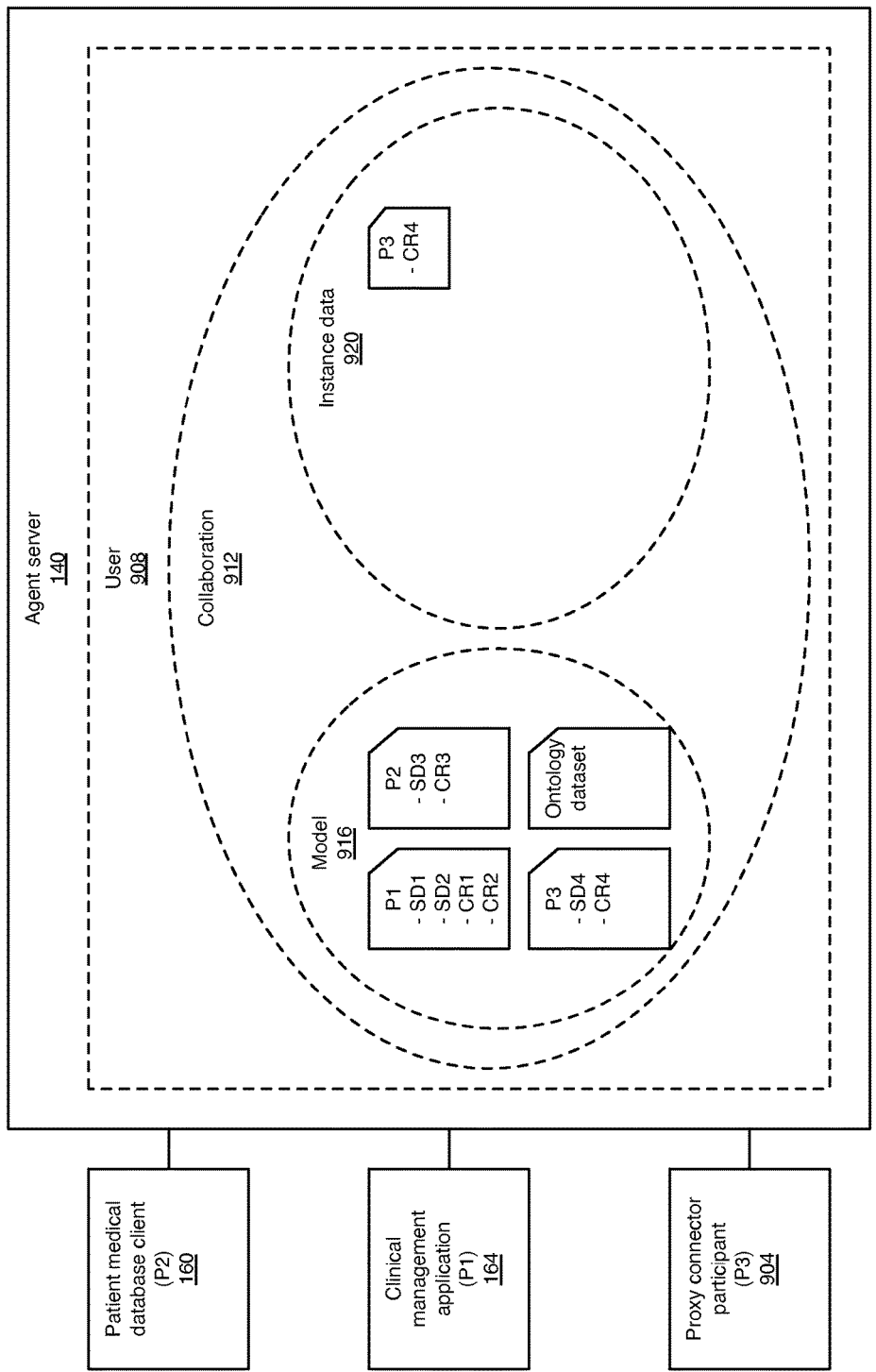
FIG. 24 illustrates the state of the collaboration of FIG. 23 after a Web connector (via a proxy connector participant) is registered therein.

FIG. 24 illustrates the state of the collaboration after registration of the proxy connector participant P3. As can be seen, the proxy connector participant (represented as P3) has been instantiated in the instance data 920, together with its consume request, CR4.

As soon as the proxy connector participant is registered in the collaboration 912, the agent server 140 evaluates its consume request CR4 using the method 740. As previously noted, consume request CR4 identifies a set of data items, "policy number", "person ID", "list of services provided", and "costs of services provided". The agent server 140 determines that the consume request CR4 has not undergone a state change as it is not yet satisfied; i.e., as values for all of these data items are not in the instance data 920.

After the collaboration creation request has been transmitted and upon receipt of the user token, the clinical management application 164 transmits a participant registration request to the agent server 140. The participant registration request includes the participant definition URI, consume request URIs for CR1 and CR2, the user token received from the agent server 140, and an enable notifications request. Upon receipt of the participant registration request from the clinical management application 164, the agent server 140 registers the clinical management application 164 in the collaboration instance data 920 using the method 500. In addition, the agent server 140 registers the consume requests corresponding to the consume request definitions matching the URIs provided in the participant registration request. The agent server 140 then generates a participant token that the agent server 140 uses to uniquely identify the clinical management application 164 and the collaboration ID of the collaboration into which it has been registered, and returns it to the clinical management server 164 for use with future communications. Thereafter, the clinical management application 164 polls the agent server 140 regularly to determine if any of its consume requests have undergone a state change.

Figure 25:
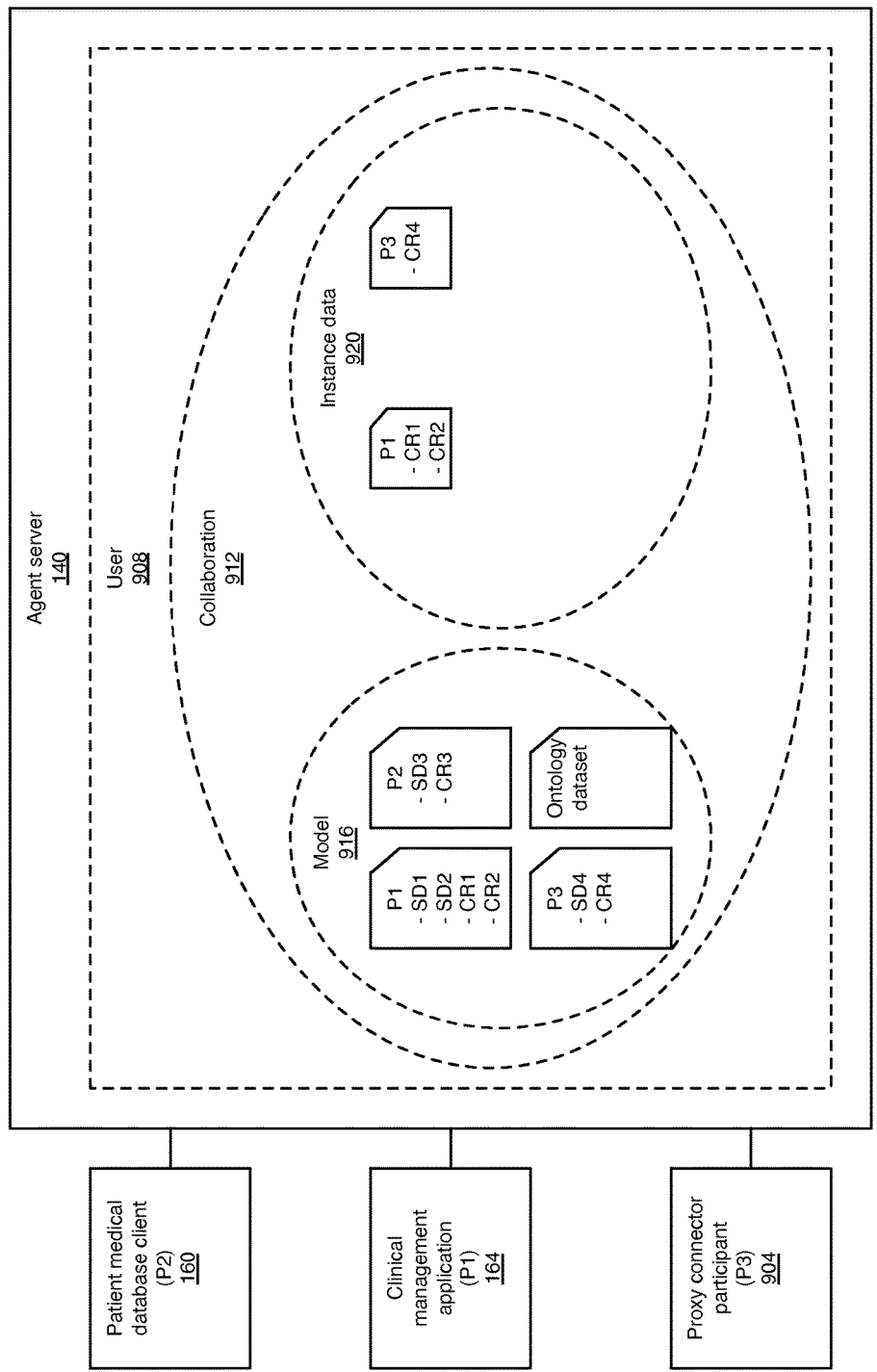
FIG. 25 illustrates the state of the collaboration of FIG. 24 after the clinical management application is registered therein.

FIG. 25 illustrates the state of the collaboration after registration of the clinical management application 164. As can be seen, the clinical management application 164 (represented as P1) has been instantiated in the instance data 920, together with its consume requests, CR1 and CR2.

The clinical management application 164 enables a user to select patients from a list, from an appointment calendar, etc. A user might select a patient when a patient arrives in the facility and is ready to be consulted with, examined or treated. Upon selection of a patient, the clinical management application 164 shares "patient ID" with the agent server 140, together with the URI of the corresponding share declaration for SD1, the participant token received from the agent server 140, and the user token generated by the identity server 148. Upon receiving the shared value, the agent server 140 determines if the shared value is valid before putting the shared value on the value update queue using the method 600. The agent server 140 then processes the shared value in the value update queue, updates the value in the instance data 920, and evaluates any consume requests using the method 700.

Figure 26:
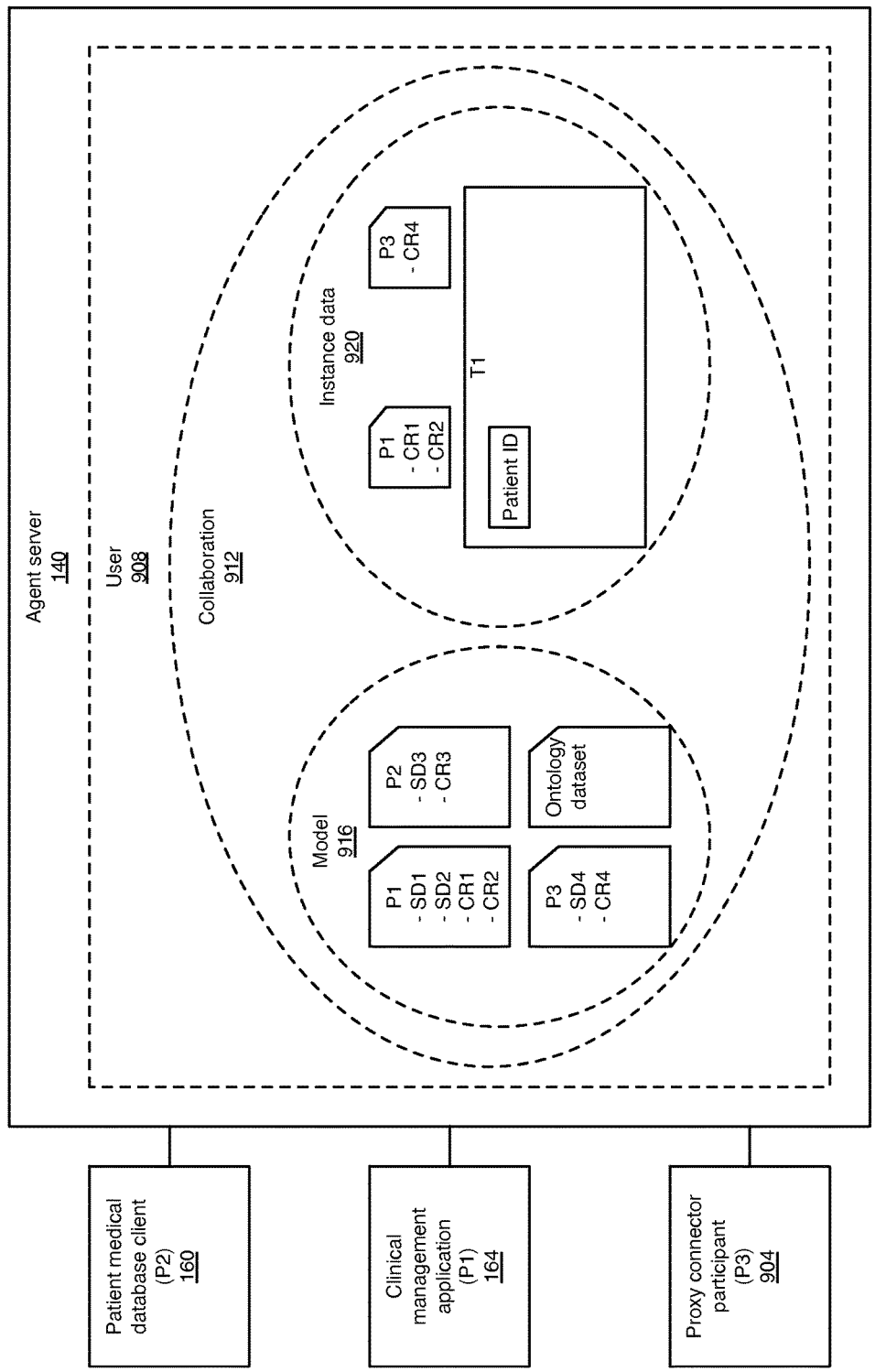
FIG. 26 illustrates the state of the collaboration of FIG. 25 after the clinical management application shares a value for "patient ID" therein.

FIG. 26 illustrates the state of the collaboration after the sharing of the patient ID by the clinical management application 164. The data item "patient ID" forms part of a first transaction, T1, as no transaction ID was received with the shared value.

As there are no consume requests that are registered in the instance data 920 that are newly satisfied by the new value (that is, neither CR1, CR2 nor CR4 are satisfied by the introduction of the new value, the agent server 140 does not flag any consume requests as having undergone a state change.

The patient medical database client 160 is then started up by the user, and asks the user for login credentials for the stateful data sharing service. Upon providing these login credentials, the patient medical database client 160 transmits these login credentials to the agent server 140. The agent server 140 forwards them to the identity server 148 for authentication. Upon authenticating the user login credentials, the identity server 148 generates a user token associated with the user's identity and returns it to the agent server 148, which, in turn, forwards it to the patient medical database client 160. Upon receipt of the user token, the patient medical database client 160 sends a participant registration request to the agent server 140 for processing using the method 300. The participant registration request includes the participant definition URI corresponding to the patient medical database client 160, the consume request URI for CR3, the user token, and an enable notifications request. The agent server 140 passes the user token to the identity server 148 for authentication. Upon verification of the user's identity, the agent server 140 finds the corresponding user space 908, determines that collaboration 912 is the only collaboration that the patient medical database client 160 is eligible to join and that has capacity for it, and proceeds to register the patient medical database client 160 in the collaboration instance data 920 using the method 500. In addition, the agent server 140 registers the consume request CR3 corresponding to the consume request definitions matching the URIs provided in the participant registration request. The agent server 140 then generates a participant token that the agent server 140 uses to uniquely identify the patient medical database client 160 and the collaboration ID of the collaboration into which it has been registered, and returns it to the patient medical database client 160 for use with future communications.

Figure 27:
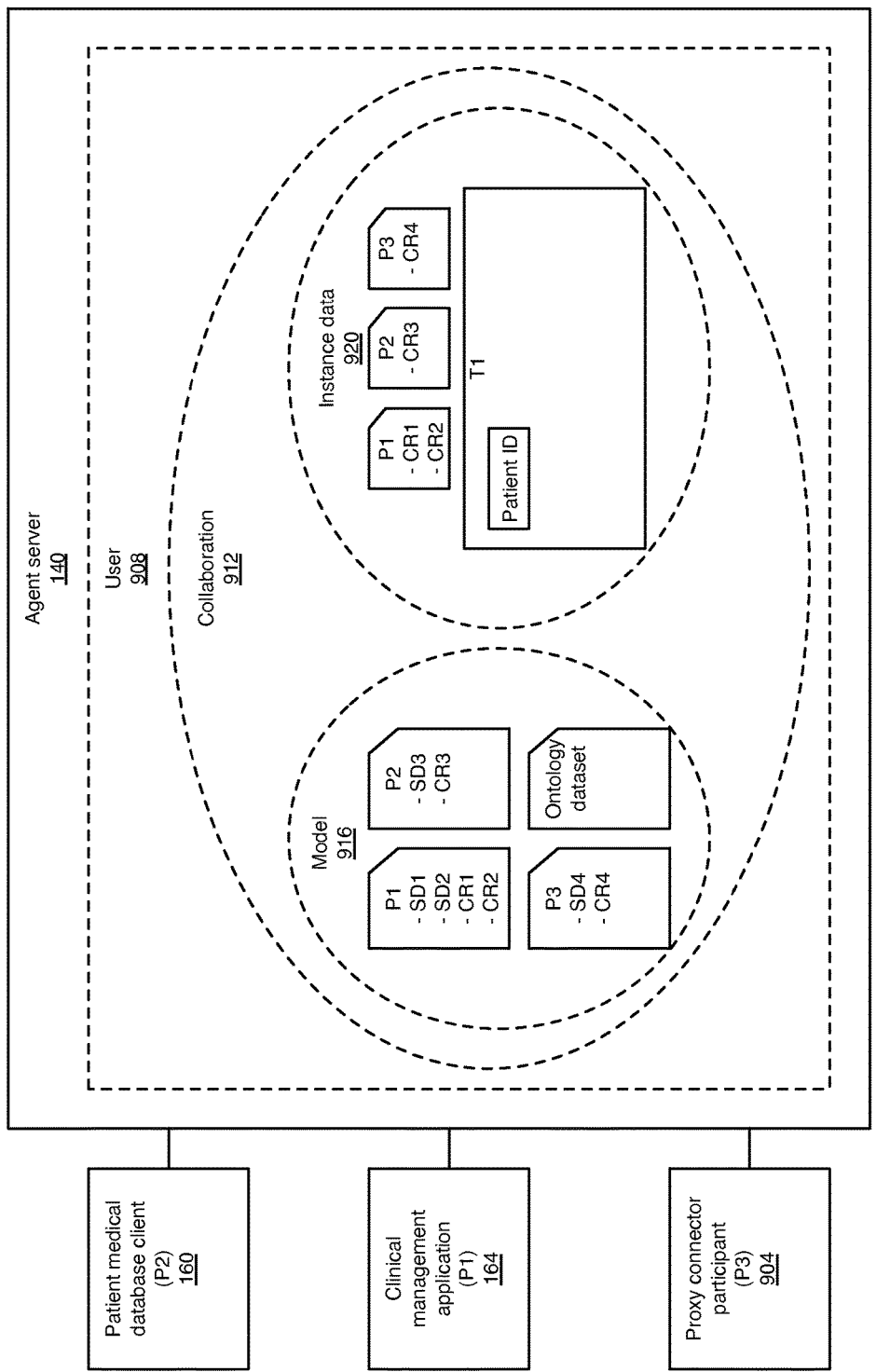
FIG. 27 illustrates the state of the collaboration of FIG. 26 after the patient medical database client is registered therein.

FIG. 27 illustrates the state of the collaboration after registration of the patient medical database client 160. As can be seen, the patient medical database client 160 (represented as P2,) has been instantiated in the instance data 920, together with its consume request, CR3. The patient medical database client 160 thereafter polls the agent server 140 regularly to determine if its consume request has undergone a state change.

As soon as the patient medical database client 160 is registered in the collaboration 912, the agent server 140 evaluates its consume request CR3 using the method 740, as a enable notification request was sent with the participant registration request. As previously noted, consume request CR3 identifies a single data item value, "patient ID". The agent server 140 determines that the consume request CR3 has been satisfied and thus undergone a state change, and flags it accordingly. Upon receipt of the next poll from the patient medical database client 160, the agent server 140 responds with the URI of the consume request CR3, together with the transaction ID for that transaction. When the patient medical database client 160 receives the URI of the consume request, it generates a request for the data item values having caused the state change in the consume request. This request includes the user token, the participant token, the URI corresponding to the consume request CR3, and the transaction ID for the transaction from which the values are sought. The agent server 140, upon confirming the user token with the identity server 148, provides the value of "patient ID" from the transaction identified by the transaction ID as requested by the patient medical database client 160.

When the patient medical database client 160 receives "patient ID" from the agent server 140, it retrieves the corresponding data from the patient medical database 52 and presents the patient's data via a user interface that enables the user to view previous entries and record new information. Assuming that the user is simply consulting with the patient, the user might enter in the length of time that the patient was consulted with into the patient medical database client 160. The patient medical database client 160 sends a communication to the database server 24 with the entry and, in turn, the database server 24 records the entry in the patient medical database 52. In addition, the patient medical database client 160 shares the data with the agent server 140. In particular, the patient medical database client 160 communicates the user token, the participant token, the URI of the share declaration SD3, "list of services provided", and the transaction ID provided with the data it relied upon to generate the shared values (i.e., the patient ID).

Upon receiving the shared data, the agent server 140 determines if it is ok to update the instance data with this value using the method 600, updates the instance data with the new values if permitted and evaluates any consume requests using the method 700

Figure 28:
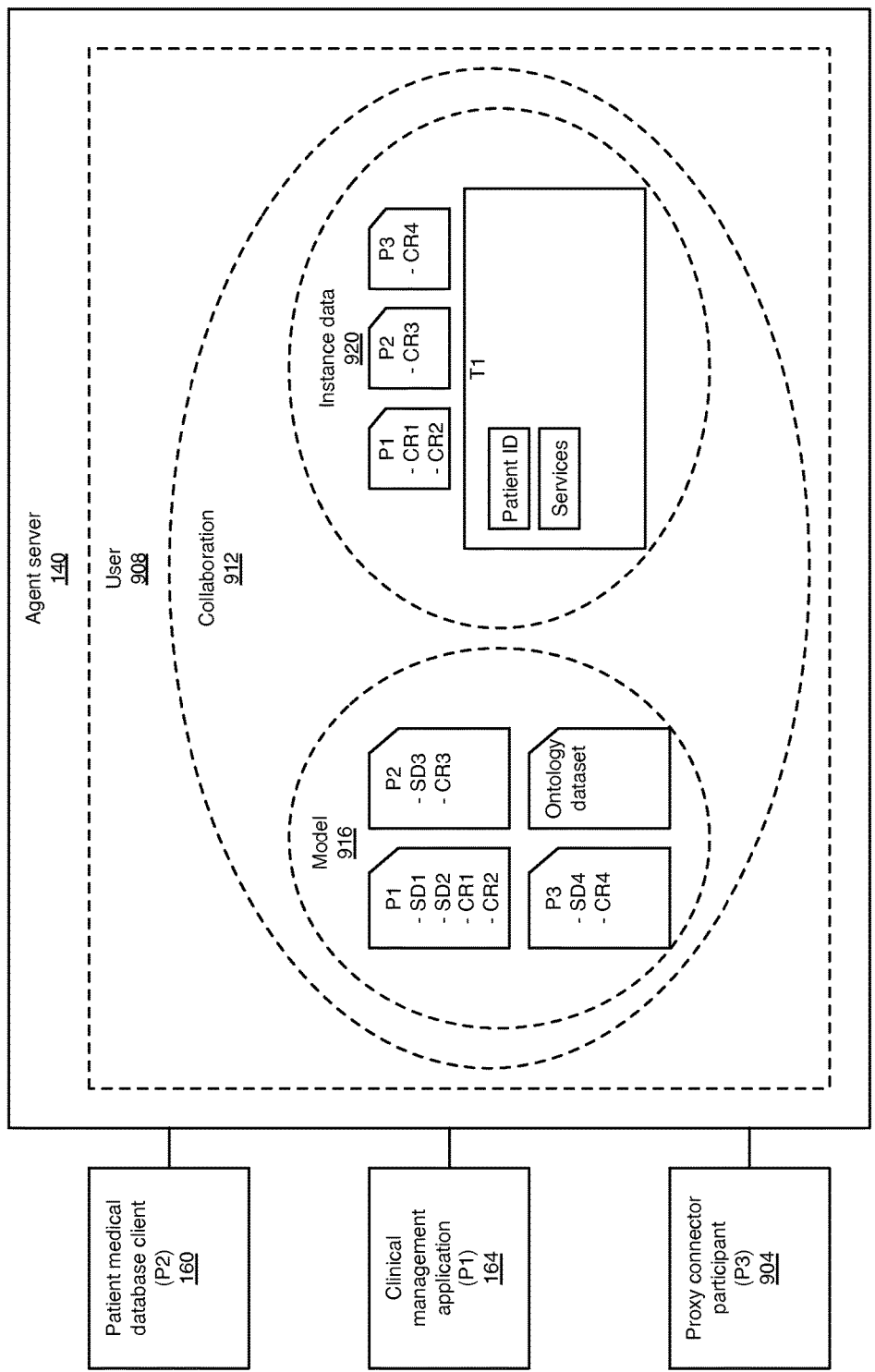
FIG. 28 illustrates the state of the collaboration of FIG. 27 after the patient medical database client shares values for "list of services provided" therein.

FIG. 28 illustrates the state of the collaboration after sharing of the list of services provided by the patient medical database client 160. As can be seen, the list of services provided is registered in the same transaction as "patient ID" with which they are associated.

As previously noted, consume request CR1 of the clinical management application 164 identifies a single data item, the list of services provided. The agent server 140 determines that the consume request CR1 has been satisfied and thus underwent a state change, and flags it accordingly. Upon receipt of the next poll from the clinical management application 164, the agent server 140 responds with the URI of the satisfied consume request CR1 and the transaction ID. When the clinical management application 164 receives the URI of the consume request, it generates a request for the data item values that caused a state change in the consume request. This request includes the user token, the participant token, the URI corresponding to the consume request CR1, and the transaction ID. The agent server 140, upon confirming the user token with the identity server 148, provides the current value(s) of the list of services provided as requested by the clinical management application 164.

In response to receiving the list of services provided, the clinical management application 164 calculates charges for each service provided. It then looks up the policy number and the person ID for the patient for their insurance coverage. The clinical management application 164 then shares values for "policy number", "person ID", "list of services provided", and "costs of services provided" with the agent server 140, as well as the URI of the associated share declaration SD2, the user token, the participant token, and the transaction ID provided with the data it relied upon to generate the shared values (i.e., the list of services provided).

Upon receiving the shared values, the agent server 140 determines if it is ok to update the instance data with these values using the method 600 and then updates these values in the instance data 920 and evaluates any consume requests using the method 700.

Figure 29:
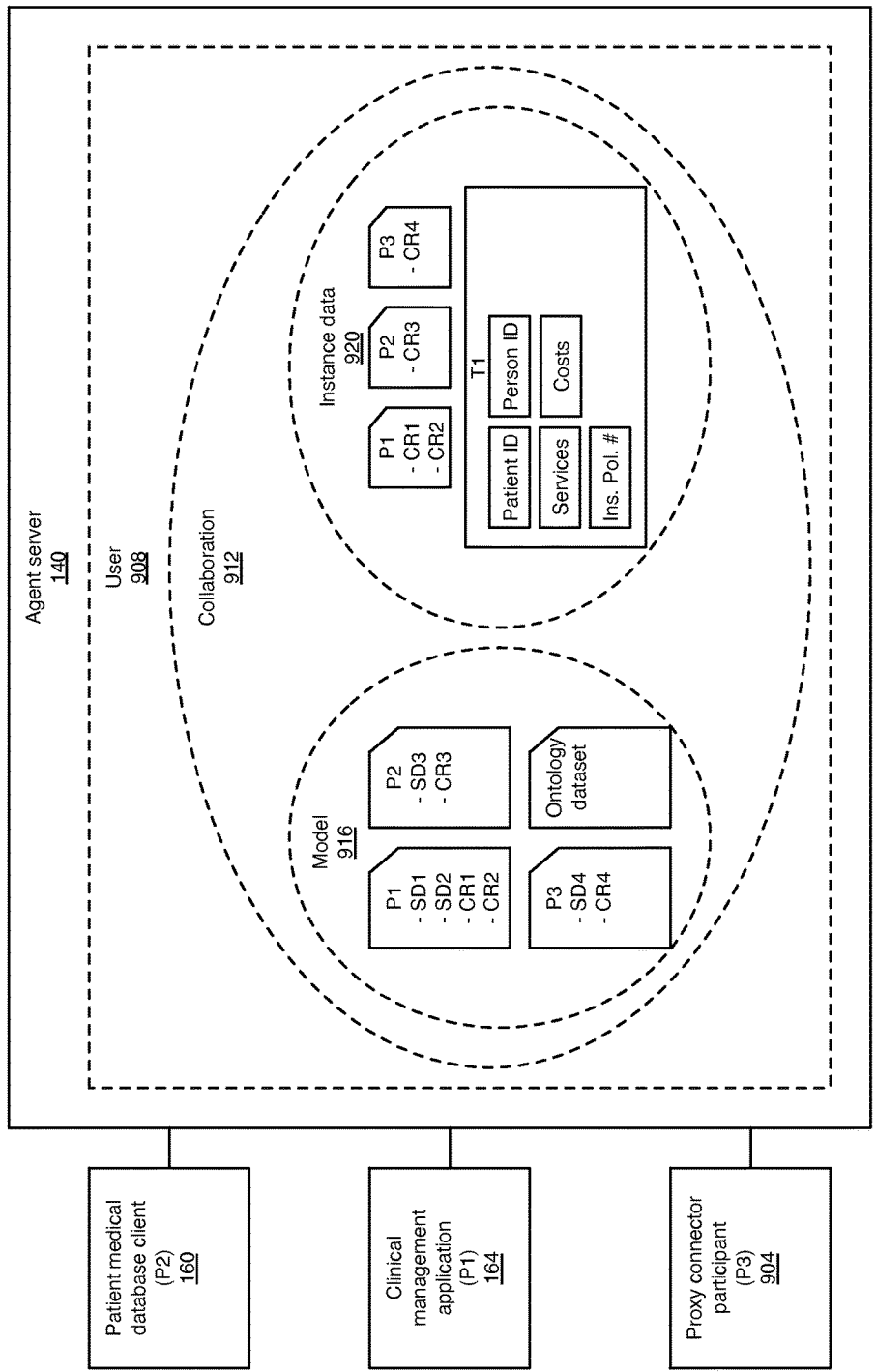
FIG. 29 illustrates the state of the collaboration of FIG. 28 after the clinical management application shares additional values therein in response to receiving the values for "list of services provided"

FIG. 29 illustrates the state of the collaboration after sharing of values for "insurance policy number", "person ID", "list of services provided" and "costs for the services provided" by the clinical management application 164. As can be seen, these values are registered in the same transaction as "patient ID" and "list of services provided" with which they are associated.

The agent server 140, in this case, determines that the consume request C4 of the proxy connector participant 904 has been satisfied and thus undergone a state change. As the proxy connector participant 904 is a server-side participant, the agent server 140 does not flag the consume request as having changed state, but instead sends the values satisfying the consume request CR4 (i.e., "policy number", "person ID", "list of services provided", including a translation of the standard service codes to carrier-specific codes, "costs of services provided") to the proxy connector participant 904, together with the user token, a participant token generated by the agent server 140 for the proxy connector participant 904 for this collaboration, the URI of the consume request that changed state, and the URI of the participant definition 208 of the proxy connector participant 904. The proxy connector participant 904 then passes these values to the Web connector, together with the user token, the participant definition URI, and the consume request definition URI.

In response, the Web connector retrieves the consume request definition CR4 and any associated share declarations (SD4) from the directory server 144. The consume request definition CR4 includes the syntax for generating the URL of the page to be interacted with served by the Web portal server 32 and any information as to where to enter data on the page, controls to interact with, etc. The Web connector then generates a page request from the Web portal server 32, enters values for the policy number, the person ID, the list of services provided, and the costs of the services provided on the page, and retrieves another page by interacting with a button on the page. Next, the Web connector reads data for the insurance-covered amounts for each service provided from this subsequent page using instructions in the consume request definition CR4 and provides data item values read to the proxy connector participant along with the URI of the share declaration SD4. The proxy connector participant, in turn, shares these values with the collaboration via the agent server 140.

Upon receiving the shared data from the proxy connector participant 904, the agent server 140 determines if it is ok to update the instance data with this value using the method 600 and then updates these values in the instance data 920 and evaluates any consume requests using the method 700.

Figure 30:
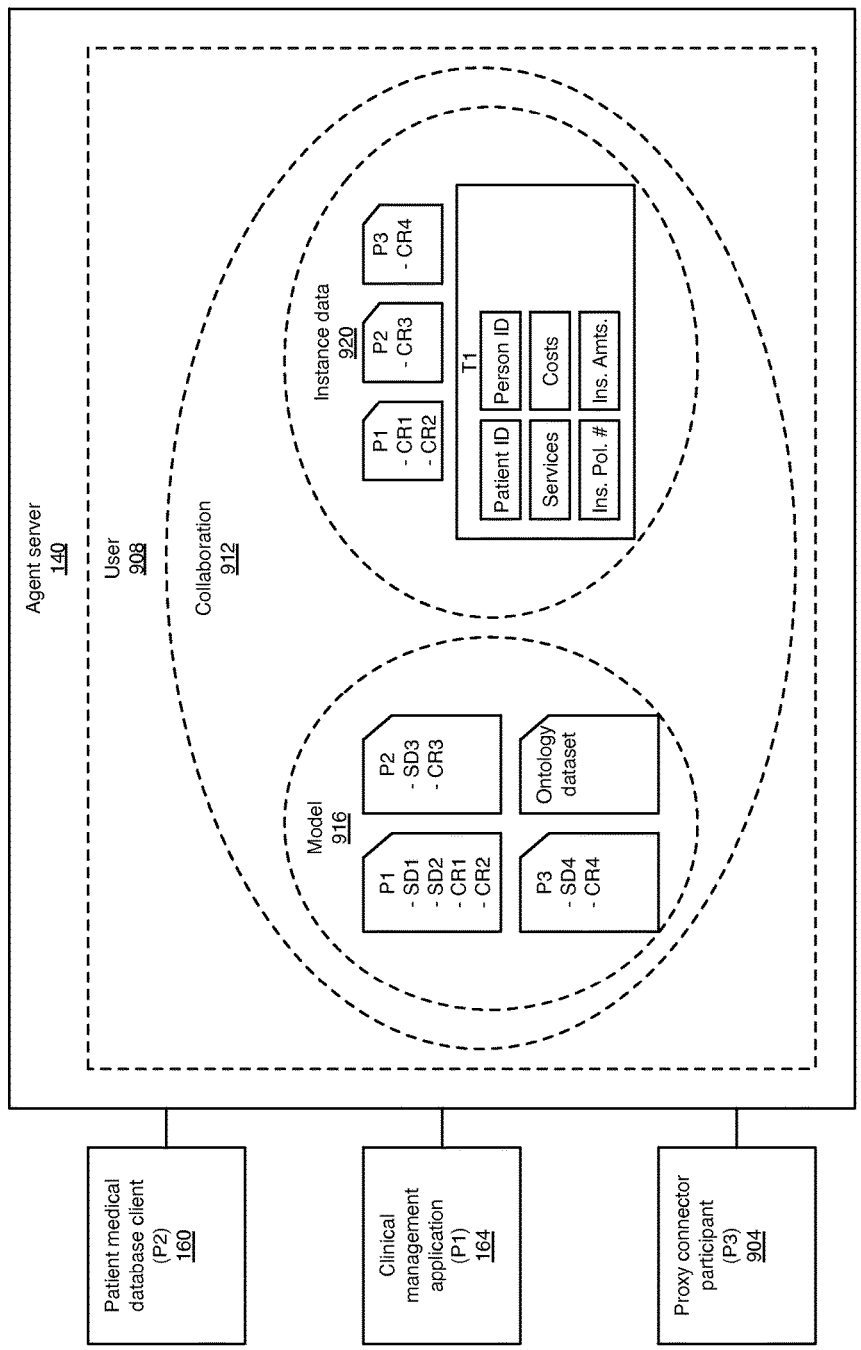
FIG. 30 illustrates the state of the collaboration of FIG. 29 after the Web connector shares values therein.

FIG. 30 illustrates the state of the collaboration after sharing of the insured amounts by the proxy connector participant 904. As can be seen, these values are registered in the same transaction as the patient ID and list of services provided with which they are associated.

As previously noted, consume request CR2 of the clinical management application 164 identifies a single data item, "insurance-covered amounts". The agent server 140 uses the ontology dataset in the collaboration model 916 to resolve "insurance-covered amounts", which does not appear in the collaboration instance data 920, to "insured amounts", which does appear in the collaboration instance data 920. It thus determines that the consume request CR2 has been satisfied, thereby changing its state, and flags it accordingly. Upon receipt of the next poll from the clinical management application 164, the agent server 140 responds with the URI of the consume request CR2 that changed state and the transaction ID. When the clinical management application 164 receives the URI of the consume request that changed state, it generates a request for the data item values for the consume request CR2. This request includes the user token, the participant token, the URI corresponding to the consume request CR2, and the same transaction ID. The agent server 140, upon confirming the user token with the identity server 148, provides the current value(s) of "insured amounts" as indirectly-requested by the clinical management application 164.

Upon receiving the insured amounts from the agent server 140, the clinical management application can complete an invoice for the services provided to the patient that shows the amount payable for each service provided net of the insured amount.

When the user selects another patient via the clinical management application 164, the clinical management application 164 shares the new value for "patient ID" with the agent server 140. As the newly-shared data is not accompanied by a transaction ID, the agent server 140 opens a new transaction for the newly-shared data.

Figure 31:
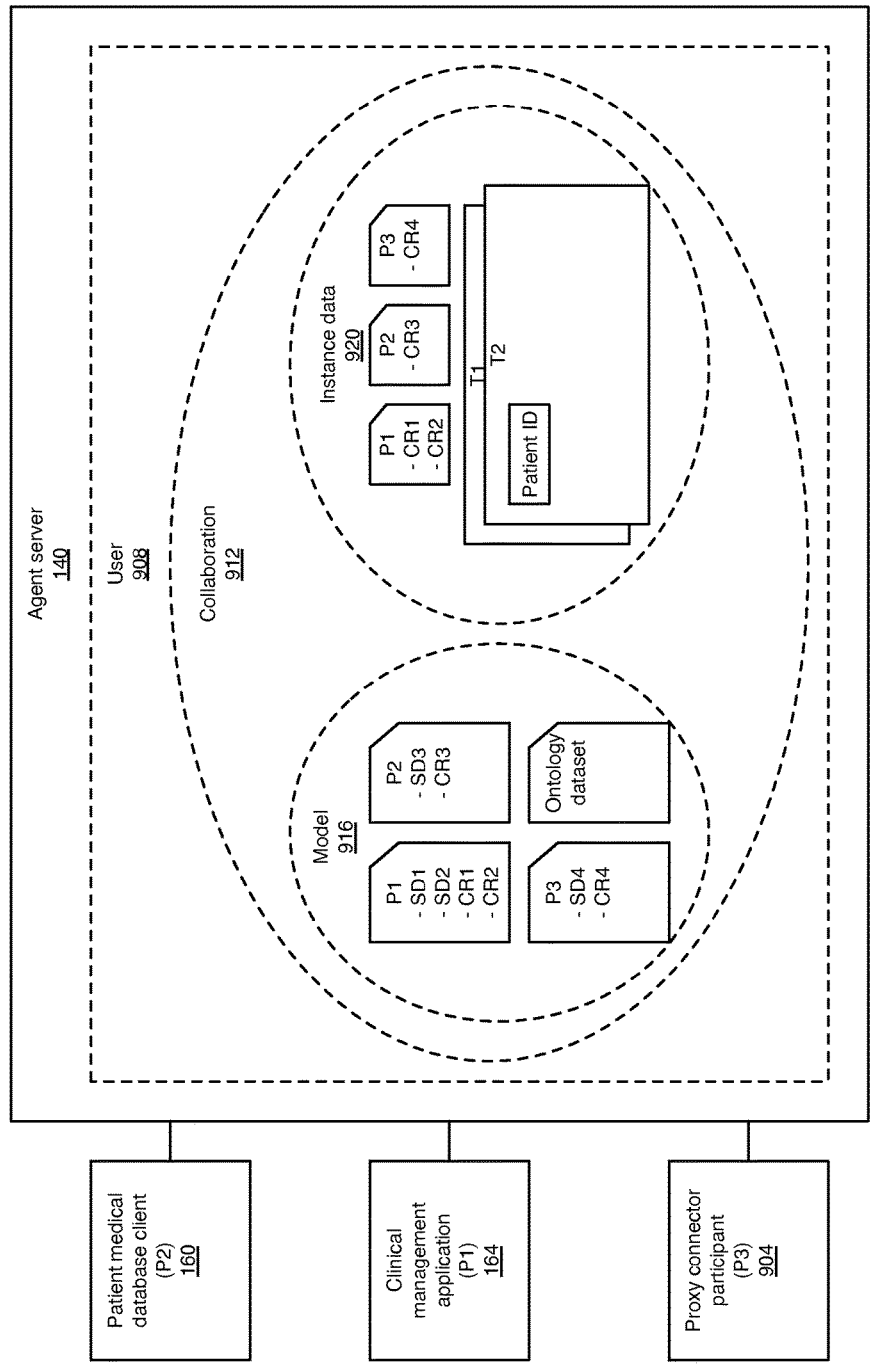
FIG. 31 illustrates the state of the collaboration of FIG. 30 after the clinical management application shares a new value for "patient ID" therein to start a new transaction.

FIG. 31 illustrates the state of the collaboration after a new patient has been selected in the clinical management application 164. As can be seen, the agent server 140 has created a new transaction for the newly-shared value of "patient ID", as it is not associated with any previously-received data.

The data-sharing server computer system 100 thus enables the user to interact with software systems or components thereof without the need to manually transfer data between these software systems in order to complete a task. Each software system interacts with the data-sharing server computer system 100 and has no knowledge of other software systems that are participating in the same collaboration. Further, the data-sharing server computer system 100 can interact with software systems on behalf of the user that the user would have had to interact with otherwise to complete the task.

While the method of enabling data-sharing in accordance with the invention has been described with respect to a particular embodiment, those skilled in the art will appreciate that various modifications can be made without affecting the underlying inventive approach.

While the main embodiment describes the various components of the stateful data-sharing service residing on the same physical computer, those skilled in the art will appreciate that the components can reside on separate physical computers.

Participant definitions and other artefacts relating to a collaboration can be defined within collaboration definitions and stored as a single artefact and parsed by the data-sharing server computer system in such a manner that participants are not provided access to the participant definitions of other participants, etc. Alternatively, the participant definitions and other artefacts can be assembled with the collaboration definition and delivered to a requesting system at the time the request is made.

The participant definitions, the collaboration definitions and other artefacts can be stored in various manners, such as files, database entries, etc.

While, in the described embodiments, the participant definitions, ontology datasets, etc. are instantiated in a collaboration model, they can also be retrieved from non-volatile storage as needed.

The various artefacts for collaborations can be stored as files, configuration scripts, configuration parameters stored in a database, etc.

Software systems can register as participants in collaborations without knowledge of all of the consume request definitions and share declarations defined for their participant type. In this case, a participant can register with a directory consume request for information from the participant definition stored in the collaboration model, including a list of consume request definitions and share declarations. This special type of registration allows the participant to register more than once without removing itself from the collaboration first. The reason for that is that the participant can only register once in the instance of the collaboration but there is no such restriction in the model since all such registrations are idempotent as information cannot be shared into the model. The participant can then re-register in the collaboration with an indication of which of the permitted consume requests set out in the consume request declarations it wants to be notified of updated values for. Participants can be generally configured to register consume requests corresponding to all consume request definitions listed in the participant definition, but can also be configured to only register a subset thereof upon being provided with a list of the consume request definitions in the collaboration model.

The data-sharing server computer system can enable notifications for each participant in a collaboration without explicit notification from the software systems themselves. In a particular embodiment, software systems can be notified of values for their consume requests having changed states by default, but could indicate that they wish to delay receiving such notifications as desired.

The data-sharing server computer system can be configured to permit collaborations to be destroyed in various ways. For example, participants could be permitted to destroy collaborations with permission. A collaboration can be destroyed when a certain value is shared, or when a calculated value based on the data item values in the collaboration meets a certain condition. Collaborations can be defined such they have expiration times, and can exceed those expiration times should activity continue within them.

While, in the above-described embodiment, the software systems poll the data-sharing server computer system to determine if updated values are available, the software systems can be notified of updates to requested data item values in other ways. For example, software systems can register endpoints at which they can be notified by the data-sharing server computer system when updated data item values are available. The data item values can also be provided directly to notify the software systems of the updates. Other methods by which the software systems can be notified of updated data item values will occur to those skilled in the art.

The data-sharing server computer system can be configured to enable more than one software system of the same type to participate in a collaboration. In such cases, a set of rules can define what data is accepted from each software system. For example, where two or more software systems are allowed to join a collaboration, the first may be an active participant, whereas the others may be allowed to receive shared values from the collaboration, but not share values to the collaboration. In another alternative mode, both participants may be permitted to share data to the collaboration, but the data shared by one of the participants may be given priority over the data shared by the other participants.

The share declarations can specify the kind of data being shared in a variety of manners, so that shared data will only be accepted if it is in the right form. For example, if a data item in a share declaration is defined as numeric, the data-sharing server computer system can reject non-numeric values for that data item.

The data-sharing server computer system can process data item values shared by software systems non-sequentially. For example, if there are numerous sets of data item values for the same share declaration in the update queue, the data-sharing server computer system can process only the last-received set of data item values for the current transaction, if any, and discard the rest from the queue.

The lifetime of the shared data values can be enforced by the data-sharing server computer system using an approach, such as that detailed in U.S. Patent Application Publication No. 20120310900, filed on Feb. 22, 2011 and published on Dec. 6, 2012, the entire contents of which are incorporated by reference herein. It will be understood that the time information for data shared by computing devices other than the data-sharing server computer system may need to be adjusted to compensate for differences between the computing device that generated the time information and the data-sharing server computer system's time.

The data-sharing server computer system can process a subset of the registered consume requests that are believed to relate to updated data item values in an alternative mode. In this manner, processor load can be reduced.

While, in the above-described embodiment, the data-sharing server computer system permits participant registration with and without a collaboration ID, it could enforce either registration with a collaboration ID or it could ignore/not accept collaboration IDs and assign participants to collaborations based on heuristics. Further, the data-sharing server computer system may disallow participant registration without registering into a collaboration in some or all scenarios.

In other modes, where there is more than one collaboration that a participant may be registered into, the data-sharing server computer system can be configured to register the participant into a particular collaboration based on heuristics. For example, the data-sharing server computer system can be configured to register the participant into the most recently created collaboration, the earliest created collaboration, or the collaboration with the most recent data-sharing activity (i.e., the receipt of values shared by a participant).

While the invention has been described with specificity to a Java implementation, other types of implementations will occur to those of skill in the art. For example, the stateful data sharing service could be written in any one of a number of programming languages, such as Microsoft's C# or Javascript. Any general purpose programming language could be substituted.

Instead of processing all consume requests each time data values are changed, it may be desirable in some circumstances to determine which consume requests are or may be applicable based on the semantic information. In another alternative configuration, all consume requests can be processed independent of the receipt of data item values at a somewhat regular frequency, such as every 100 milliseconds.

Instead of storing various artefacts such as collaboration definitions and participant definitions in the directory persistently, the software systems can provide this information as required, such as during registration.

The interfaces of the various components of the stateful data-sharing service could be substituted with any of a variety of interfaces, such as Java Remote Method Invocation, .NET Windows Communication Framework, Message queue style communications or even simple function calls.

RDF can be replaced as the metadata format by other types of metadata languages such as, for example, DAML, and XML.

SPARQL is only one possible query language for use in constructing standing queries. Other examples include XsRQL and RQL.

The stateful data-sharing service can maintain and update separate transactions in the shared value space or can create separate shared value spaces for each type of transaction.

While a value update queue is used in the above-described embodiment, other methods of processing sets of data item values could be used. For example, alternative methods include the use of an exclusive lock, parallel execution with exclusive data spaces or any other method that ensures a consistent end-state for the shared value space after update.

Any identifier that provides uniqueness within the referenceable address space would work in place of URIs. For example, an integer or a Globally Unique Identifier ("GUID") could be employed.

Various components of the stateful data-sharing service can be used with multiple other instances of a component. For example, a single directory server can be used for two or more agent servers.

Consume requests can be semantically resolved to data items specified in the share declarations of other participants as part of a pre-processing stage for the standing requests, in some cases.

When processing data item values received from software systems, the data-sharing server computer system can alternatively ignore all but the latest values for a share declaration URI, thereby discarding previous values generated for the same or a prior transaction.

Other methods for associating software systems with a user can be used. For example, a user can log into the data-sharing server computer system and the IP address of the personal computing device from which the login request is received can be associated with the user for future communications. In another example, each software system can be required to provide login credentials for the user to the data-sharing server computer system. The participant token thereafter generated by the data-sharing server computer system and used by the software system for future communications can be associated with the user's identity. Still yet other methods will occur to those skilled in the art.

The stateful data-sharing service can create collaborations for a user wherein software system types for a collaboration are not pre-specified. In this manner, all software systems executing on the user's computing device can share via a single collaboration on an ad-hoc basis.

The data-sharing server computer system can be configured to create a collaboration when a participant registration request is received from a software system and no existing collaboration which the software system is permitted to join has capacity for it.

Computer-executable instructions for implementing the stateful data sharing service on a computer system could be provided separately from the computer system, for example, on a computer-readable medium (such as, for example, an optical disk, a hard disk, a USB drive or a media card) or by making them available for downloading over a communications network, such as the Internet. The computer-executable instructions could be bundled with one or more software systems. For example, visiting a website that includes software system functionality could trigger a download event for the computer-executable instructions.

The above-described embodiments are intended to be examples of the present invention and alterations and modifications may be effected thereto, by those of skill in the art, without departing from the scope of the invention that is defined solely by the claims appended hereto.

What is claimed is:

1. A method for enabling data sharing between software systems for a plurality of users, the method comprising:
    simultaneously managing, with a computer system, at least one data-sharing session for each said user, wherein managing one of
    said data-sharing sessions comprises:
        for each of a plurality of software systems associated with one of said users:
            receiving a request from said software system to join said data-sharing session associated with said user, said request including a credential;
            determining if said credential is associated with said user; and
            if said credential is determined to be associated with said user, registering said software system in said data-sharing session;
        registering requests for said registered software systems associated with said user to be notified of updates to values of sets of requested data;
        storing values for data items received from said registered software systems associated with said user; and
        whenever at least one of said values of said data items is updated by any one of said registered software systems associated with said user:
            resolving said sets of requested data to sets of said data items using semantic descriptions provided for said data items and said sets of said requested data; and
            for each registered software system associated with said user that registered a request to be notified of updates to said sets of said requested data, providing updates to said values of said sets of said data items to which said sets of said requested data semantically resolve to said registered software system associated with said user.

2. The method of claim 1, wherein said computer system maintains separate user spaces in storage of said computer system for each said user in which said data item values shared by said software systems providing said credential for said user are stored.

3. The method of claim 1, wherein, for each said user, at least one of said software systems is executing on a personal computing device operated by said user.

4. The method of claim 3, wherein said computer system receives login credentials for said one user from one of said at least one software systems to associate said at least one software system with said user.

5. The method of claim 1, wherein each said data-sharing session corresponds to one of a plurality of data-sharing session types, and said computer system uses a collaboration definition for each said data-sharing session type to define what types of said software systems can participate in said data-sharing sessions of said data-sharing session type.

6. The method of claim 5, wherein said computer system uses a participant definition for each said software system type to define said sets of said requested data items it can request values for.

7. The method of claim 6, wherein said participant definition includes said semantic descriptions for said sets of said requested data that said software system type can request values for.

8. The method of claim 6, wherein said participant definition defines which of said data items said software systems of said software system type can share values for.

9. The method of claim 8, wherein said participant definition includes said semantic descriptions for said sets of said data items that said software systems of said software system type can share values for.

10. The method of claim 1, wherein said computer system uses at least one ontology dataset to resolve said sets of said requested data to said sets of said data items.

11. The method of claim 5, wherein said collaboration definition specifies at least one ontology dataset that said computer system uses to resolve said sets of said requested data to said data items.

12. The method of claim 6, wherein said participant definition includes configuration information for configuring said software systems of said software system type.

13. The method of claim 5, wherein said computer system creates each said data-sharing session in response to receiving a collaboration creation request specifying said collaboration definition corresponding to said data-sharing session type that is desired.

14. The method of claim 5, wherein said computer system permits only one of said software systems of each said software system type specified in said collaboration definition to participate in said data-sharing session.

15. The method of claim 14, wherein said computer system receives a request from one of said software systems to participate in a data-sharing session, said request identifying said software system type of said one software system, said computer system only permitting said software system to participate in one of said data-sharing sessions for which said corresponding collaboration definition specifies that said software system type of said one software system is permitted to participate therein.

16. The method of claim 15, wherein said computer system registers said one software system outside of said data-sharing sessions if all of data-sharing sessions in which said one software system is permitted to participate already have other of said software systems of said software system type participating therein, and subsequently registers said one software system in one of said data-sharing sessions in which said one software system is permitted to participate has capacity for said one software system.

17. The method of claim 15, wherein said computer system maintains separate user spaces in storage of said computer system for each said user in which said data item values shared by said software systems providing said credential for said user are stored, and wherein said computer system registers said one software system in said user space corresponding to said user for which said one software system has provided said credential and outside of data-sharing sessions if all of said data-sharing sessions in which said one software system is permitted to participate already have other of said software systems of said software system type participating therein until one of said data-sharing sessions in which said one software system is permitted to participate has capacity for said one software system.

18. The method of claim 15, wherein said computer system determines that only one of said data-sharing sessions in which said one software system is permitted to participate has capacity for said one software system, and said computer system registers said one software system in said one data-sharing session.

19. The method of claim 15, wherein said computer system determines that at least two of said data-sharing sessions in which said one software system is permitted to participate has space for said one software system, and said computer system reports an error to said one software system.

20. The method of claim 14, wherein said computer system receives a request from one of said software systems to participate in a data-sharing session, said request specifying an identifier for a particular one of said data-sharing sessions managed by said computer system for said user for which said one software system has provided said credential, said computer system placing said one software system in said particular one data-sharing session if said collaboration definition associated with said particular data-sharing session indicates that said one software system is permitted to join said particular data-sharing session and if said particular data-sharing session has capacity for said one software system.

21. The method of claim 17, wherein said computer system determines that at least two of said data-sharing sessions in which said one software system is permitted to participate has space for said one software system, and said computer system registers said one software system in one of said at least two data-sharing sessions based on heuristics.

22. The method of claim 21, wherein said computer system registers said one software system in a later created one of said at least two data-sharing sessions.

23. The method of claim 21, wherein said computer system registers said one software system in an earlier created one of said at least two data-sharing sessions.

24. The method of claim 21, wherein said computer system registers said one software system in one of said at least two data-sharing sessions having more recent data-sharing activity.

25. A computer system for enabling data sharing between software systems for a plurality of users, the system comprising:
    a processor; and
    storage storing computer-executable instructions that, when executed by said processor, cause said processor to simultaneously manage at least one data-sharing session for each said user wherein managing one of said data-sharing sessions comprises:
        for each of a plurality of software systems associated with one of said users:
            receiving a request from said software system to join said data-sharing session associated with said user, said request including a credential;
            determining if said credential is associated with said user; and
            if said credential is determined to be associated with said user, registering said software system in said data-sharing session;

registering requests for said registered software systems associated with said user to be notified of updates to values of sets of requested data;

storing values for data items received from said registered software systems associated with said user; and whenever at least one of said values of said data items is updated by any one of said registered software systems associated with said user:

resolving said sets of said requested data to a set of said data items using semantic descriptions provided for said requested data and said data items; and for each registered software system associated with said user that registered a request to be notified of updates to said sets of said requested data, providing updates to said values of said sets of said data items to which said sets of said requested data semantically resolve to said registered software systems associated with said user.

26. The system of claim 25, wherein said processor maintains separate user spaces in storage of said computer system for each said user in which said data item values shared by software systems providing said credential for said user are stored.

27. The system of claim 25, wherein, for each said user, at least one of said software systems is executing on a personal computing device operated by said user, and wherein said processor receives login credentials from said at least one software system.

28. The system of claim 25, wherein each said data-sharing session corresponds to one of a plurality of data-sharing session types, and said processor uses a collaboration definition for each said data-sharing session type to define what types of said software systems can participate in said data-sharing sessions of said data-sharing session type.

29. The system of claim 28, wherein said processor uses a participant definition for each said software system type to define what data items it can request values for.

30. The system of claim 29, wherein said participant definition includes said semantic descriptions for said sets of said requested data that said software system type can request values for.

31. The system of claim 29, wherein said participant definition defines which of said data items said software systems of said software system type can share values for.

32. The system of claim 31, wherein said participant definition includes said semantic descriptions for said data items that said software systems of said software system type can share values for.

33. The system of claim 25, wherein said processor uses at least one ontology dataset to resolve said sets of requested data to said sets of said data items.

34. The system of claim 28, wherein said collaboration definition specifies at least one ontology dataset that said processor uses to resolve said sets of said requested data to said data items.

35. The system of claim 29, wherein said participant definition includes configuration information for configuring said software systems of said software system type.

36. The system of claim 28, wherein said processor creates each said data-sharing session in response to receiving a collaboration creation request specifying said collaboration definition corresponding to said data-sharing session type that is desired.

37. The system of claim 28, wherein said processor permits only one of said software systems of each said software system type specified in said collaboration definition to participate in said data-sharing session.

38. The system of claim 37, wherein said processor receives a request from one of said software systems to participate in a data-sharing session, said request identifying said software system type of said one software system, said processor only permitting said software system to participate in one of said data-sharing sessions for which said corresponding collaboration definition specifies that said software system type of said one software system is permitted to participate therein.

39. The system of claim 38, wherein said processor registers said one software system outside of said data-sharing sessions if all of said data-sharing sessions in which said one software system is permitted to participate already have other of said software systems of said software system type participating therein, and subsequently registers said one software system in said data-sharing sessions in which said one software system is permitted to participate has capacity for said one software system.

40. The system of claim 38, wherein said processor maintains separate user spaces in said storage for each said user in which said data item values shared by said software systems providing said credential for said user are registered, and wherein said processor registers said one software system in said user space corresponding to said user for which said one software system has provided said credential and outside of said data-sharing sessions if all of said data-sharing sessions in which said one software system is permitted to participate already have other of said software systems of said software system type participating therein until one of said data-sharing sessions in which said one software system is permitted to participate has capacity for said one software system.

41. The system of claim 38, wherein said processor determines that only one of said data-sharing sessions in which said one software system is permitted to participate has capacity for said one software system, and said processor registers said one software system in said one data-sharing session.

42. The system of claim 38, wherein said processor determines that at least two of said data-sharing sessions in which said one software system is permitted to participate has space for said one software system, and said processor reports an error to said one software system.

43. The system of claim 37, wherein said processor receives a request from one of said software systems to participate in a data-sharing session, said request specifying an identifier for a particular one of said data-sharing sessions managed by said computer system, said processor registering said one software system in said particular one data-sharing session if said collaboration definition associated with said particular data-sharing session indicates that said one software system is permitted to join said particular data-sharing session and if said particular data-sharing session has capacity for said one software system.

44. The system of claim 38, wherein said processor determines that at least two of said data-sharing sessions in which said one software system is permitted to participate has space for said one software system, and said processor registers said one software system in one of said at least two data-sharing sessions based on heuristics.

45. The system of claim 44, wherein said processor registers said one software system in a later created one of said at least two data-sharing sessions.

46. The system of claim 44, wherein said processor registers said one software system in an earlier created one of said at least two data-sharing sessions.

47. The system of claim 44, wherein said processor registers said one software system in one of said at least two data-sharing sessions having more recent data-sharing activity.

48. A method for enabling data sharing between software systems for a plurality of users, the method comprising:
simultaneously managing, via a computer system, at least one data-sharing session for each said users;
receiving requests via a computer system from software systems to join data-sharing sessions managed by said computer system, each of said software systems providing a credential for one of said users; and
for each request, registering, by said computer system, said software systems in one of said data-sharing sessions managed for said user for which said software system provided said credential after said credential is determined to be authentic and to correspond to said user associated with said data-sharing sessions; and
for each data-sharing session:
maintaining requests from said software systems registered in said data-sharing session to be notified of updates to values of sets of requested data; and
storing values for data items shared by said software systems registered in said data-sharing session; and
whenever at least one of said values is updated:
resolving said sets of said requested data to sets of said data items using semantic descriptions provided for said data items and said requested data; and
notifying said software systems that registered a request to be notified of updates to said sets of said requested data when updates to said values of said sets of said data items resolving to said sets of requested data are available.

49. A method for enabling data sharing between software systems for a plurality of users, the method comprising:
simultaneously managing at least one data-sharing session for each said users;
receiving a request to participate in one of said data-sharing sessions from a software system providing a credential for one of said users via said computer system;
registering, via said computer system, said software system in one of said data-sharing sessions managed for said user for which said software system provided said credential after said credential is determined to be authentic and to correspond to said user associated with said data-sharing sessions;
maintaining requests from said software system to be notified of updates to values of sets of requested data;
storing values of data item shared by other software systems in said one data-sharing session; and
whenever at least one of said values of said data items is updated:
resolving said sets of said requested data to sets of said data items using semantic descriptions provided for said data items and said sets of requested data; and
notifying said software system when updates to said values of said sets of said data items resolving to said sets of requested data items are available.

50. A method for enabling data sharing between software systems, the method comprising:
simultaneously managing a set of data-sharing sessions for each of at least two users;
receiving a request via a computer system from a software system providing a credential for one of said users to participate in one of said set of data-sharing sessions managed for said one user;
determining, by said computer system, if said software system can be registered in said one of said set of data-sharing sessions managed for said user by determining if said credential is authentic and corresponds to said user; and
creating, by said computer system, an additional data-sharing session and registering said software system in said additional data-sharing session, if said software system cannot be registered in said one of said set of data-sharing sessions managed for said user.

* * * * *